(12) United States Patent
Testrut et al.

(10) Patent No.: US 7,867,444 B2
(45) Date of Patent: Jan. 11, 2011

(54) LAB CELL CENTRIFUGING MODULE

(75) Inventors: Dietmar Testrut, West Harrison, NY (US); Lutz Doms, Poohl (DE); Christian Rehm, Isen (DE)

(73) Assignee: Siemens Healthcare Diagnostics, Inc., Tarrytown, NY (US)

( * ) Notice: Subject to any disclaimer, the term of this patent is extended or adjusted under 35 U.S.C. 154(b) by 1730 days.

(21) Appl. No.: 10/439,205

(22) Filed: May 15, 2003

(65) Prior Publication Data

US 2003/0223916 A1 Dec. 4, 2003

Related U.S. Application Data

(60) Provisional application No. 60/384,363, filed on May 30, 2002.

(51) Int. Cl.
*B01L 9/06* (2006.01)

(52) U.S. Cl. .................... 422/65; 422/104; 211/85; 211/132.1

(58) Field of Classification Search ............ 422/65, 422/104; 211/85, 126.6, 130.1, 132.1, 195
See application file for complete search history.

(56) References Cited

U.S. PATENT DOCUMENTS 5,131,547 A * 7/1992 Goldberg ............... 211/149
5,971,175 A * 10/1999 Bustos .................... 211/187
6,001,310 A * 12/1999 Shaffer et al. ............ 422/102
6,277,630 B1 * 8/2001 Brophy et al. ........... 435/288.4
6,318,570 B1 * 11/2001 Mueller et al. ........... 211/181.1
7,141,213 B1 * 11/2006 Pang et al. ................ 422/65

FOREIGN PATENT DOCUMENTS

| JP | 3-282262 | 12/1991 |
|----|----------|---------|
| JP | 2001-505648 | 4/2001 |
| WO | 98/01760 | 1/1998 |

\* cited by examiner

*Primary Examiner*—Jill Warden
*Assistant Examiner*—Paul S Hyun

(57) ABSTRACT

A compressible and expandable sample tube holder includes a housing with a plurality of adjacent section members, movable toward and away from each other. Biasing members normally maintain the section members in an expanded condition. In the compressed condition the spacing between section members is reduced. A sample tube breakage detector includes slidable plungers having a protracted position that corresponds to a broken sample tube and a retracted position that corresponds to an unbroken sample tube in the sample tube holder. A detector compares the plunger positions before and after centrifuge spin to detect any broken sample tubes in the sample tube holder. A gripper device for the sample tube holder includes a lifting probe and a stabilizer to stabilize the sample tube holder during lifting. The gripper device and breakage detector are raised and lowered by a raising and lowering device having first and second telescoping members.

4 Claims, 38 Drawing Sheets

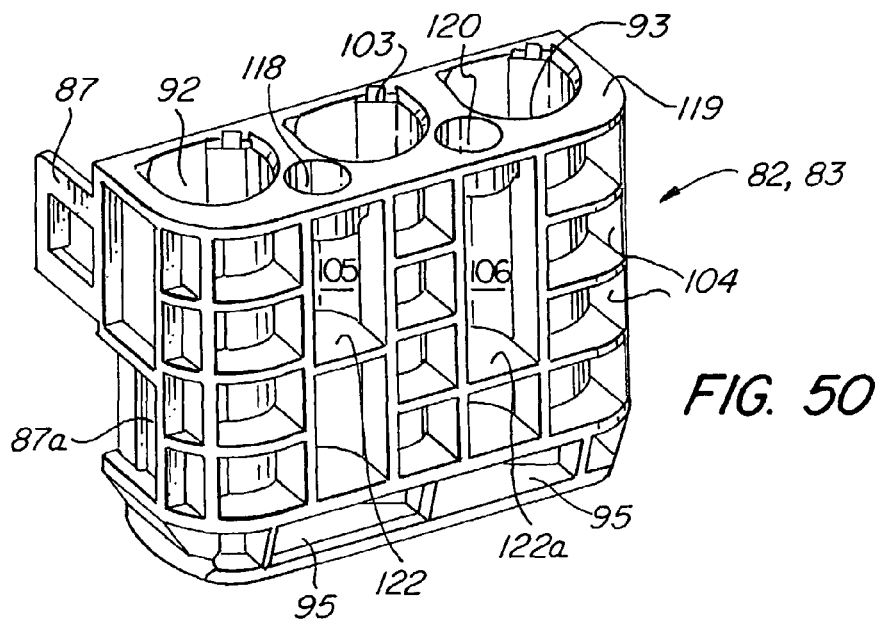
FIG. 50
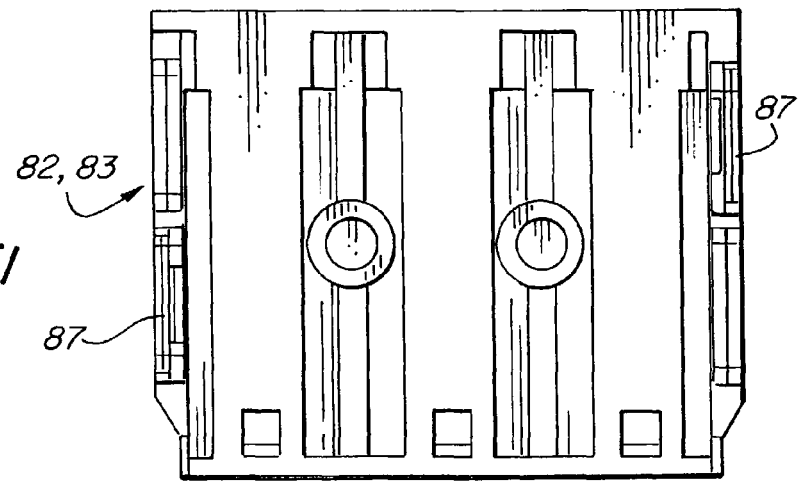
FIG. 51
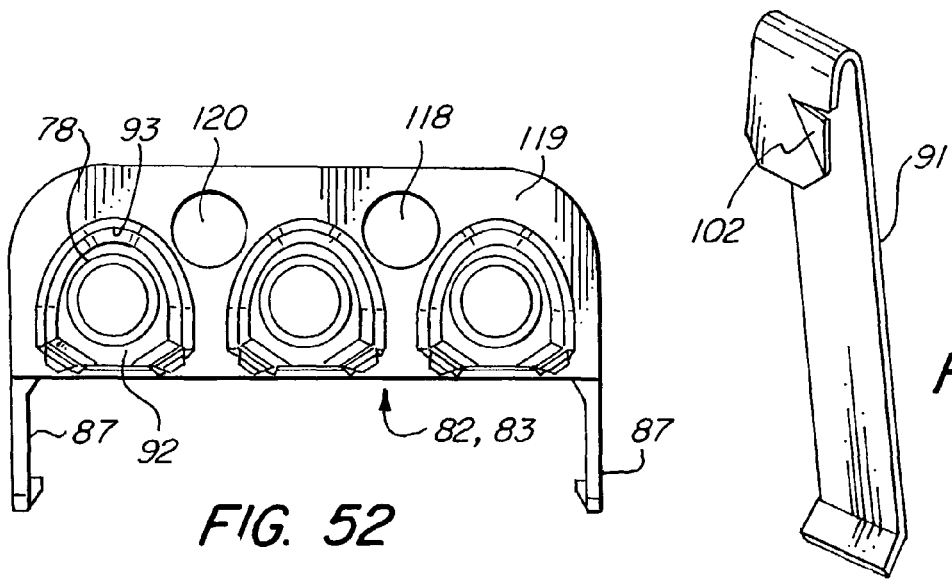
FIG. 52
FIG. 53

LAB CELL CENTRIFUGING MODULE

This invention relates to a lab cell centrifuging module in an automated body fluid analysis system, and more particularly to an expandible centrifuge bucket for sample tubes, a bucket gripper device with a sample tube breakage detector, and an input-output device for raising and lowering the expandible bucket relative to the centrifuge.

OPERATION SUMMARY

The lab cell centrifuging module (also referred to as the "module") is a system that receives capped sample tubes, from an incoming section of a main conveyor, for centrifuging and decapping. Sample tubes are robotically positioned in expandible buckets within the system that hold, for example, fifteen sample tubes. A system robot sequentially transfers four loaded buckets into a centrifuge for spinning. The spun sample tubes are then robotically removed from the centrifuge and robotically transferred to a decapper device for decapping. The decapped sample tubes are robotically delivered to an outgoing section of the main conveyor for transport to another processing station.

During startup there are four empty buckets 19 (FIG. 37) on each of three queues 13, 14 and 15 (FIGS. 2-4) for a total of twelve buckets. Four buckets are located on the unloading queue 13 (FIG. 4) and four buckets are located on each loading queue 14 and 15. The buckets 19 (FIG. 37), which are in a normally expanded condition, are positioned toward the same corresponding end of each of the queues 13, 14, 15, that is the forward left end, as shown in FIG. 3, also known as the home position 37 (FIGS. 32 and 35) of the queues 13, 14, 15.

A first of the continuing robotic operations of the module is to load one of the loading queues, such as the loading queue 14, with capped sample tubes. The capped sample tubes are transported to the module on an incoming section of the main conveyor 1. The sample tube delivery robot 8 (FIG. 3) transfers capped sample tubes from the conveyor 1 to buckets 19 in the loading queue 14.

When up to all four buckets 19 in the loading queue 14 have been loaded with capped sample tubes, the buckets are shifted to the opposite end of the loading queue 14 by a slide carriage 24 (FIG. 35) that is a component of the loading queue 14.

The loading queue 14 is sized such that when buckets are shifted from the home end 37 (FIGS. 32 and 35) to the opposite end thereof, the bucket 19 which was at the home end is now aligned with bucket deflectors 26, 27. The bucket deflectors 26, 27 compress the normally expanded bucket 19 to enable the bucket gripper robot 7 to transfer the deflected or compressed buckets to the centrifuge 4 (FIG. 2) through an opening 28 in the unloading queue 13 (FIG. 3).

While the bucket transfer operation from the loading queue 14 to the centrifuge 4 is taking place, the sample tube delivery robot 8 (FIG. 3) begins to transfer capped sample tubes from the incoming section of the conveyor 1 to the next loading queue 15. Thus the bucket transfer operation from the loading queue 14 to the centrifuge 4 takes place simultaneously with the sample tube transfer operation from the conveyor 1 to the loading queue 15.

In addition, as soon as a loaded bucket is transferred from the loading queue 14 to the centrifuge 4 by the bucket gripper robot 7, the bucket gripper robot 7 transfers an empty bucket from the unloading queue 13 back to the loading queue 14 to replace the loaded bucket that was just removed for transfer to the centrifuge. This exchange operation between loaded buckets from the loading queue 14 and unloaded buckets from the unloading queue 13 continues until all loaded buckets from the loading queue 14 are in the centrifuge and are replaced by empty buckets from the unloading queue 13.

Once again the exchange of buckets between the unloading queue 13 and the loading queue 14 takes place simultaneously while capped sample tubes are also simultaneously transferred, one by one, from the incoming section of the conveyor 1 to the loading queue 15. Thus, there is alternate loading of empty buckets on the loading queues 14 and 15.

When all loaded buckets 19 from the loading queue 14 are transferred into the centrifuge 4 a spin operation begins and the unloading queue 13 is empty of all buckets.

During the spin operation the sample tube delivery robot 8 continues to transfer sample tubes from the incoming section of the conveyor 1 to the loading queue 15. When the spin cycle is completed the bucket gripper robot 7 sequentially removes a bucket 19 of spun sample tubes from the centrifuge 4, places the bucket of spun sample tubes on the unloading queue 13, and removes a bucket 19 of sample tubes from the loading queue 15 for placement in the centrifuge 4, in the centrifuge space vacated by removal of the bucket of spun sample tubes. This sequential operation continues until all four buckets 19 of spun sample tubes from the centrifuge 4 are removed and replaced by loaded buckets 19 from the loading queue 15. Thus there is alternate transfer of loaded buckets 19 from the loading queues 14 and 15 to the centrifuge 4.

The sample tube gripper robot 6 also simultaneously removes individual spun sample tubes from the buckets 19 that are removed from the centrifuge 4 and placed on the unload queue 13. The removed individual spun sample tubes are transported by the sample tube gripper robot 6 to either one of the decappers 16, 17 (FIG. 3).

While the bucket exchange is taking place between buckets in the loading queue 15 and the spun buckets from the centrifuge the sample tube delivery robot 8 once again transfers capped sample tubes from the incoming section of the main conveyor 1 to the empty buckets in the loading queue 14. This cycle of operations by the sample tube gripper robot 6, the bucket gripper robot 7 and the sample tube delivery robot 8 take place simultaneously and repetitively.

Decapped sample tubes are transferred by the sample tube gripper robot 6 from the decappers 16, 17 to a rectangular path conveyor 18 (FIGS. 3 and 4). The sample tube delivery robot 8 transfers a spun and decapped sample tube from the rectangular path conveyor 18 to the conveyor 1 for transport to another processing station.

SUMMARY OF THE INVENTION

The invention includes a compressible and expandible sample tube holder having a housing with a predetermined number of sample tube openings for receiving sample tubes. The housing includes a plurality of adjacent section members, including a pair of end section members, and at least one middle section member, assembled together in side by side arrangement. Each of the section members are movable toward and away from an adjacent section member. Biasing means are provided between the end section members and the middle section member to maintain the end section members and the middle section member in a side by side spaced relationship that defines an expanded condition of the housing. The housing has a compressed condition when opposing forces applied to the end section members overcome the biasing means and reduce the spaced relationship between each of the section members a predetermined amount. Connecting means are provided on each of the section members to secure each of the section members together in the movable adjacent side-by-side arrangement.

The invention also includes a sample tube breakage detector having a housing with a plurality of slidable plungers. The plungers have an orientation corresponding to the orientation of sample tube positions in a sample tube holder. The plungers are separately retractable and separately protractible with respect to the housing, and each of the plungers have an end portion with a sample tube engagement surface that extends outwardly of the housing. Biasing means are associated with each of said plungers to separately urge the plungers into a first protracted position wherein the sample tube engagement surface of each plunger is a first predetermined distance from said housing. The protracted position of the plunger is correlatable with a broken sample tube in the corresponding sample tube position of the sample tube holder or a tubeless position in the corresponding sample tube position of the sample tube holder. The plungers are also separately movable against the force of the respective biasing means to a retracted position wherein the tube engagement surface is moved a predetermined amount toward the housing. The retracted position of each plunger is correlatable with an unbroken sample tube in the corresponding sample tube position of the sample tube holder.

The sample tube breakage detector also includes detection means in the housing cooperable with each of the plungers to detect the protracted or retracted position of the respective plungers before and after a centrifuge spin operation of the sample tube holder with sample tube. Thus a comparison of the protracted or retracted plunger positions detected by the detection means before and after the centrifuge spin operation of sample tubes in the sample tube holder permits determination of whether a sample tube, previously detected in an unbroken condition in the sample tube holder before the centrifuge spin operation, has suffered breakage after the centrifuge spin operation.

The invention further includes a gripper device for gripping the sample tube holder, which gripper device cooperates with the sample tube breakage detector. The gripper device can be incorporated with the sample tube breakage detector structure as an integral part of the sample tube breakage detector, and includes an elongated lifting probe depending from the housing of the sample tube breakage detector proximate one side of the housing. The lifting probe includes a fixed post having a first axis, and a gripper portion at a lower end of the post, away from the housing. The gripper portion has a second axis, and is movable with respect to the post from an axially aligned position with the post, wherein the second axis of the gripper portion and the first axis of the post are axially aligned, to an axially eccentric engagement position, wherein the second axis of the gripper portion is offset from the first axis of the post to permit engagement of the gripper portion against a portion of a sample tube holder such that the sample tube holder is held by the lifting probe. Stabilizing means are also provided on the housing for stabilizing the sample tube holder during lifting engagement of the sample tube holder by the lifting probe.

The invention additionally includes a device for raising and lowering an object such as the sample tube breakage detector and the sample tube holder that is gripped by the sample tube breakage detector. The raising and lowering device includes a base and first and second telescoping members movable with respect to the base. The second telescoping member is movable to extended and retracted positions with respect to the first telescoping member. First drive means are mounted to the base and joined to the first telescoping member to move the first telescoping member in opposite directions with respect to the base. Second drive means are mounted on the first telescoping member and are joined to the second telescoping member to move the second telescoping member in opposite directions with respect to the first telescoping member and the base.

The invention accordingly comprises the constructions and methods hereinafter described, the scope of the invention being indicated in the claims.

DESCRIPTION OF THE DRAWINGS

In the drawings,

FIG. 50 is a perspective view of one of the two similar end sections of the sample tube bucket;

FIG. 51 is a front elevational view of the opposite side of the sample tube bucket end section shown in FIG. 50;

FIG. 52 is a top plan view of the bucket end section;

FIG. 53 is a perspective view of one of the two bucket leaf springs for each sample tube receiving opening in the sample tube bucket;

Corresponding reference numbers indicate corresponding parts throughout the several views of the drawings.

DETAILED DESCRIPTION

Figure 1:
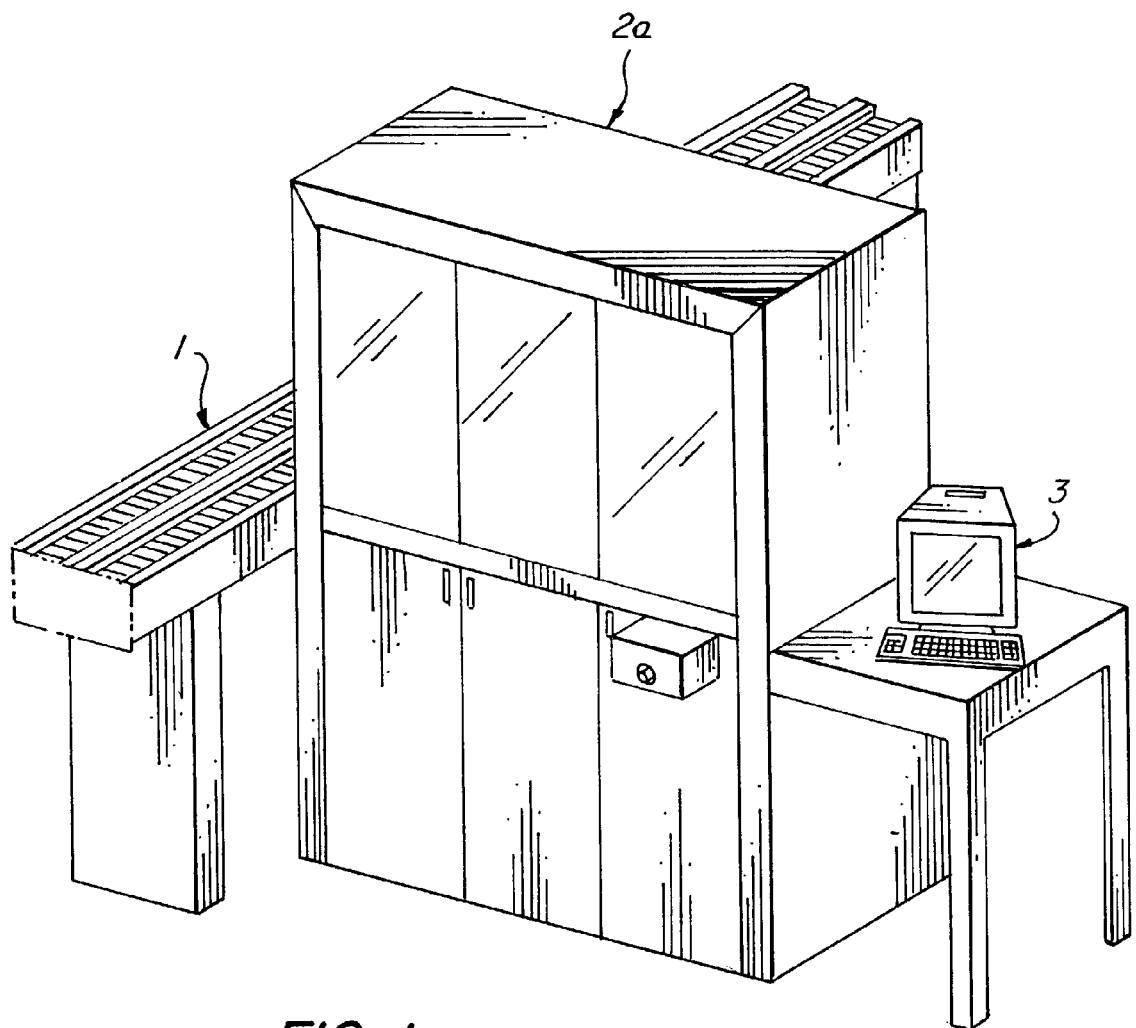
FIG. 1 is a simplified perspective view of the lab cell centrifuging module cabinetry, and a main conveyor schematically shown alongside the module for bringing sample tubes to the module and taking sample tubes away from the module.
Figure 2:
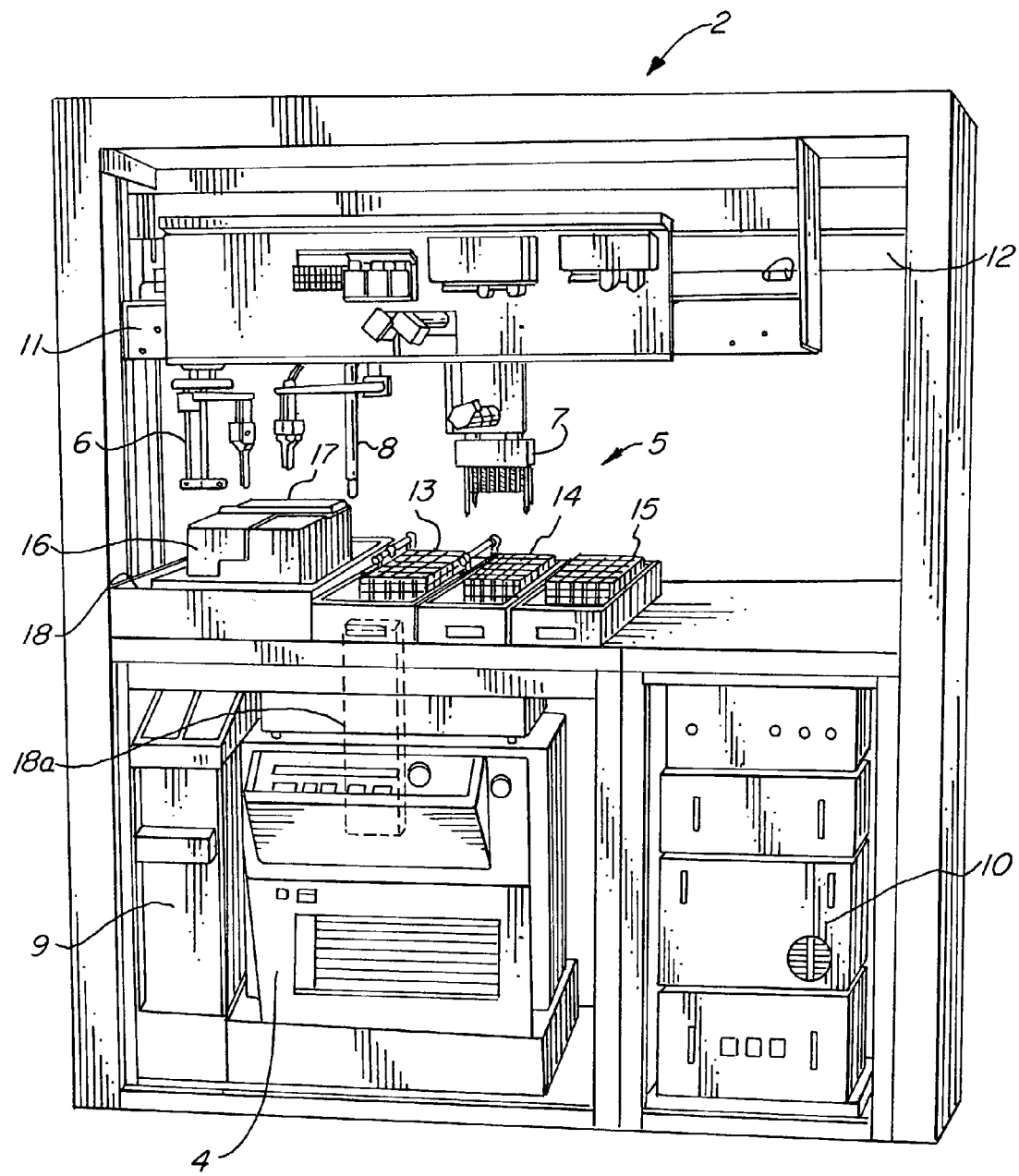
FIG. 2 is a simplified perspective view of the module of FIG. 1 with the cabinet doors removed to show the general components of the module, including a centrifuge on the lower left and electronic power and control devices on the lower right.

Referring to the drawings, FIG. 1 shows a main conveyor 1 of the type disclosed in U.S. Pat. No. 6,374,989 for A Conveyor System For A Clinical Test Apparatus, which is incorporated by reference herein. FIG. 1 also shows a six door housing 2a for the lab cell centrifuging module 2 (FIG. 2). The conveyor 1 is not part of the lab cell centrifuging module 2.

FIG. 2 shows a centrifuge 4 which is preferably a standard off-the-shelf centrifuge device, a tabletop assembly 5 operated by three robots which include a sample tube gripper robot 6, a bucket gripper robot 7 and a sample tube delivery robot 8. The robots 6 and 8, which pick individual sample tubes, each have the same type of pneumatic fingers 6a and 8a (FIG. 3) that open and close in parallel relationship. A waste collection bin 9 (FIG. 2) receives caps from decapped sample tubes. A robot control cabinet 10 (FIG. 2) includes the computers, electronics and power supplies for the lab cell centrifuging module 2.

The robots 6, 7 and 8 (FIG. 2) are mounted on cross beams 11 and 12, across the tabletop assembly 5. Further details of the robots 6, 7 and 8 and the robot mounting structure for mounting the robots 6, 7 and 8 on the beams 11 and 12 are disclosed in U.S. Pat. No. 6,293,750 for Robotics For Transporting Containers And Objects Within An Automated Analytical Instrument and Service Tool For Servicing Robotics, which is incorporated by reference herein.

The sample tube gripper robot 6 and bucket gripper robot 7 (FIG. 3) are commonly mounted on the beam 11, which defines a front side of the module 2. The sample tube delivery robot 8 is mounted on the beam 12 (FIG. 3).

Figure 3:
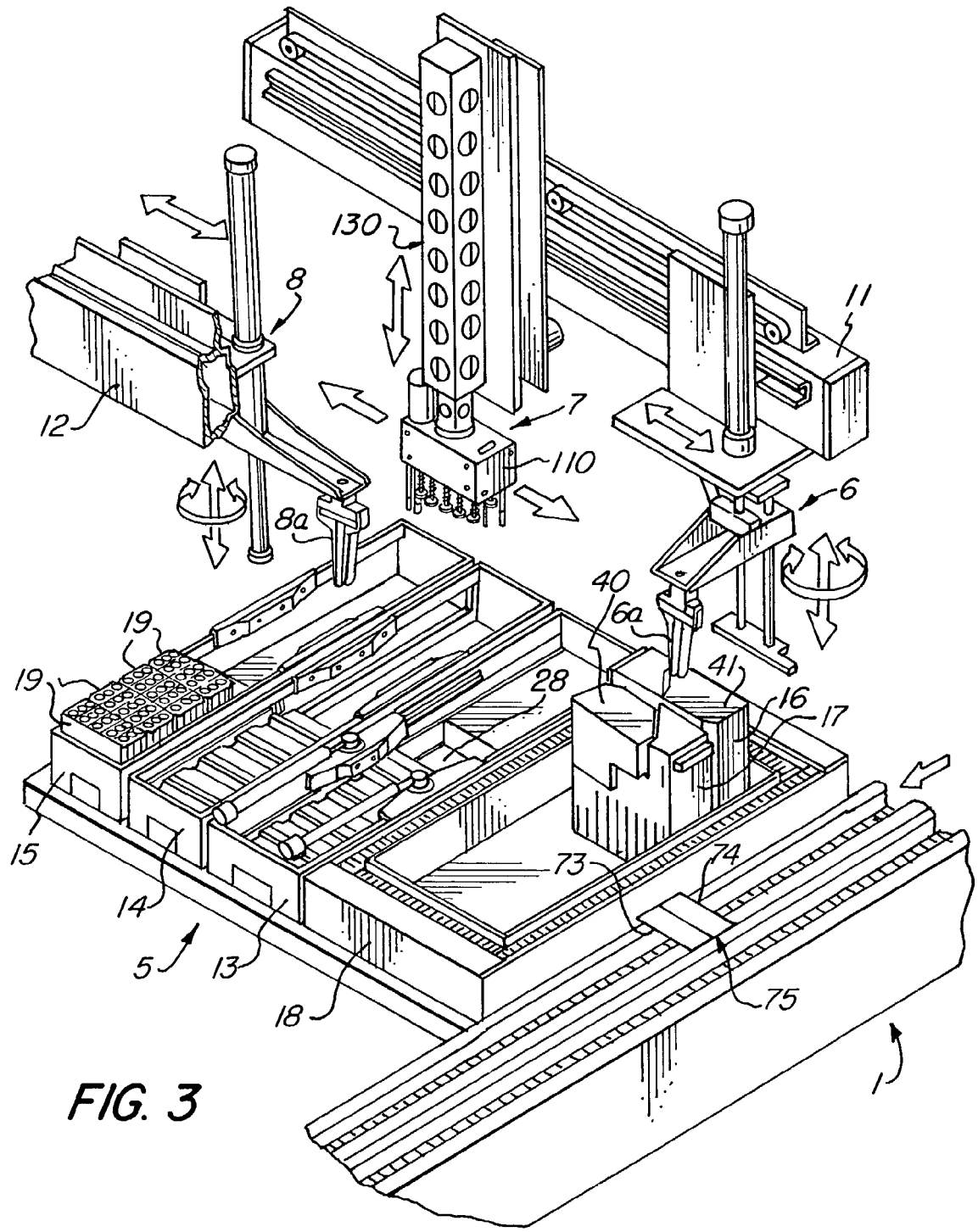
FIG. 3 is a simplified top perspective view of tabletop components of the module including two load queues, an unload queue, two decappers positioned within the confines of a rectangular path conveyor, a sample tube gripper robot and a bucket gripper robot on one cross beam, and a sample tube delivery robot on another cross beam, and an external conveyor alongside the module.
Figure 7:
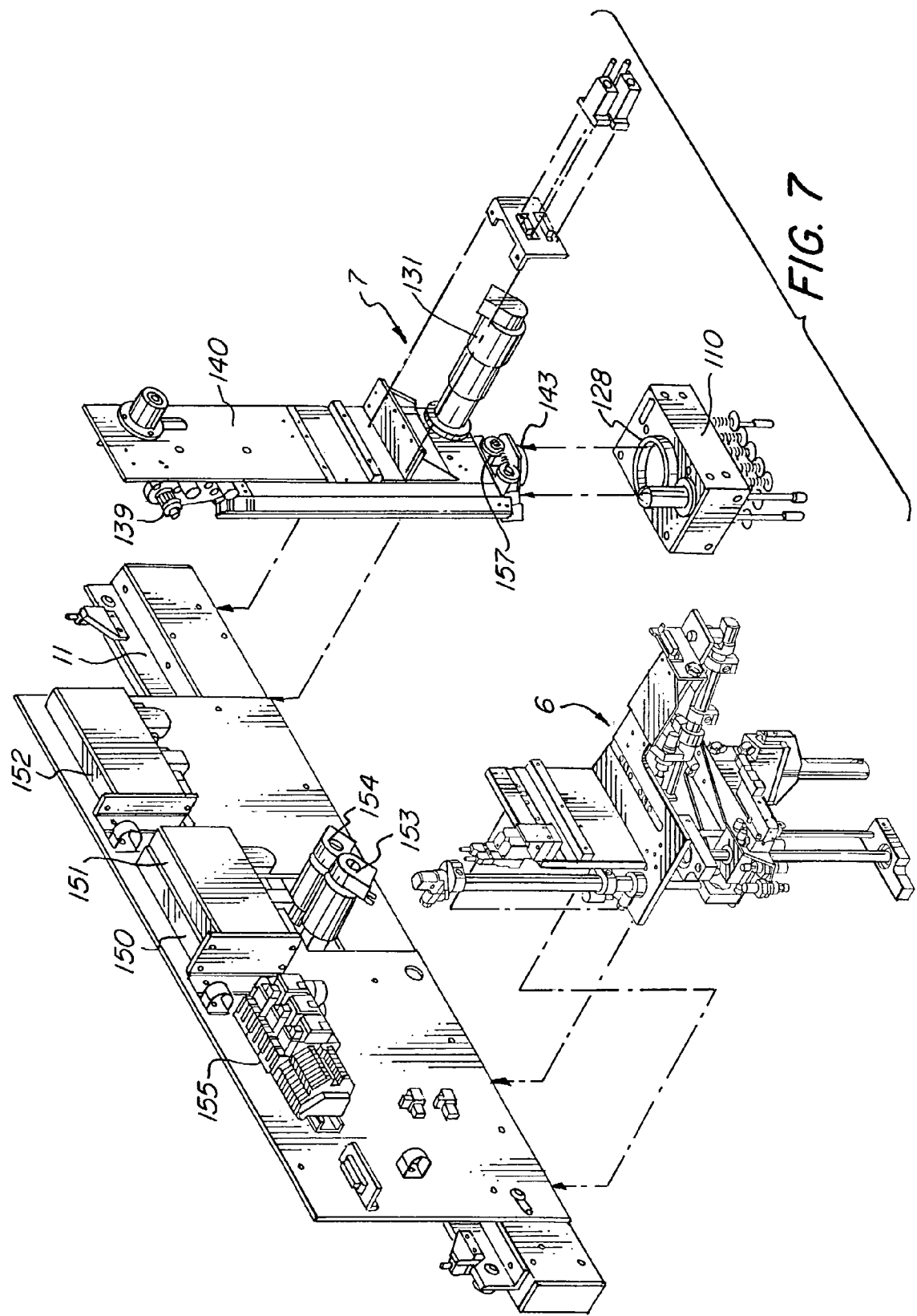
FIG. 7 is a fragmentary perspective view, partially exploded, of the back side of the cross beam that supports the sample tube gripper robot and the bucket gripper robot.
Figure 8:
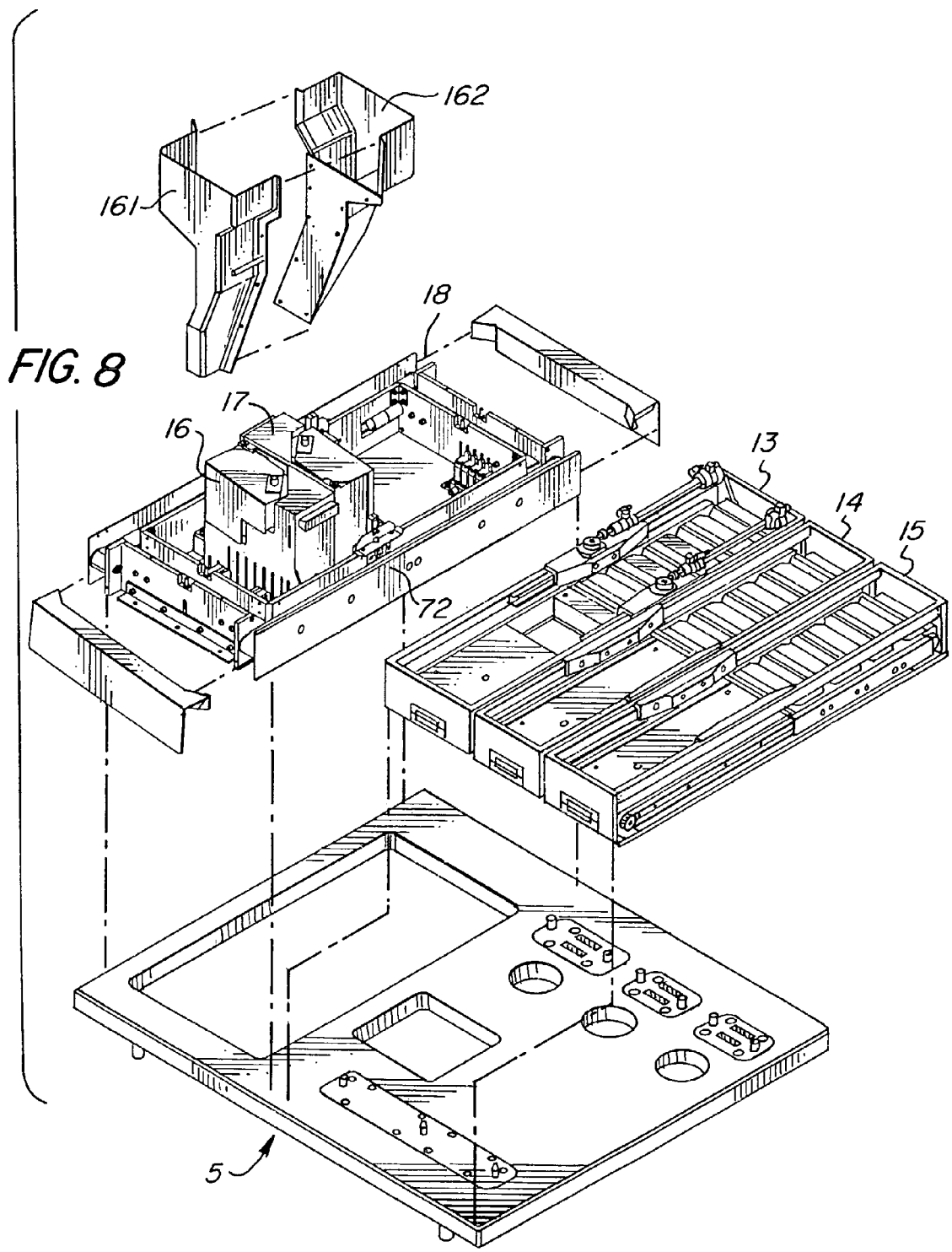
FIG. 8 is a fragmentary perspective view, partially exploded of the tabletop structure of FIG. 3, with two disposal chutes normally underneath the decappers for receiving caps expelled from the decappers.

Three component boxes shown schematically and labeled 150, 151, 152 in FIG. 7 are known electronic motion controllers that control the drives 153, 154 and 131 corresponding to movement of the sample tube gripper robot 6 in the "x" direction, movement of the bucket gripper robot 7 in the "x" direction and movement of the bucket gripper robot 7 in the "z" direction (FIG. 3). "Z" and "y" movement of the sample tube gripper robot 6 are pneumatically actuated.

Figure 11:
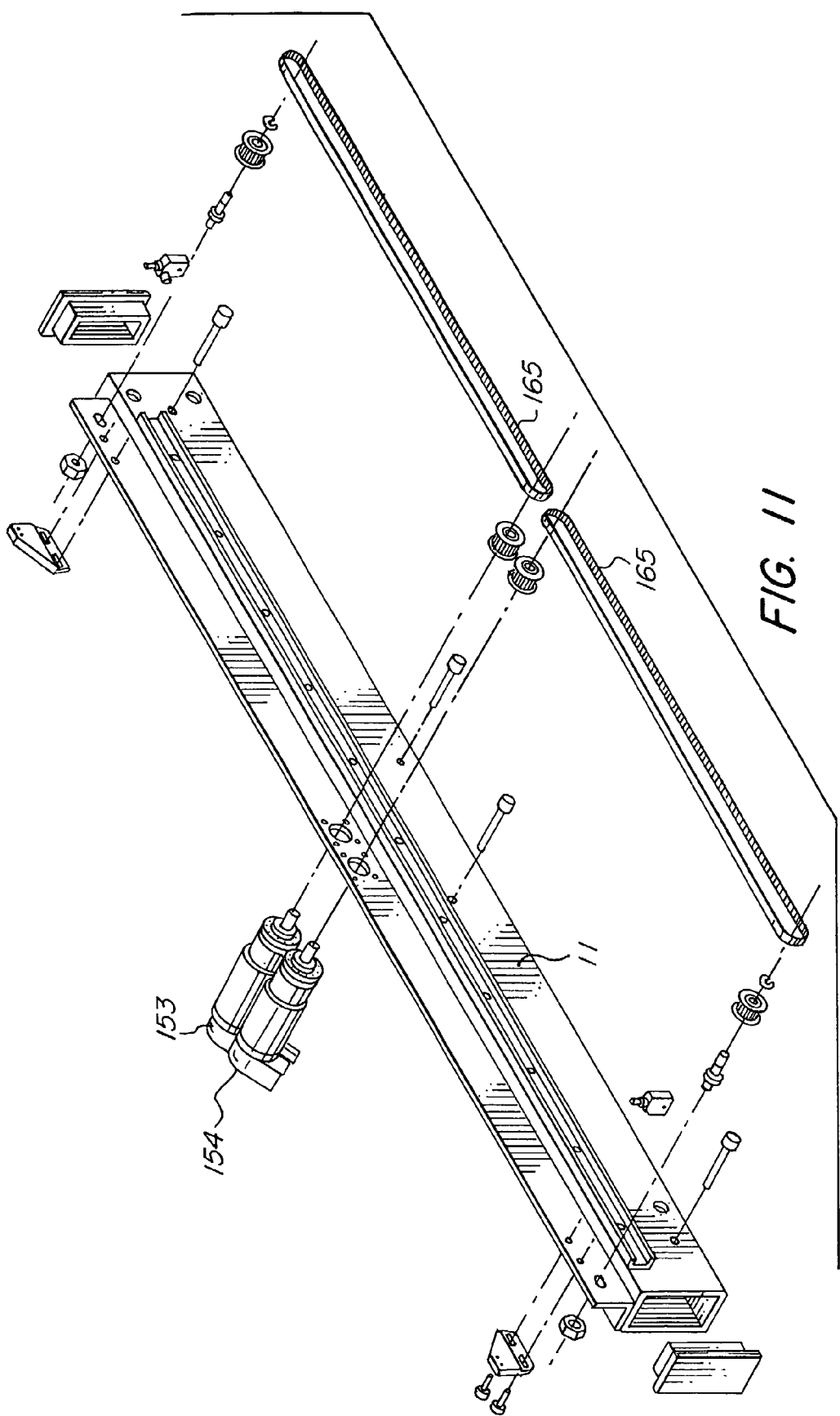
FIG. 11 is an exploded perspective view of the support beam shown in FIG. 3 for the sample tube gripper robot and the bucket gripper robot.
Figures 12, 13:
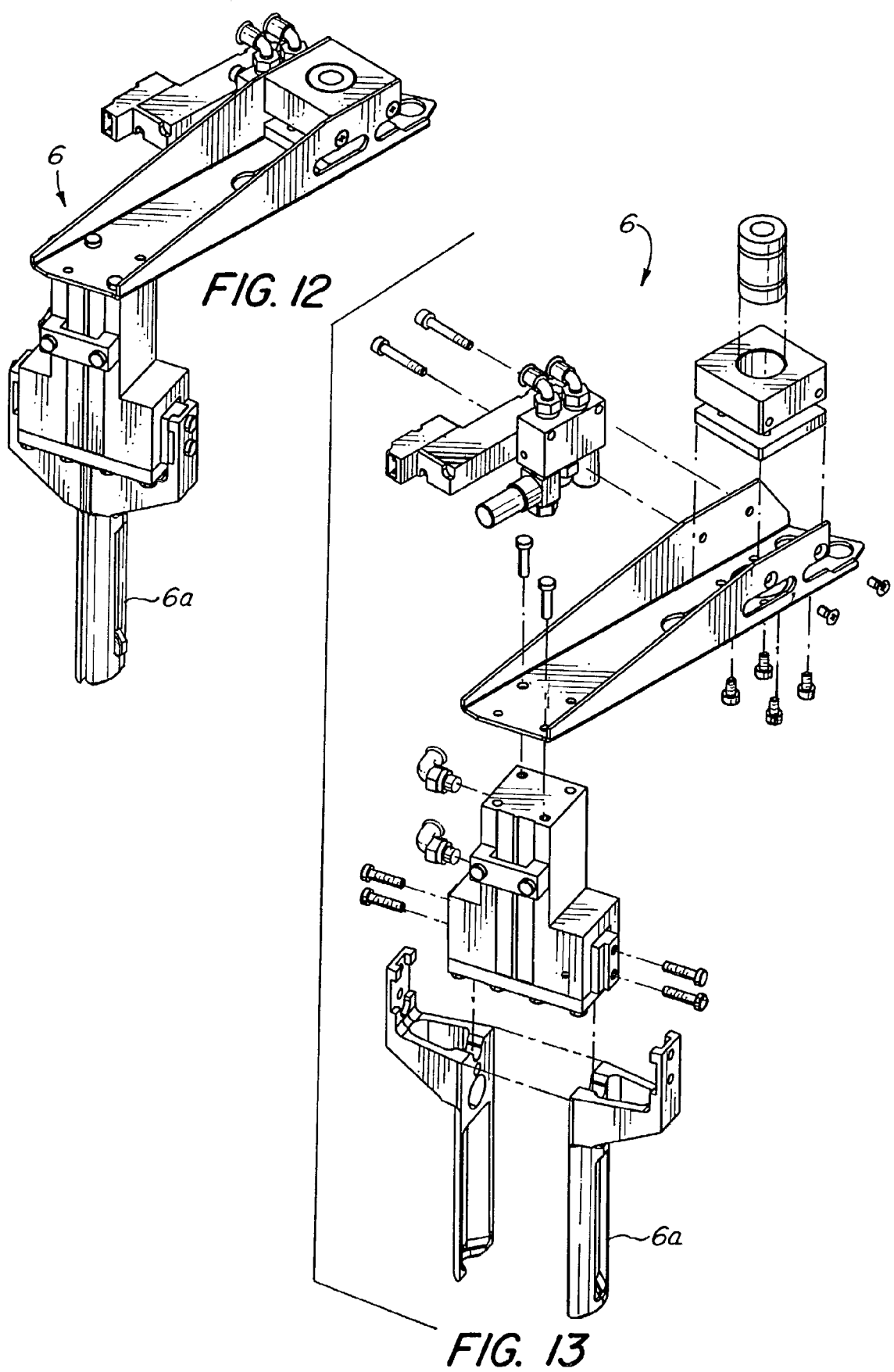
FIG. 12 is a perspective view of the sample tube gripper robot fingers and the robot finger support structure.
FIG. 13 is an exploded view of the structure shown in FIG. 12.
Figure 14:
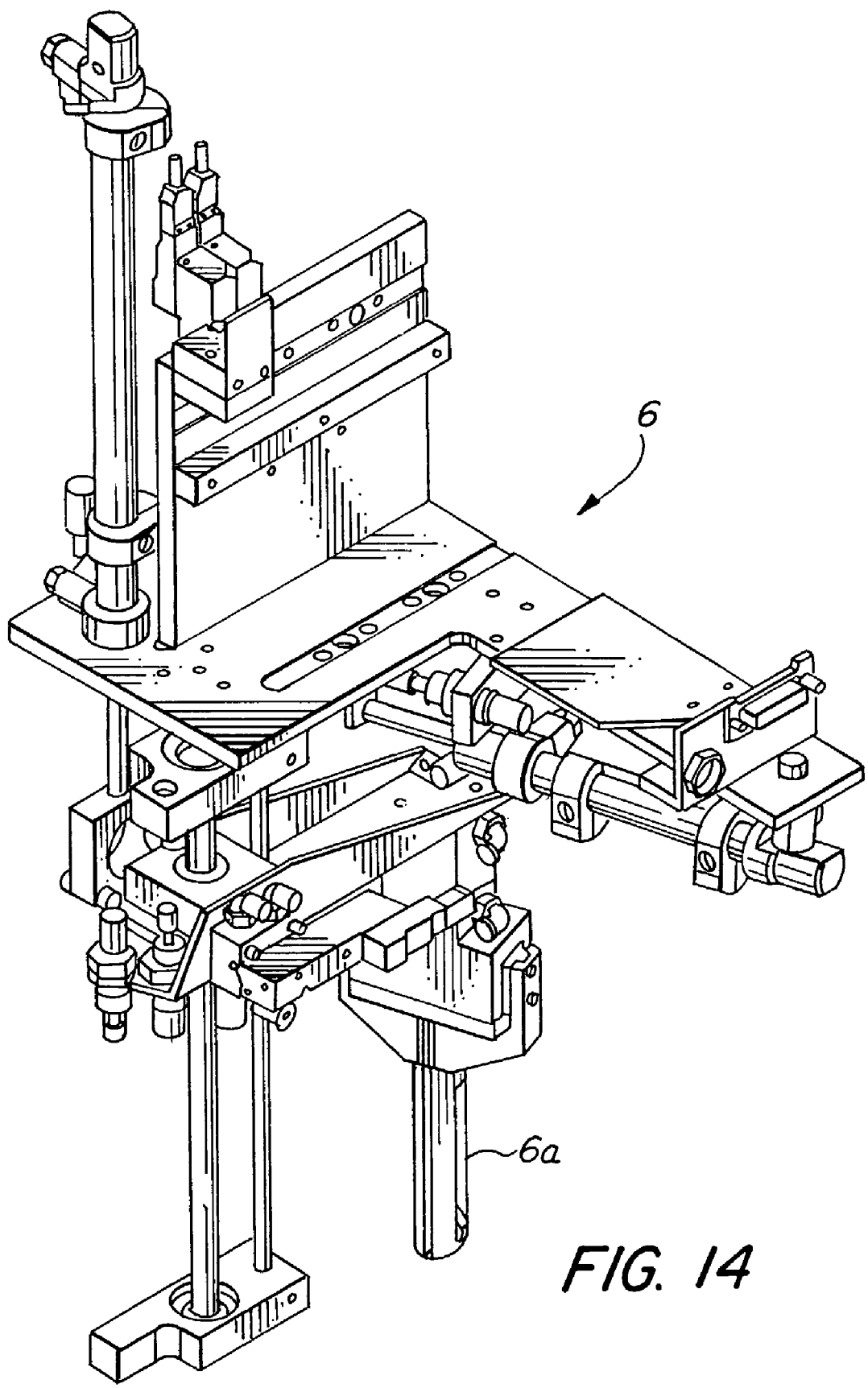
FIG. 14 is an enlarged perspective view of the sample tube gripper robot shown in FIG. 7.

FIG. 11 shows the beam 11 for the sample tube gripper robot 6 and the bucket gripper robot 7, with "x" drives 153, 154 for the robots 6 and 7, and respective robot drive belts 165, 165. Each of the robot drive belts 165 has its own "x" drive 153, 154.

The tabletop assembly 5 (FIGS. 2, 3, 4 and 8) contains three queues, which include an unloading queue 13 and two loading queues 14 and 15. The two loading queues 14 and 15 are the same. In addition there are two similar decappers 16 and 17 (FIGS. 2-4) and a relatively small rectangular path conveyor 18 (FIGS. 3-4) where sample tubes move around the decapper 16, 17 within the lab cell centrifuging module 2. Thus the conveyor 18 which is part of the lab cell centrifuging module 2 is distinct and separate from the main conveyor 1 which is not part of the module 2.

Since the lab cell centrifuging module 2 has the moving robots 6, 7 and 8 the upper doors of the housing 2a (FIG. 1) for user access to the module are normally locked as a safety measure. As a further safety measure when any of the upper doors are opened the power to the unit is shut off via safety relays 155 (FIG. 7). Robot movement is thus shut down for operator safety.

FIG. 2 also shows a centrifuge access path 18*a* in dotted outline. The access path 18*a* defines the "z" path of the bucket gripper robot 7 as it moves into and out of the centrifuge 4. FIG. 3 includes a top perspective view of the tabletop assembly 5, the robots 6, 7 and 8 and the main conveyor 1.

The tube gripper robot 6 moves in three axes—"x" and "z", and also pivots a small amount about the "z" axis, as shown in FIG. 3, to accomplish a "y" shift. The bucket gripper robot 7 (FIG. 3) moves only in the "z" and "x" axes. The sample tube delivery robot 8 (FIG. 3) moves in all three directions "x" and "z" and pivots about the "z" axis to accomplish a "y" shift.

The tabletop assembly 5 (FIG. 3) includes the unloading queue 13, the two loading queues 14, 15, the internal conveyor 18 and the two decappers 16 and 17. All three robots 6, 7 and 8 and all three robot movements are programmed so as not to interfere with one another.

An interface gate 75, shown schematically in FIG. 3, is of the type shown in the previously referred to U.S. Pat. No. 6,374,989 and is employed on the conveyor 1. The interface gate 75 is a wheel (not shown) with four positions. When a sample tube on the conveyor 1 arrives at the gate 75 the wheel turns 90 degrees and brings the sample tube (not shown) into a known position accessible by the sample tube delivery robot 8. The sample tube delivery robot 8 is programmed to stop at a sample tube access position also referred to as the pick position 74.

A puck 54 (FIG. 4) of the type shown in U.S. Pat. No. 5,897,090 for Puck For Sample tube, which is incorporated herein by reference, is a small container that holds sample tubes that are transported on the conveyors 18 and 1. Incoming sample tubes on the conveyor 1 (FIGS. 3 and 4) are stopped at the interface gate 75. The interface gate turns 90 degrees to place individual sample tubes in the pick position 74 (FIG. 3). The sample tube delivery robot 8 can access the pick position 74 (FIG. 3) and is notified by system software that there is a sample tube in the pick position 74.

The sample tube delivery robot 8 thus moves to the pick position 74, picks the sample tube and moves the sample tube to one of the available loading queues 14 or 15 (FIG. 3) which hold sample tube carriers or buckets 19 for the centrifuge 4. The sample tube bucket 19 is also referred to as a centrifuge bucket (FIG. 37) and is essentially a container or holder with sample tube receiving openings that can hold up to 15 sample tubes in a 3×5 matrix.

The sample tube delivery robot 8 thus picks a sample tube in the interface gate 75 on the conveyor 1 (FIGS. 3 and 4), moves that sample tube into one of the loading queues, either 14 or 15, and then into one of the tube positions in the sample tube bucket 19. Each of the loading queues 14, 15 is configured with four sample tube buckets 19. The loading queues 14 and 15 thus provide a space for 4 buckets×15 sample tubes or sixty sample tubes per four bucket batch (FIG. 4).

The system software determines when a loading queue 14 and 15 is interpreted as full—so it is not necessary to have all sixty sample tubes loaded into the four sample tube buckets 19 in the loading queues 14 and 15 to trigger a removal of the bucket 19 from the loading queue 14 and 15 to the centrifuge 4. Thus the centrifuge process is based on a time limit rather than a quantity of sample tubes in a sample tube bucket 19.

A desired throughput for the lab cell centrifuging module 2 is to spin three hundred sample tubes per hour. If there are sixty sample tubes maximum per four bucket batch and five four bucket batches are spun per hour, the result is 5 spin cycles×60 sample tubes per 4 bucket spin cycle=300 spun sample tubes. Thus each four bucket batch has a programmed cycle time of approximately twelve minutes (sixty minutes divided by five batches results in twelve minutes per batch). These twelve minutes include the pure spin time and the time to load the buckets with sample tubes and unload the spun sample tubes from the sample tube buckets for decapping. The twelve minute cycle time is user configurable, not fixed. But once the cycle time is established the default is after twelve minutes and the loading queue is interpreted as ready to go to the centrifuge 4 whether or not all sample tube buckets 19 in the loading queue 14 and 15 are filled with sample tubes.

Figure 4:
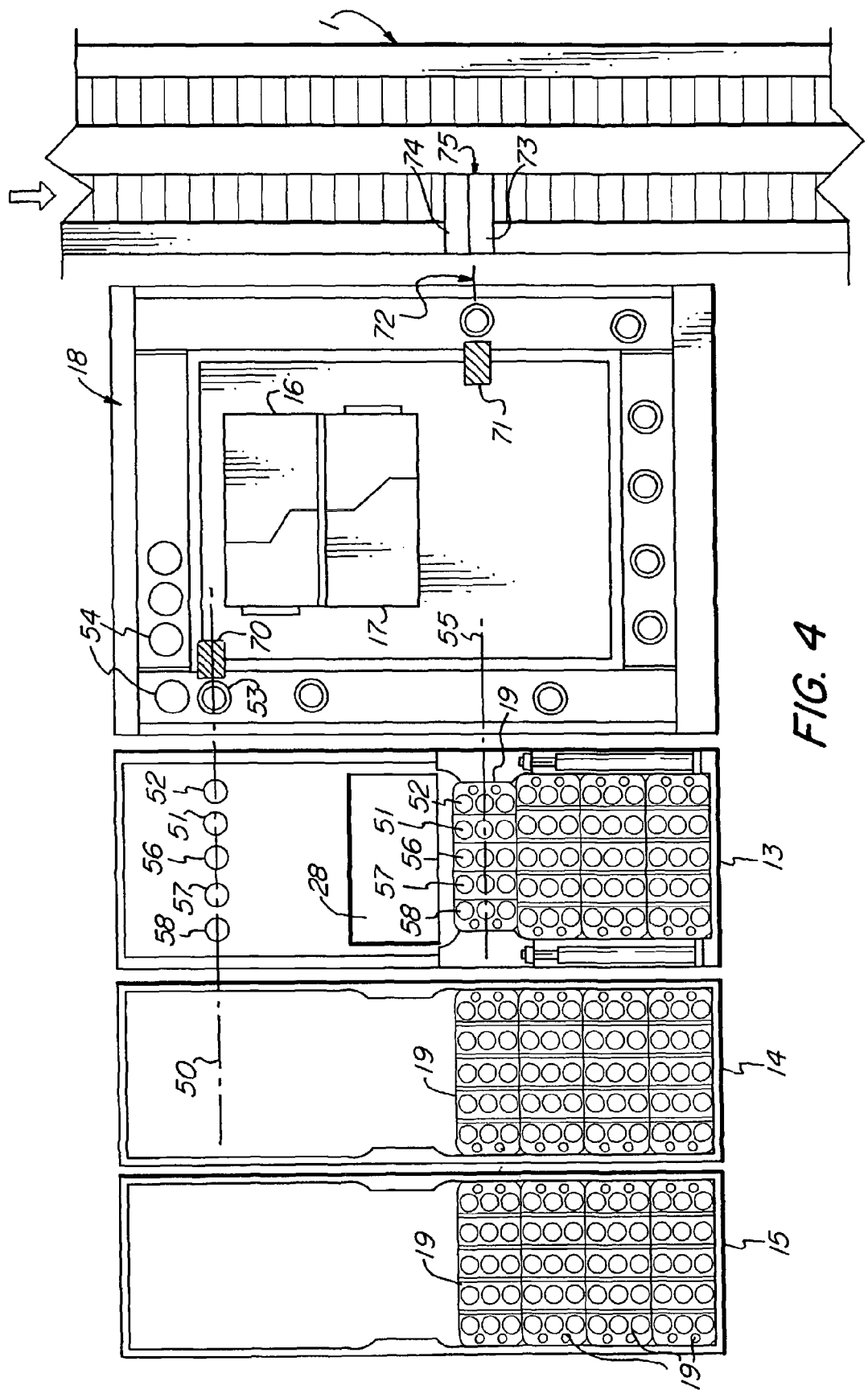
FIG. 4 is a simplified plan view of the tabletop components shown in FIG. 3, and the external conveyor.
Figure 35:
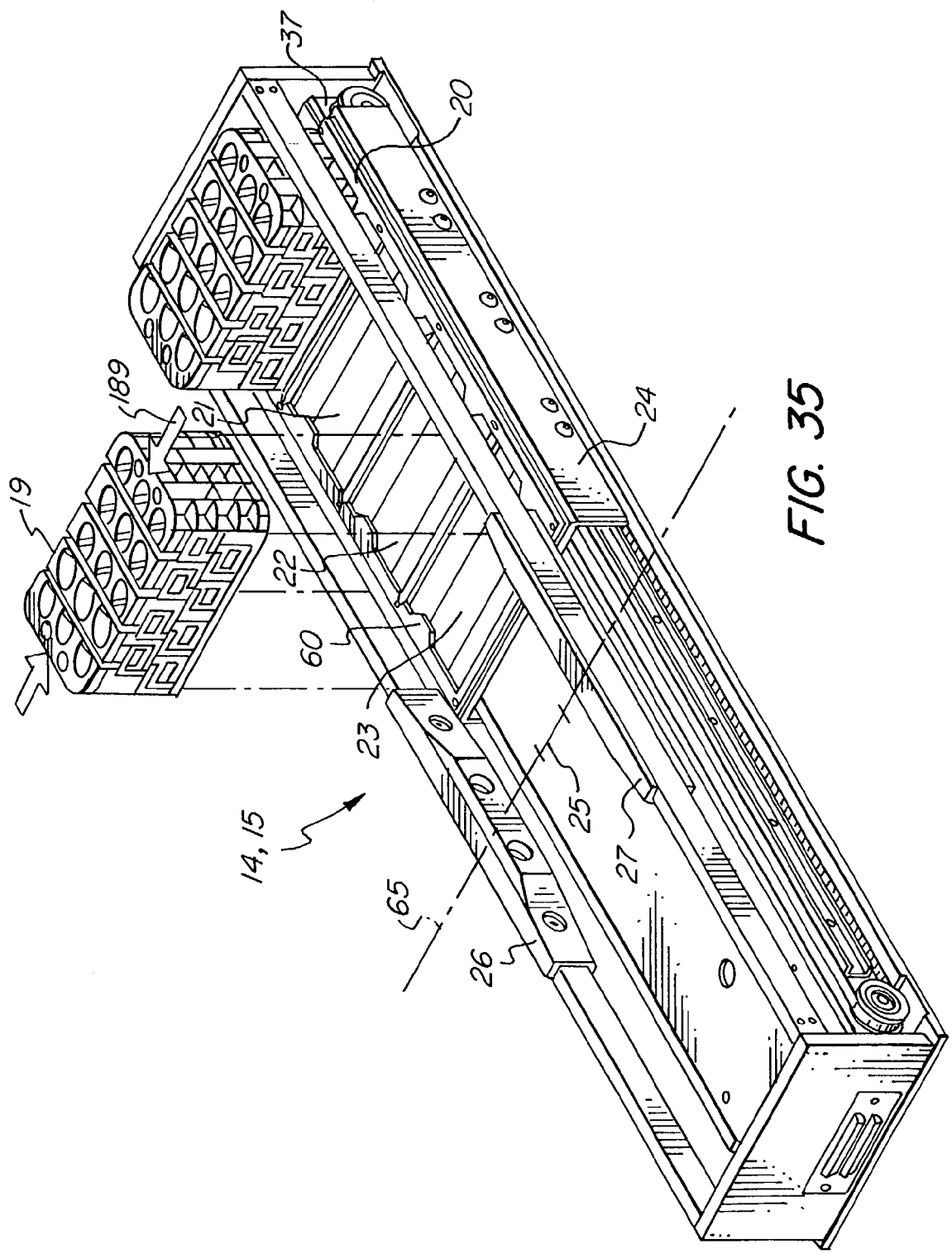
FIG. 35 is a perspective view of one of two similar loading queues from the tabletop components of FIGS. 2-5 and 8, with one sample tube bucket on the loading queue in a home position, and one sample tube bucket in an elevated unloaded position prior to being compressed from a normally expanded condition.
Figure 36:
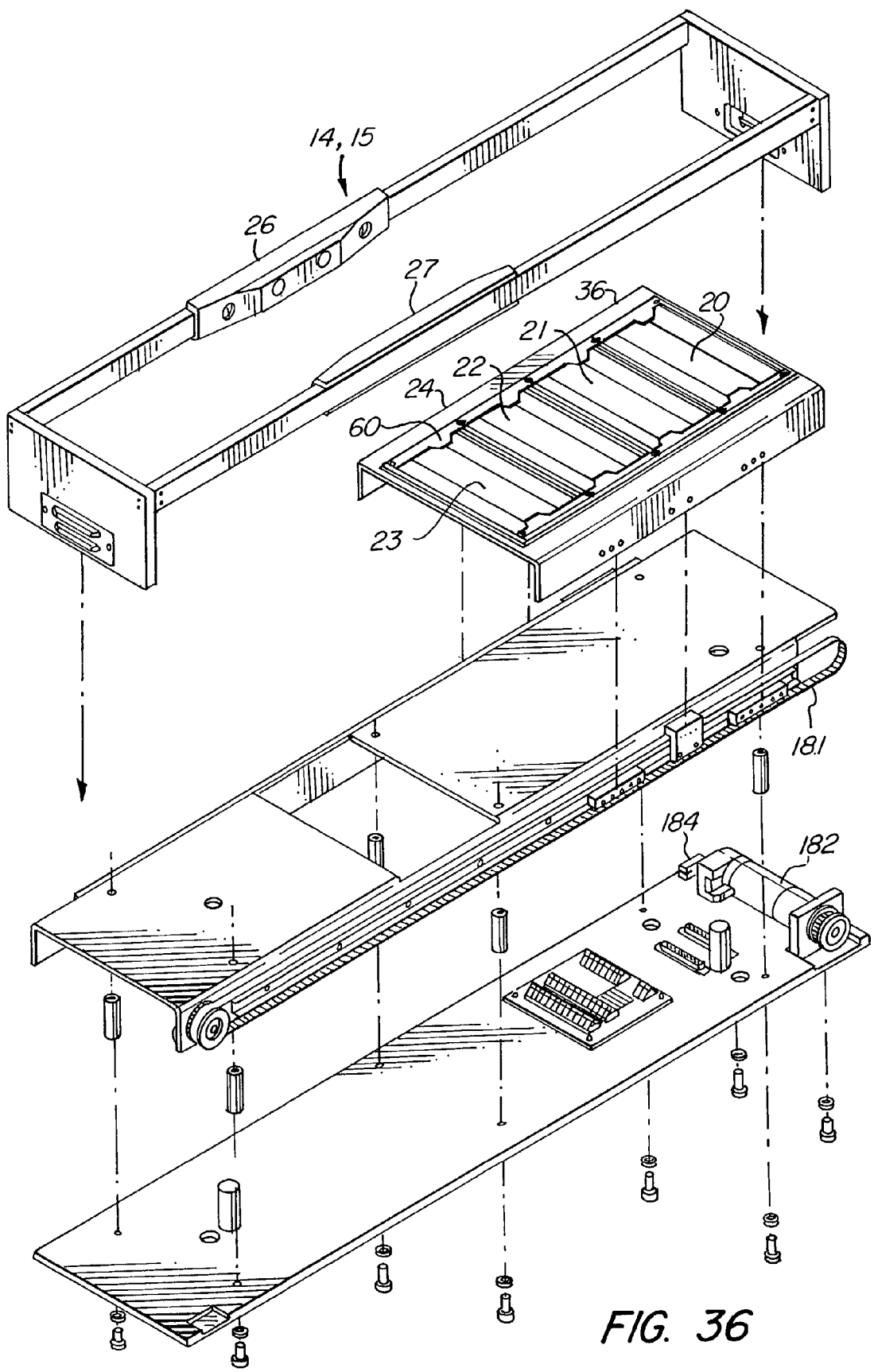
FIG. 36 is a partially exploded perspective view of the loading queue shown in FIG. 35.

For discussion purposes it can be assumed at startup that the centrifuge 4 is currently empty and that all sample tube buckets 19 in the three queues 13, 14 and 15 are in the position shown in FIG. 4. The loading queues 14 and 15 (FIG. 4) each contain four empty sample tube buckets 19 and the unloading queue 13 contains four empty sample tube buckets 19. The four bucket positions on a slide carriage 24 in the loading queues 14, 15 are marked 20, 21, 22 and 23 (FIGS. 35 and 36).

The sample tube delivery robot 8 (FIG. 3) moves individual capped sample tubes from a pick position 74 on the interface gate 75 of the conveyor section 1 to the sample tube buckets 19 on the load queue 14, for example. Ideally all four sample tube buckets 19 on the load queue 14 will be filled with capped sample tubes by the sample tube delivery robot 8. However, sample tube buckets 19 that are in the position on the load queue 14 as shown in FIG. 4 are not accessible by the bucket gripper robot 7 or the sample tube gripper robot 6. Therefore the slide carriage 24 on the load queue 14 must move the sample tube buckets 19 from the home position 37 (FIG. 35) of the slide carriage 24 in a direction toward the opposite end of the load queue 14.

Figure 37:
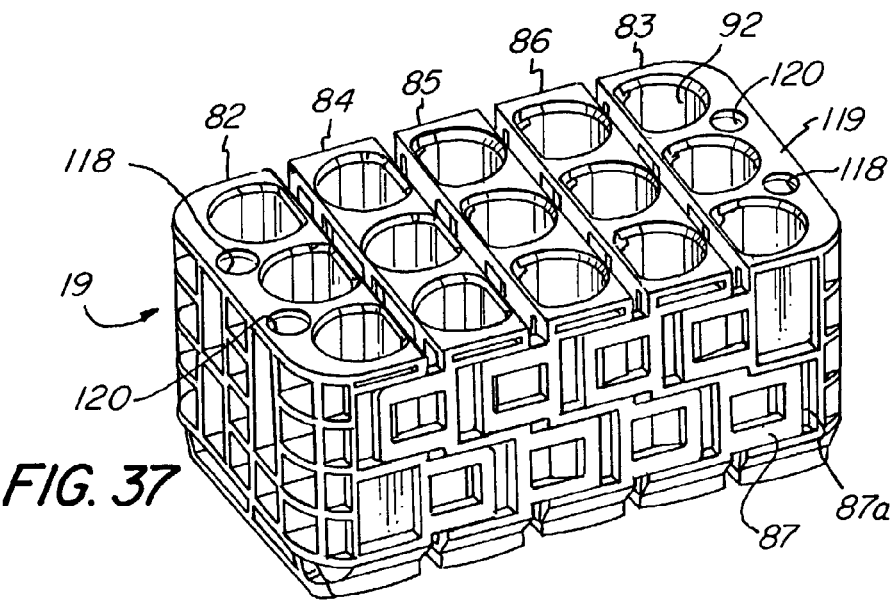
FIG. 37 is a perspective view of the sample tube bucket in its normally expanded condition.

The sample tube bucket position 23 is thus aligned with the bucket deflectors 26 and 27 (FIG. 35) that compress the normally expanded sample tube bucket 19 (FIG. 37). The space on the load queue 14 between the bucket deflectors 26 and 27 also define a bucket pick position 25 (FIG. 35) which is accessible by the bucket gripper robot 7, which moves along an access path 65 in the "x" direction. Thus the bucket gripper robot 7 moves over the compressed sample tube bucket 19, moves down to engage the bucket 19, picks the bucket 19 and moves over along the access path 65 on top of the centrifuge 4. There is an open lid for the centrifuge 4, and the bucket gripper 7 with a bucket 19 moves down into the centrifuge 4 below the tabletop 5 through an opening 28 (FIG. 3) in the unloading queue 13.

Inside the centrifuge 4 are four bucket receiving positions in a cross pattern (not shown). Thus when the first sample tube bucket 19 is deposited into the centrifuge 4 the system software triggers that event and the centrifuge bucket receiving cross pattern rotates 90 degrees. The bucket gripper 7 moves back to the loading queue 14 to the deflector position of the deflectors 26, 27. Meanwhile the loading queue slide carriage 24 has moved to place the next bucket position, such as the position 22, into the bucket pick position 25 (FIG. 35) between the two deflectors 26 and 27 so that the bucket gripper 7 can access it.

The bucket gripper 7 (FIG. 3) picks the bucket from the position 22 (FIG. 35) moves it into the centrifuge opening 28 (FIG. 3) moves it down into the centrifuge 4 and comes back up. The bucket receiving cross pattern in the centrifuge 4 rotates 90 degrees. That happens four times until all four buckets 19 from all four positions 20, 21, 22 and 23 of the loading queue 14 (FIG. 4) are inside the centrifuge 4.

The centrifuge is filled to capacity when it contains four of the sample tube buckets 19 in a cross pattern.

It should be noted that the centrifuge 4 has a top cover with a lid (not shown). The centrifuge software triggers that lid to close when the centrifuge is loaded with four sample tube buckets 19 before the spinning operation begins. The centrifuge lid must be closed during spinning because there is a refrigerating capability inside the centrifuge, and also for safety purposes because of the high speed rotating devices.

During the described bucket transfer process from one of the loading queues 14 to the centrifuge 4 by the bucket gripper robot 7, the sample tube delivery robot 8 will continue to load sample tubes into the other loading queue 15. Therefore, one of the two loading queues 14, 15 is always available for the sample tube delivery robot 8. As a result when one batch of four sample tube buckets 19 is spinning in the centrifuge 4, one of the loading queues 14, 15 is being loaded by the sample tube delivery robot 8, which transfers capped sample tubes from the conveyor 1 to a selected loading queue.

The sample tube delivery robot 8, independently of the robots 6 and 7, loads capped sample tubes from the interface gate 75 on the conveyor 1 (FIG. 3) by picking sample tubes from the pick position 74 of the interface gate 75 (FIG. 3) and moving them into sample tube buckets 19 in the available loading queue 14 or 15. Meanwhile the centrifuge 4 spins. Thus there is simultaneous activity.

Centrifuge spin time is a selectable parameter of the system software that depends on the type of sample being spun. Spin time varies from urine to blood to whole blood to whatever body fluid is being spun. The lab cell centrifuging module 2 can be used not only for blood but for other types of body fluid and the spin time is a matter of choice, such as eight minutes or twelve minutes, for example. A predetermined spin time is specified to calculate the throughput of the system.

Figure 32:
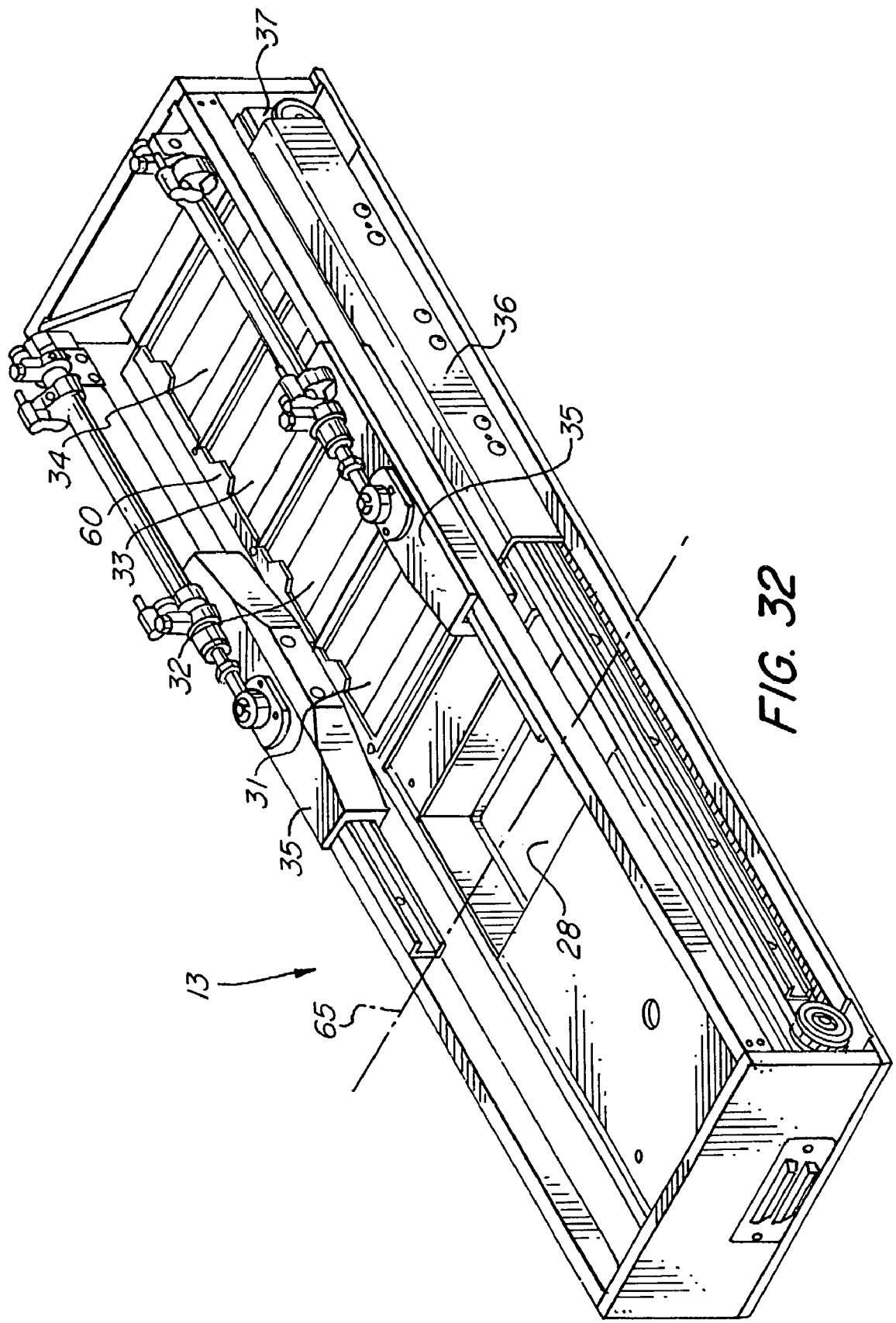
FIG. 32 is a perspective view of the unloading queue, from the table top components of FIGS. 2-5 and 8.

After the centrifuge spin cycle is completed the centrifuge lid opens again, the bucket gripper robot 7 moves down into the centrifuge 4 along the path 18a (FIG. 2), picks a sample tube bucket 19 from the centrifuge 4 and moves it up through the opening 28 in the unloading queue 13 (FIGS. 3 and 32).

The unloading queue 13 (FIG. 32) also has four bucket positions 31, 32, 33 and 34 on a slide carriage 36, similar to the slide carriage 24 of the loading queues 14, 15. The unloading queue 13 (FIG. 32) also has a bucket compressing device or mobile deflector 35.

After the bucket gripper 7 picks a sample tube bucket 19 from inside the centrifuge 4 and moves the bucket up through the opening 28 in the unloading queue 13 the slide carriage 36 (FIGS. 3, 4 and 32) moves over the opening 28. The mobile deflector 35 also moves simultaneously to a position just over the opening 28 that is now covered by the slide carriage 36. The bucket gripper robot 7 will then move down to place the sample tube bucket 19 at the position 31 on the slide carriage 36 (FIG. 32).

Position 31 is now just over the opening 28 that is covered by the slide carriage 36 and in between the two mobile deflectors 35.

The bucket gripper robot 7 releases the sample tube bucket 19 into the bucket position 31 and moves back up. Then the slide carriage 36 and the mobile deflector 35 move back to the home position 37 as shown in FIG. 32. When the slide carriage 36 and the mobile deflectors 35 are in the home position 37 the opening 28 to the centrifuge is once again uncovered.

Meanwhile the centrifuge bucket receiving cross (not shown) rotates 90 degrees and moves the next bucket 19 of spun sample tubes into the bucket pick position inside the centrifuge 4. The bucket gripper robot 7 moves down through the centrifuge opening 28 in the unloading queue 13 into the centrifuge 4, picks the next spun sample tube bucket 19, moves up and the same cycle is repeated. The slide carriage 36 of the unloading queue 13 (FIG. 32) moves over the centrifuge opening 28, the mobile deflector 35 moves together with the slide carriage 36 over the centrifuge opening 28, the bucket gripper 7 (FIG. 3) moves down puts the sample tube bucket 19 in the second bucket position 32 (FIG. 32) on the slide carriage 36, which is now just over the opening 28, releases the bucket 19 and moves up. And the bucket removal process from the centrifuge 4 continues until all four spun sample tube buckets 19 are removed and positioned on the unloading queue 13 (FIG. 4).

Figure 5:
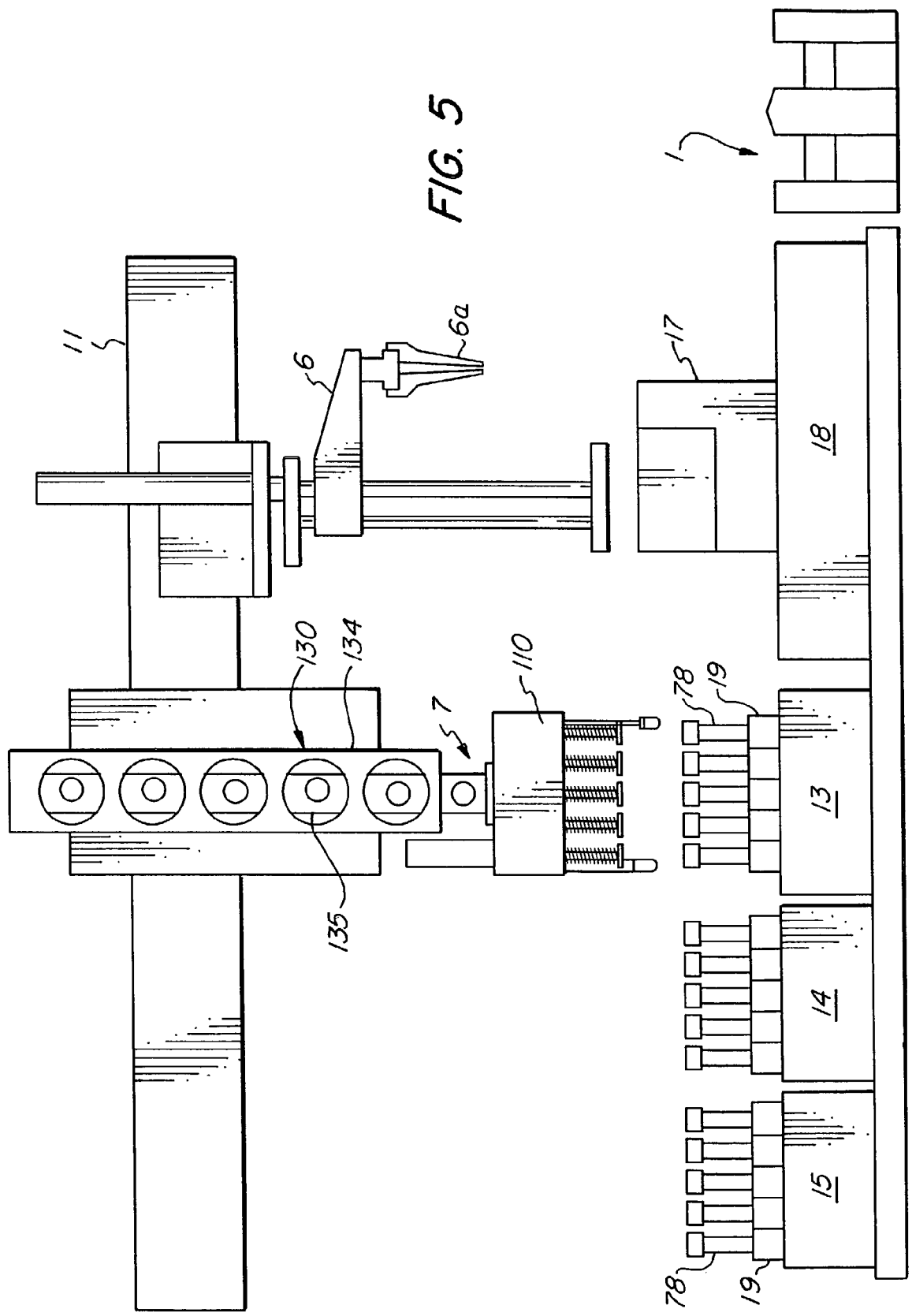
FIG. 5 is a simplified schematic elevation view of the bucket gripper robot, the sample tube gripper robot, tabletop components as shown in FIG. 3 and the external conveyor.
Figure 6:
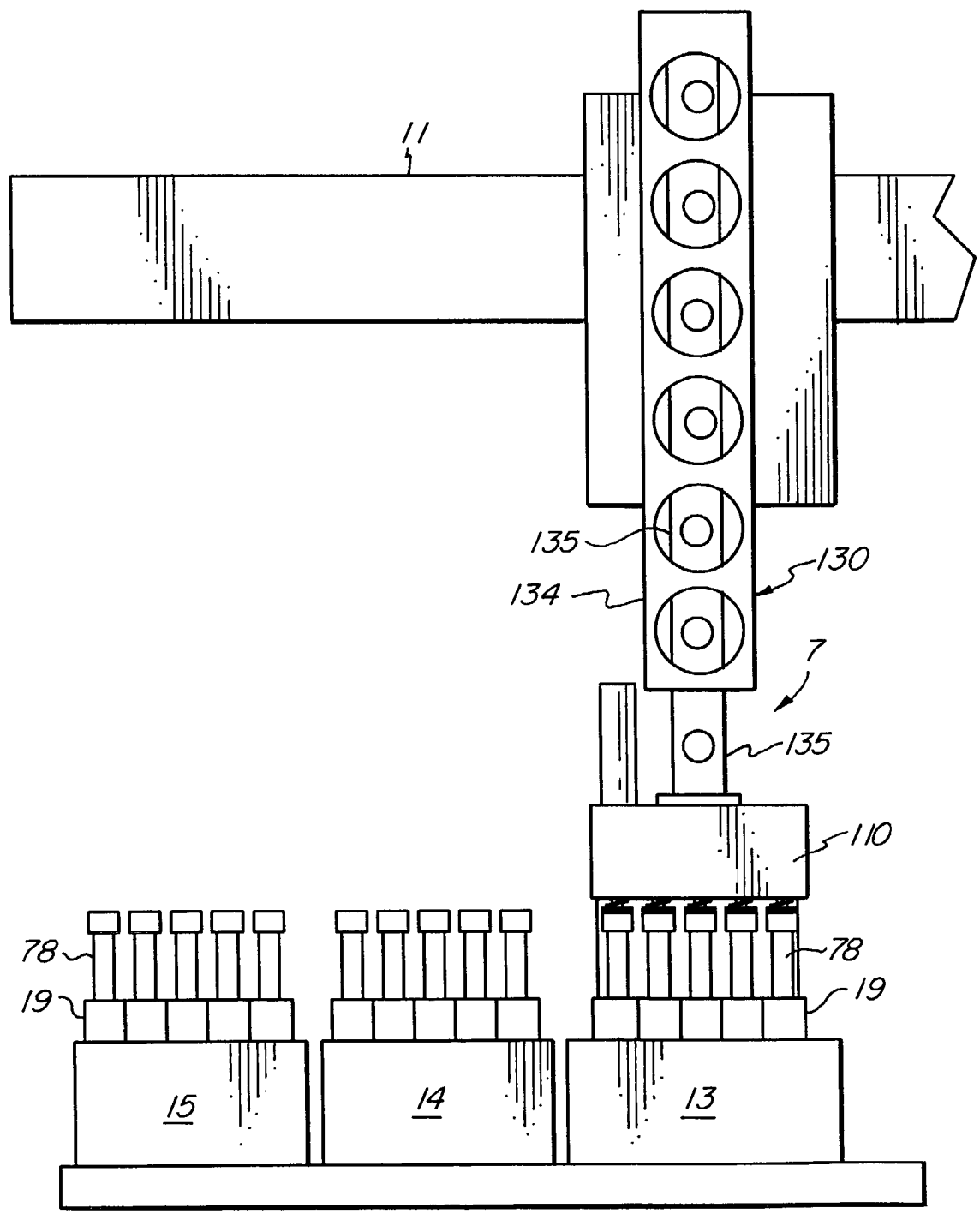
FIG. 6 is a simplified schematic elevation of the bucket gripper robot engaging a bucket in the unloading queue.

Once all four of the spun sample tube buckets 19 are unloaded from the centrifuge 4 into the unloading queue 13 each sample tube bucket 19 will have up to fifteen sample tubes. The next function is to decap these spun sample tubes by decappers 16, 17 (FIG. 3), which are of the type shown in U.S. Pat. No. 6,257,091 for Automatic Decapper, which is incorporated by reference herein. During decapping the cap is removed from a spun sample tube by the decappers 16, 17 (FIGS. 4 and 5) and the uncapped sample tube is ultimately transported back to the conveyor 1 to the interface gate 75 in a place position 73 (FIG. 3) to permit the conveyor 1 to transport the spun and decapped sample tube to another processing station.

The lab cell centrifuging-module 2 includes two decappers 16, 17 to maintain a desired throughput since one decapper is not fast enough to decap the sample tubes at a desired rate, and because the sample tube gripper robot 6 can be operated to move sample tubes faster to the decapper than one decapper can decap them. The decappers 16 and 17 have doors 40 and 41 (FIG. 3) that sequentially open to permit sequential insertion of a capped sample tube in each decapper.

During operation of the two decappers 16 and 17 (FIG. 3) the respective upper doors 40 and 41 are opened. The sample tube gripper robot 6 puts a capped sample tube into one decapper, releases the sample tube, moves out, and the upper door of the decapper closes. A turning device (not shown) inside the decapper lowers the capped sample tube to a specific position while a clamp (not shown) holds the cap to thereby separate the sample tube and the cap. The respective decapper doors 40, 41 open and release a respective cap, which falls down a chute 161, 162 (FIG. 8) into a waste bin 9 (FIG. 2).

The tube gripper robot 6 (FIG. 3) moves back and forth over the unloading queue 13 to the first available bucket in the unloading queue 13 where the spun sample tubes are located and picks a capped sample tube from the bucket 19. The sample tube gripper robot 6 (FIG. 3) moves in the "x" direction and can access sample tubes at only one specific "y" position on the unloading queue 13. Thus sample tube rows in the unloading queue 13 must be aligned with the pick position of the sample tube gripper robot 6. When one row of five sample tubes are unloaded from the unloading queue 13 the sample tube bucket 19 must be moved by the slide carriage 36, an amount equal to the distance between sample tube rows, to position the next row of five sample tubes in alignment with the pick position of the sample tube gripper robot 6.

The sample tube gripper robot 6 then moves in the "x" direction and in alignment with a row of unpicked sample tubes in the unloading queue 13. The unloading queue 13 must then realign a new row of capped sample tubes for the sample tube gripper robot 6 each time the sample tube gripper robot 6 completes removal of a previous row of capped and spun sample tubes from a sample tube bucket 19.

Referring to FIG. 4 which is a top view of the tabletop assembly 5, a reference line 50 indicates the "x" direction path of movement of the sample tube gripper robot 6. The path line 50 is used for purposes of explanation and is not a scaled representation of the actual movement path of the sample tube gripper robot 6. The sample tube gripper path 50 is also at the predetermined "y" position on the unloading queue 13 where the sample tube gripper robot 6 can pick sample tubes. Thus the sample tube gripper path 50 and the bucket gripper access path 65 are actually coincident.

There are five pick positions on the tube gripper path 50 such as indicated by the reference circles 51, 52, 56, 57 and 58 (FIG. 4) along the tube gripper path line 50. The reference circles 51, 52, 56, 57 and 58 correspond to the five sample tube positions in the sample tube bucket 19 on the sample tube gripper path 50 in the unloading queue 13.

Therefore, the sample tube gripper robot 6 moves to position 52 on the path line 50 (FIG. 4) picks the first sample tube, brings that sample tube to one of the decappers such as 16, the decapper 16 closes its door 41, decaps the sample tube and the sample tube gripper robot 6 moves back along the path line 50 and picks the next sample tube at the pick position 51 (FIG. 4), and moves it to the other decapper 17.

After the sample tube from the pick position 52 is decapped in the decapper 16 the decapper door 41 opens. The sample tube gripper robot 6, after delivering the capped sample tube from the next pick position 51 into the decapper 17 picks the uncapped sample tube from the decapper 16 and moves it to a puck position 53 on the rectangular path conveyor 18 (FIG. 4) where an empty puck 54 should be available. The puck position 53 aligns with the sample tube gripper path 50. Other empty pucks on the rectangular path conveyor 18 are designated by the circles 54.

Thus the sample tube gripper robot 6 moves to the decapper 16, where the sample tube has been decapped and the decapper door 41 is open. The sample tube gripper robot 6 removes the decapped sample tube from the decapper 16 moves the decapped sample tube to the rectangular path conveyor 18, to the puck position 53 (FIG. 4) releases the sample tube into a puck 54 and moves to the next sample tube in the bucket row on the sample tube gripper path 50. The sample tube gripper robot 6 repeats this process five times whereby the row of sample tubes on the gripper path 50 in the sample tube bucket 19 is emptied of spun sample tubes for decapping.

Next the unloading queue 13 slide carriage 36 (FIG. 32) moves the sample tube buckets 19 a small "y" distance to align the next row of available spun and capped sample tubes in the bucket 19 in alignment with the sample tube gripper path 50 (FIG. 4). The reference line 55 (FIG. 4) indicates the next available row of capped sample tubes that will move into alignment with the sample tube gripper path 50 to enable the sample tube gripper robot 6 to pick the next row of five capped and spun sample tubes from the sample tube bucket 19.

It should be noted that the slide carriage 36, when supporting the buckets 19 on the unloading queue 13, prevents the sample tube buckets 19 from dropping back into the centrifuge opening 28 (FIGS. 3, 4 and 32).

As previously noted each sample tube bucket 19 (FIG. 37) has three rows of five sample tube positions or fifteen sample tubes per bucket. Four sample tube buckets 19 occupy the unloading queue 13 for total of sixty sample tubes (FIG. 4). If all sixty sample tube positions in the four buckets 19 are filled with sample tubes, the slide carriage 36 of the unloading queue 13 must make twelve moves to align each five row line of sample tube positions with the sample tube gripper path 50 (FIG. 4).

When all capped and spun sample tubes in a sample tube bucket 19 (FIG. 4) are unloaded by the sample tube gripper robot 6 from the unloading queue 13 the bucket gripper robot 7 moves to the pick position above the centrifuge opening 28. The unloading queue slide carriage 36 (FIG. 32) moves that empty sample tube bucket 19 to the pick position over the centrifuge opening 28 (FIG. 4), and the mobile deflectors 35 (FIG. 32) move to the pick position opening over the centrifuge opening 28 to compress the normally expanded sample tube bucket 19 (FIG. 4). The bucket gripper robot 7 then picks up the just emptied sample tube bucket 19 from the unloading queue 13 and moves the empty sample tube bucket 19 back to an empty loading queue such as 14 or 15 (FIG. 3).

Once the first empty sample tube bucket 19 is transferred from the unloading queue 13 onto the loading queue 14, the slide carriage 36 (FIG. 32) of the unloading queue 13 aligns the next available bucket row with the sample tube gripper path 50 (FIG. 4). The sample tube gripper robot 6 sequentially removes these sample tubes (up to five sample tubes) into the decappers 16 and 17. Sample tube row alignment with the sample tube gripper path 50 occurs three times for each sample tube bucket 19 because there are three rows of five sample tube positions in each sample tube bucket 19 (FIG. 4).

As previously noted, when a sample tube bucket 19 on the unloading queue 13 is empty it will be made accessible to the bucket gripper robot 7 by movement of the slide carriage 36 and the mobile deflector 35 of the unloading queue 13 (FIG. 4) above the centrifuge opening 28. The bucket gripper robot 7 moving along the access path 65 (FIG. 32) picks the empty sample tube bucket 19 and moves the empty bucket 19 into the loading queue 14 or 15. Thus the unloading queue 13 moves the empty sample tube bucket 19 into the position where it can be picked by the bucket gripper robot 7, and the slide carriage 24 of the loading queue 14 or 15 provides an open bucket receiving space for the bucket gripper robot 7 to unload the empty sample tube bucket 19. The loading queue 14, 15 (FIG. 35) has four sample tube bucket positions 20, 21, 22 and 23 that can now be filled with the empty buckets 19 transported by the bucket gripper robot 7. Bucket exchanges continue for each loading queue 14, 15 until all of the sixty sample tubes from the four sample tube buckets 19 on the unloading queue 13 are decapped.

The bucket gripper robot 7 always transfers empty sample tube buckets 19 from the unload queue 13 to the same "y" position in the loading queues 14 or 15. Thus the positioning of the empty sample tube buckets 19 into the loading queues 14, 15 is determined by the slide carriage 24 of the loading queues 14, 15. If a loading queue 14 or 15 is empty all sample tube bucket positions 20, 21, 22 and 23 (FIGS. 35 and 36) are empty.

When the unloading queue 13 has a sample tube bucket 19 that has been emptied of sample tubes the empty bucket 19 becomes accessible to the bucket gripper robot 7 which moves along a predetermined "x" path or access path 65 (FIG. 32) in a predetermined "y" position over the unloading queue 13. The bucket gripper robot 7 moves down and picks the empty bucket 19 from a bucket position 31 (FIG. 32) on the slide carriage 36 of the unloading queue 13, moves up (same "y" position) and makes an "x" movement on the access path 65 above one of the loading queues 14 or 15. The loading queue 14, 15 moves the empty bucket position 23 on the slide mechanism 24 to the same "y" position as the bucket gripper robot 7. Thus the loading queue 14, 15 (FIG. 35) positions the empty bucket position 23 in the slide mechanism 24 to align with the access path 65 (FIG. 35) beneath the bucket gripper robot 7 (FIG. 4).

The access path 65 for the bucket gripper robot 7 is noted on FIGS. 32 and 35. The bucket gripper 7 is only able to move back and forth in the "x" direction and up and down in the "z" direction but does not move in the "y" direction. Thus the access path line 65 determines the "y" position of the bucket gripper robot 7. Therefore the slide carriage 36 of the unloading queue 13 and the same slide carriage 24 of the loading queues 14, 15 must move an appropriate amount in the "y" direction to permit removal of a sample tube bucket 19 from the unloading queue 13 and disposition of the same bucket onto a loading queue 14, 15.

There is a predetermined pickup position for the bucket gripper robot 7 along the access path 65 for removing an empty sample tube bucket 19 from the unloading queue 13 (FIG. 32). There are also predetermined drop-off positions along the path 65 for drop off of the empty sample tube bucket 19 in the loading queues 14, 15.

The slide carriage 36 of the unloading queue 13 (FIG. 32) moves the first empty sample tube bucket into alignment with the access path 65. The bucket gripper robot 7 can now access the empty sample tube bucket 19 and picks that bucket, moves it in an "x" direction along the path 65 above the loading queue 14 or 15. The loading queue slide carriage 24 moves the first bucket position 23 (FIG. 35) to where the bucket gripper robot 7 is holding the empty bucket. Then the bucket gripper robot 7 moves down, puts the empty bucket 19 onto the position 23, releases the bucket, moves up, and moves in the "x" direction along the path 65 back to the unloading queue 13.

The unloading queue slide carriage 36 (FIG. 32) then moves to place the empty sample tube bucket 19 at bucket position 32 in alignment with the bucket gripper access path 65 so that the bucket gripper robot 7 (FIG. 4) can pick the next empty sample tube bucket 19. The bucket gripper robot 7 picks the empty sample tube bucket 19 from the bucket position 32 (FIG. 32) and moves it back to the available loading queue 14, 15 (FIG. 4). The loading queue slide carriage 24 (FIG. 35) moves in the "y" direction to present the next empty bucket receiving position 22 in alignment with the bucket gripper access path 65. The bucket gripper robot 7 (FIG. 4) moves down, releases the bucket 19 into the bucket receiving position 22 on the loading queue slide carriage 24 (FIG. 35) and moves back to the unload queue 13 where the empty sample tube bucket 19 at the position 33 (FIG. 35) is moved to access path 65 and so on.

Figure 9:
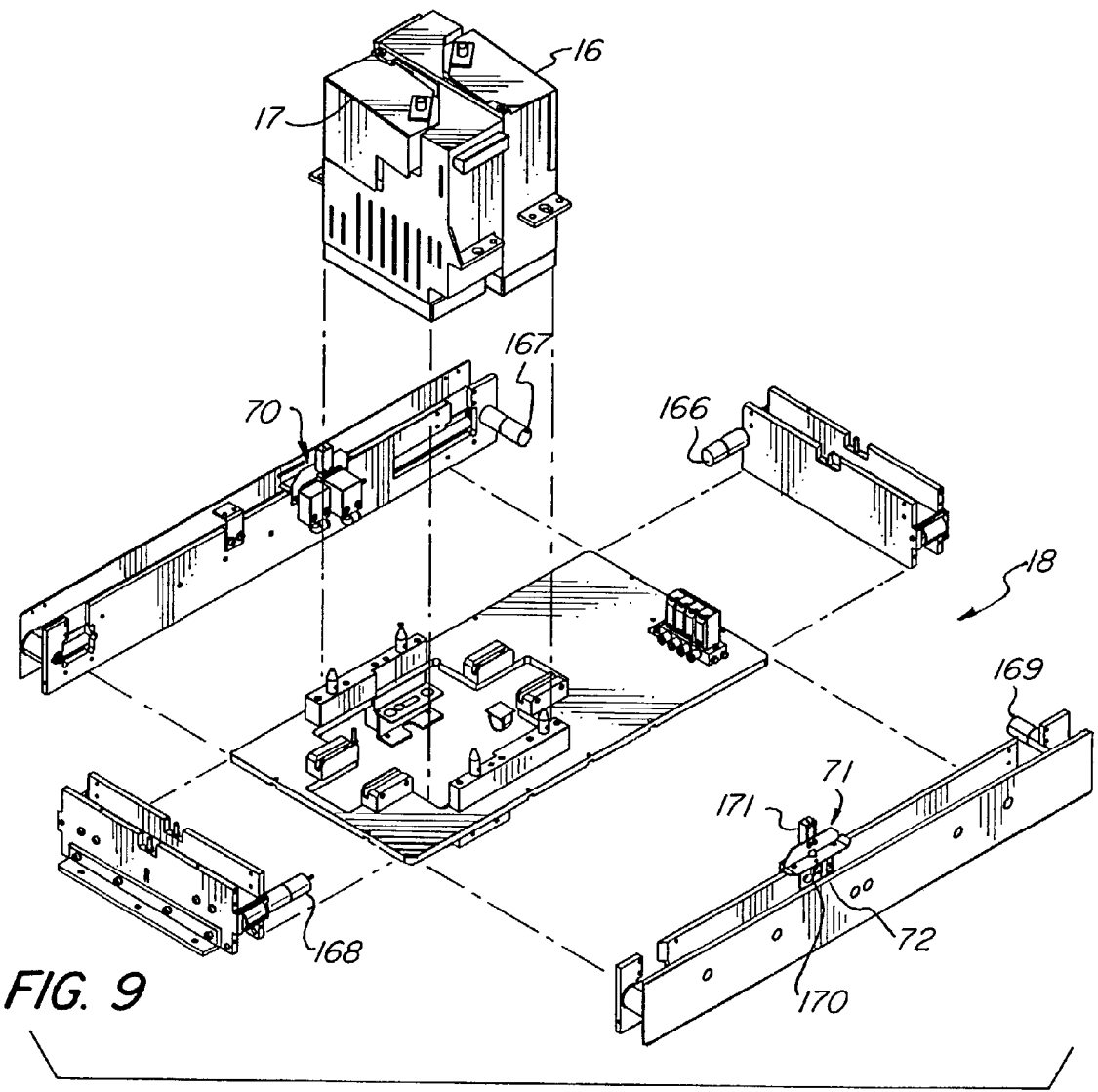
FIG. 9 is a fragmentary perspective view, partially exploded, of the rectangular path conveyor framework surrounding the decappers.
Figure 10:
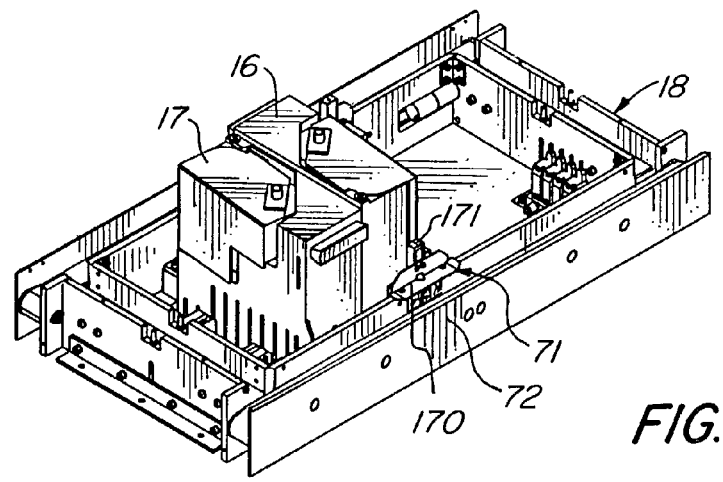
FIG. 10 is a non-exploded view of the structure shown in FIG. 9.

The rectangular conveyor 18 (FIGS. 3 and 4) receives decapped sample tubes that the sample tube gripper robot 6 removes from the decappers 16, 17 and places the decapped sample tubes in pucks 54 on the conveyer 18. The conveyor 18 (FIGS. 3 and 4) includes four belts moving the pucks 54 along a rectangular path in one direction. FIGS. 9 and 10 show framework for the internal conveyor 18 and the belt drives 166, 167, 168 and 169 for each of the four conveyor belts of the conveyor 18. The decapped sample tubes are removed from the decappers 16 or 17 and placed in an empty puck 54 at position 53 on the conveyor 18 (FIG. 4). A puck release mechanism 70 (FIGS. 4 and 8) on the conveyor 18 releases the puck 54 and the conveyor 18 moves the puck 54 to the internal pick position 72 (FIG. 4) at the conveyor 18. A mechanism 71 (FIGS. 4, 8 9 and 10) holds the puck 54 at the pick position 72. The puck holding mechanism 71 (FIG. 4) includes a retractable pin device or puck stopper 170 (FIGS. 9 and 10) for stopping movement of the pucks on the conveyor 18. A sensor 171 indicates that there is a sample tube in the puck 54.

Thus the conveyor 18 (FIG. 4) defines a rectangular path of moving pucks 54 with decapped sample tubes. The sample tube gripper robot 6 will always move an uncapped sample tube from one of the decappers 16 or 17 to an empty puck 54 at the position 53 on the conveyor 18 (FIG. 4). The puck release mechanism 70 at position 53 (FIG. 4) releases a puck 54 with an uncapped sample tube for movement to the pick position 72 on the conveyor 18.

The sample tube gripper robot 6 picks the next decapped sample tube from the decapper 16, for example, and brings the decapped sample tube to the next empty puck 54 at the puck position 53 (FIG. 4). The puck release mechanism 70 (FIG. 4) releases the puck 54 when it receives a decapped sample tube to provide a chain of pucks 54 with decapped sample tubes directed to the puck holding mechanism 71. The pucks 54 with decapped sample tubes line up on the conveyor 18 at the puck holding mechanism 71 at the pick position 72 on the conveyor 18 (FIG. 4).

The pick position 72 (FIG. 4) is also accessible by the sample tube delivery robot 8. Thus if there is a puck 54 with a decapped sample tube, the sample tube delivery robot 8 will pick the decapped sample tube from the conveyor 18 at the pick position 72 and will move that decapped sample tube to the interface gate 75 on the main conveyor 1 at a place position 73 (FIGS. 3 and 4). The decapped sample tube is inserted in a puck 54 at the place position 73 on the conveyor 1 (FIG. 4) for movement by the conveyor 1 to other processing stations (not shown).

The sample tube delivery robot 8 will then pick a capped sample tube in the interface gate pick position 74 on the conveyor 1 (FIG. 4) and move the capped sample tube to one of the open spots in a sample tube bucket 19 in the loading queues 14, 15. Thus the sample tube delivery robot 8 is not only continuously loading capped sample tubes from the conveyor 1 into sample tube buckets 19 on the loading queues 14 and 15, but on the way back is also transporting decapped sample tubes from the stop position 72 on the conveyor 18 to the interface gate place position 73 (FIGS. 3 and 4).

Referring again to FIGS. 3 and 4 the sample tube delivery robot 8 moves to pick position 74 on the conveyor 1, picks a capped sample tube from the conveyor 1, moves the capped sample tube into one of the load queues 14 or 15 (FIG. 4), moves back to the puck stop position 72 on conveyor 18 and, if there is an available uncapped sample tube there, picks that uncapped sample tube and moves it into the place position 73 on the main conveyor 1. Then the sample tube delivery robot 8 (FIG. 3) moves to the pick position 74 (FIG. 4) on the main conveyor 1, picks an incoming capped sample tube from the main conveyor 1, brings the capped sample tube to one of the buckets 19 on load queue 14 or 15, and on the way back again stops at the puck stop position 72 (FIG. 4) on conveyor 18, picks an uncapped sample tube, brings it to place position 73 on the main conveyor 1 to complete the pick-up and delivery cycle for the sample tube delivery robot 8.

In the bucket movement cycle the bucket gripper robot 7 picks sample tube buckets 19 filled with sample tubes out of the loading queues 14 and 15 and moves the buckets 19 into and out of the centrifuge 4 through the opening 28 (FIG. 3). The bucket gripper robot 7 also moves sample tube buckets 19 after a spin cycle, that have been removed from the centrifuge 4, placed on the unloading queue 13, unloaded while on the unloading queue 13, and transfers such unloaded buckets 19 from the unloading queue 13 onto the loading queues 14 or 15 for reloading. The sample tube gripper robot 6 continuously transfers spun sample tubes from the sample tube buckets 19 in the unloading queue 13 into the decappers 16 and 17 (FIGS. 3 and 4). The sample tube gripper robot 6 (FIG. 3) also moves uncapped sample tubes from the decappers 16 or 17 to the position 53 (FIG. 4) on the conveyor 18.

As previously indicated the centrifuge 4 has four bucket receiving receptacles or spaces of predetermined size in a cross-pattern that accommodate standard sample tube buckets or centrifuge buckets (not shown) available from the manufacturer of the centrifuge 4. The bucket receiving receptacle in the centrifuge defines the bucket size. Standard centrifuge buckets are not used in the centrifuge 4 because standard centrifuge buckets have only a 4×3 position matrix for sample tubes with a bucket capacity of twelve instead of fifteen sample tube positions. A four bucket batch of standard centrifuge buckets accommodates only forty-eight sample tubes rather than sixty sample tubes per four bucket batch of the present sample tube buckets 19, thus affecting throughput.

Another consideration dictating against the use of standard centrifuge buckets is that sample tubes are moved in and out of the centrifuge buckets by a robot. The sample tube positions in a standard centrifuge bucket make it difficult for the sample tube gripper robot 6 to pick individual sample tubes out of a standard bucket without interference with other sample tubes in the standard centrifuge bucket. A further problem is that the standard centrifuge buckets must be manually held down to avoid bucket lift during sample tube withdrawal since the standard centrifuge buckets have no built in hold down features.

Figure 38:
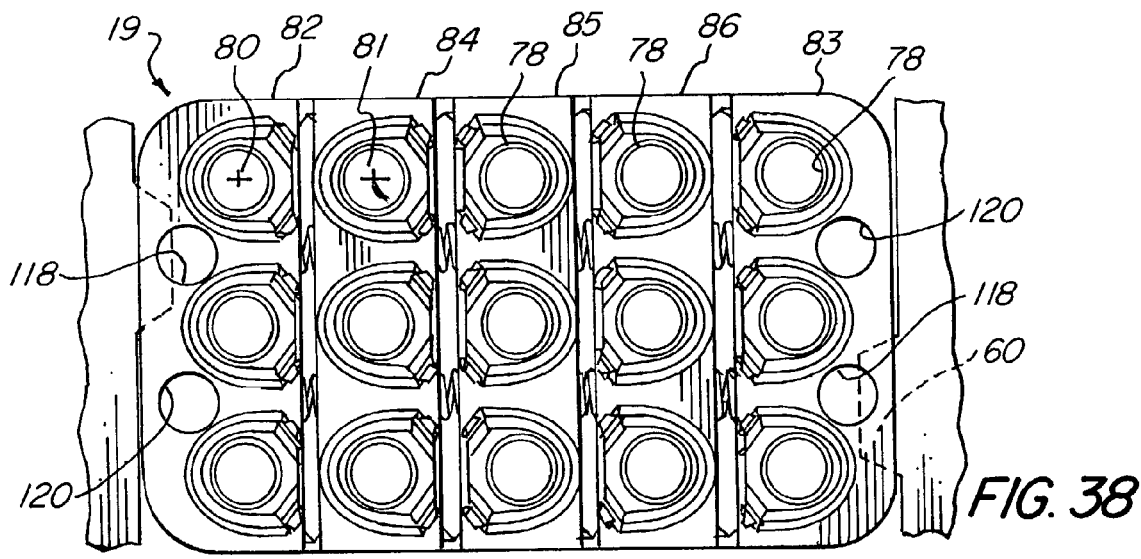
FIG. 38 is a top plan view thereof in engagement with a hold down device 60 from one of the queues.

For example, referring to FIG. 38 the centers of two sample tube positions are indicated by the reference numbers 80 and 81. The corresponding distance between the sample tube centers 80 and 81 in a standard centrifuge bucket (not shown) would make it difficult for the sample tube gripper robot 6 and the sample tube delivery robot 8 to remove and replace individual sample tubes in the standard centrifuge buckets without interfering with nearby sample tubes in the standard centrifuge bucket.

To solve this interference problem the expandable centrifuge bucket or sample tube bucket 19 (FIG. 37) was developed. The sample tube bucket 19 has 3×5=15 positions to provide a capacity of sixty sample tubes per four bucket batch. Thus the sample tube bucket 19 can be in an expanded condition (FIGS. 4 and 37) when sample tubes are individually removed, and in a compressed condition (FIG. 39) when the bucket 19 is disposed in the centrifuge 4.

Figure 33:
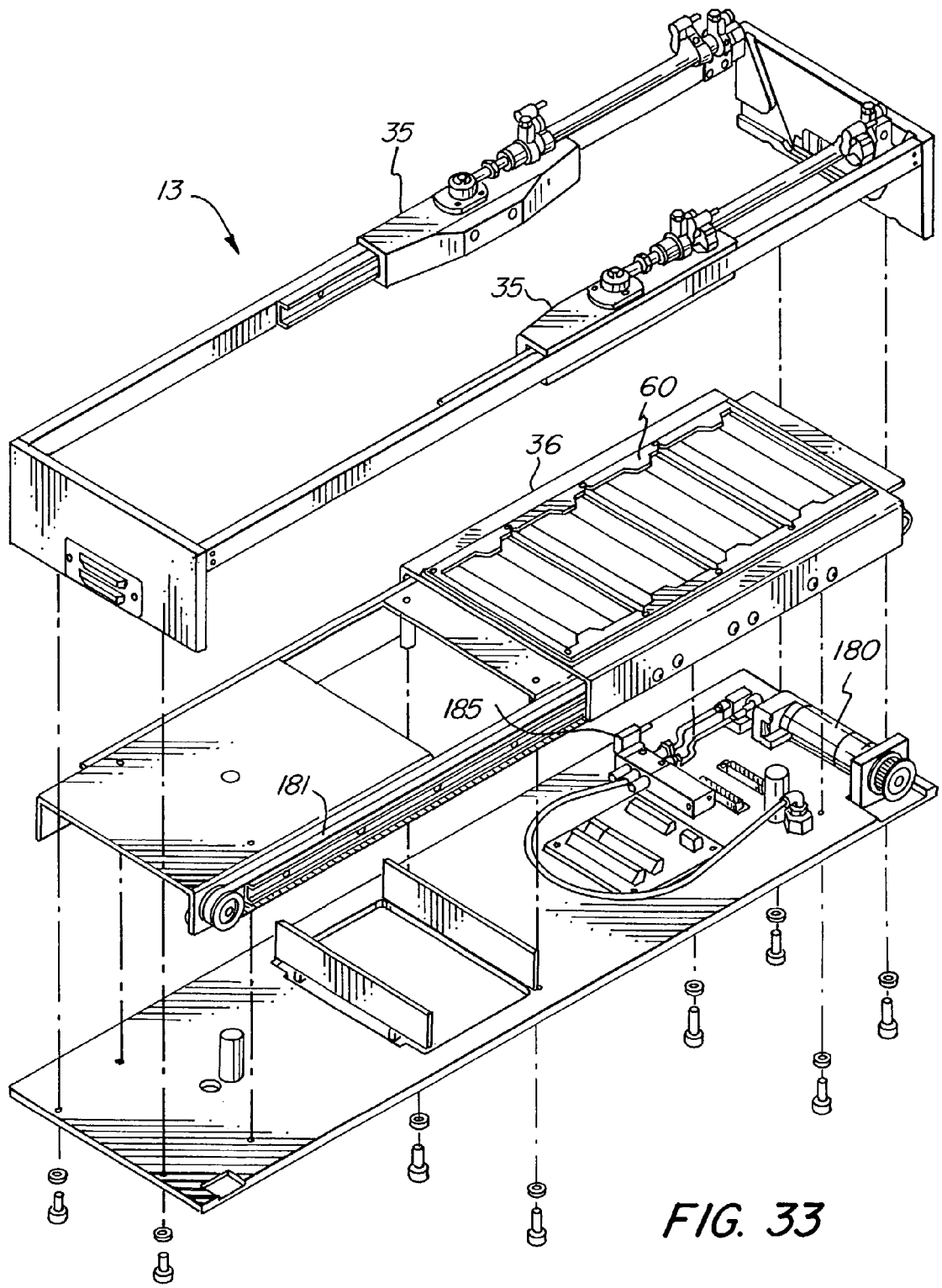
FIG. 33 is a partially exploded perspective view of the unloading queue as shown in FIG. 32.
Figure 34:
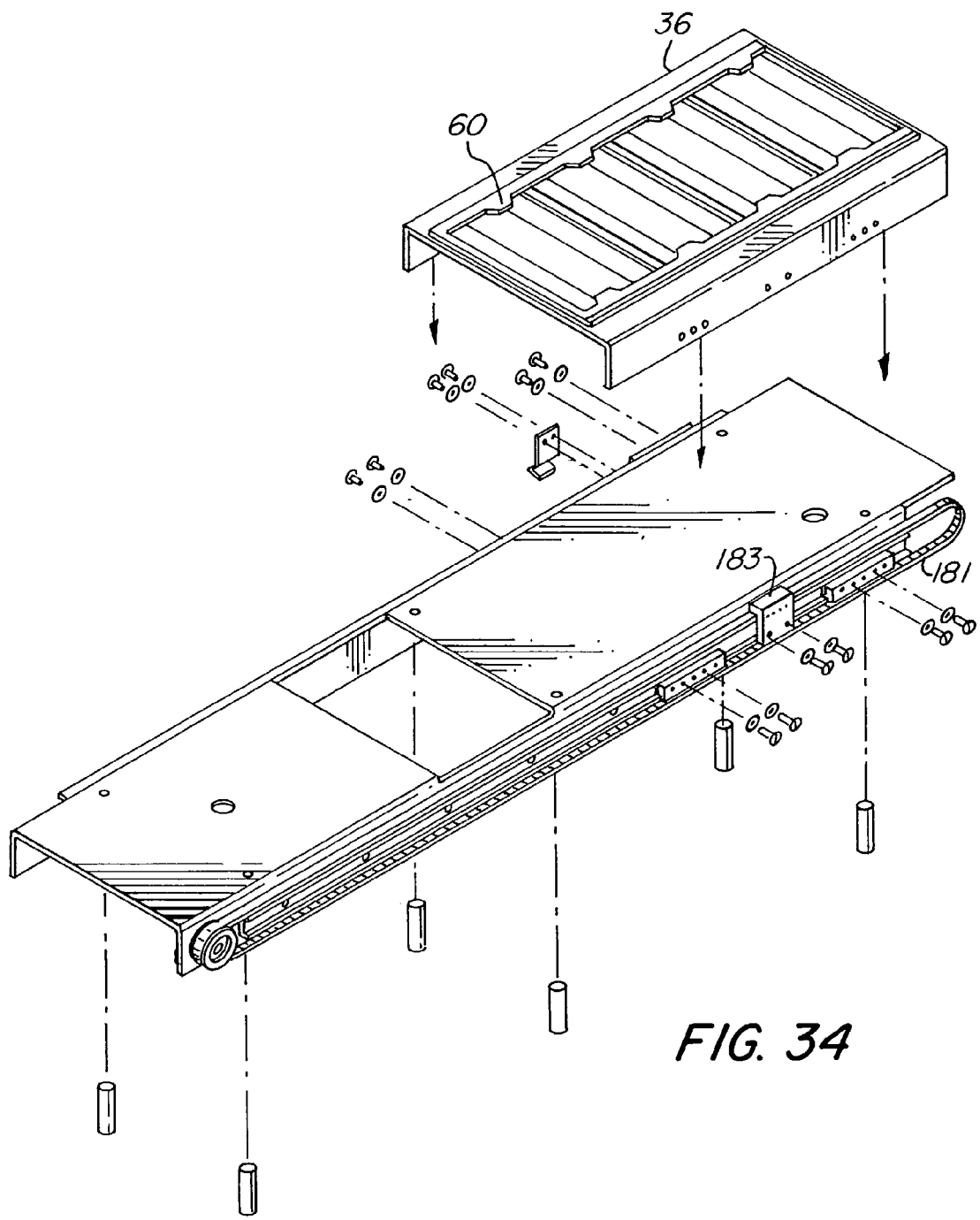
FIG. 34 is a partially exploded perspective view of the middle structure of the unloading queue shown in FIG. 33.

The mobile deflectors 35 (FIG. 32) on the unloading queue 13, which compress the sample tube bucket 19 from a normally expanded condition to a compressed condition, are mobile because they must move to the position 65 shown in FIG. 32 to align with the bucket gripper robot 7, to enable the bucket gripper robot 7 (FIG. 3) to engage the sample tube bucket 19. The mobile deflectors 35 (FIG. 32) must then move away from the centrifuge opening 28 on the unloading queue 13 (FIG. 4) to enable the bucket gripper robot 7 to deposit the compressed sample tube bucket 19 through the opening 28 into the centrifuge 4 (FIG. 2). The mobile deflector assembly with pneumatic driven mobile deflectors 35 are shown in FIG. 33. The belt drive 180 moves the slide carriage 36 (FIG. 33). The slide carriage 36 (FIG. 32) for the unloading queue 13 is substantially the same as the slide carriage 24 (FIG. 35) for the loading queues 14, 15. Member 183 (FIG. 34) connects the slide carriage 36 to a drive belt 181.

The loading queue deflectors 26, 27 have a fixed position because the sample tube delivery robot 8 brings sample tubes to the sample tube buckets 19 in the loading queues 14, 15 when the sample tube buckets 19 are positioned beyond the deflectors 26, 27. The sample tube buckets 19 are thus positioned to receive sample tubes in the loading queues 14, 15 in an expanded condition. FIG. 35 shows a sample tube bucket 19, above one of the loading queues 14, 15, with arrows 189 indicating the compression force provided by the deflectors 26 and 27. Home sensors 185 (FIG. 33) and 184 (FIG. 36) indicate a home position of the slide carriages 36 and 24.

The sample tube bucket 19 (FIG. 37) is constructed of five sample tube holding sections, including similar end sections 82, 83 (FIGS. 40, 50-52 and 54-58) and similar middle sections 84, 85 and 86 (FIGS. 40-49). Projecting clasp portions 87 (FIG. 40) are formed on each of the bucket sections 82, 83, 84, 85 and 86. Thus the bucket end sections 82 and 83 each include two clasp portions 87 and the bucket middle sections 84, 85, 86 have four clasp portions 87.

The clasps 87 of one bucket section engage in notches 87a on adjacent bucket sections. The notches 87a define a bucket section expansion displacement distance identified by the reference number 88, (FIG. 40) to provide an expandable and compressible accordion-like assembly of the bucket sections 82, 83, 84, 85 and 86. Coil springs 89 (FIG. 40) between adjacent bucket sections bias the bucket sections to a normally expanded condition (FIG. 37).

Figure 43:
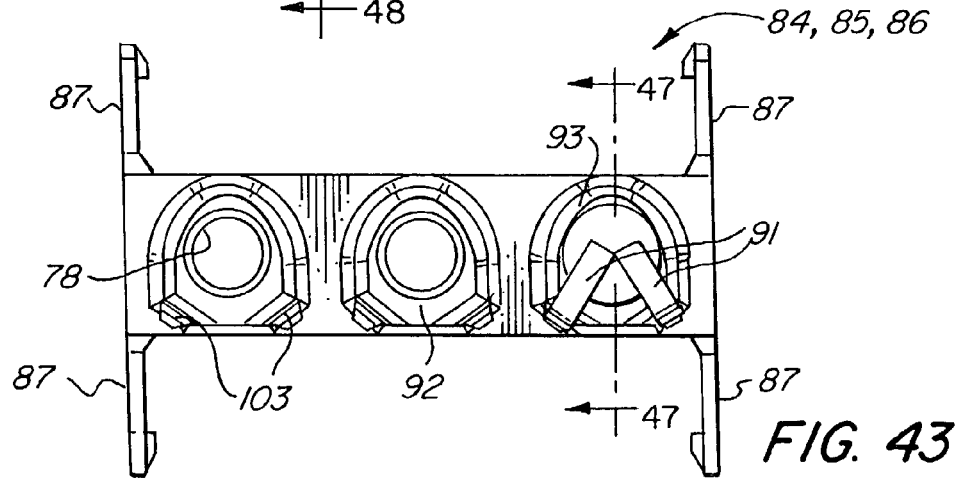
FIG. 43 is a top plan view of the sample tube bucket with leaf springs in one of the sample tube openings.
Figure 44:
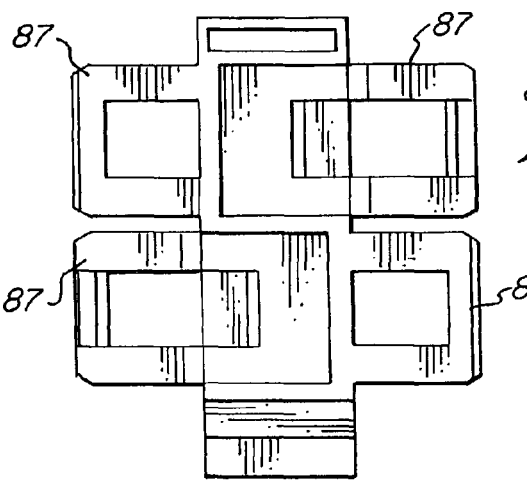
FIG. 44 is a side elevational view of the sample tube bucket middle section shown in FIG. 41.
Figure 47:
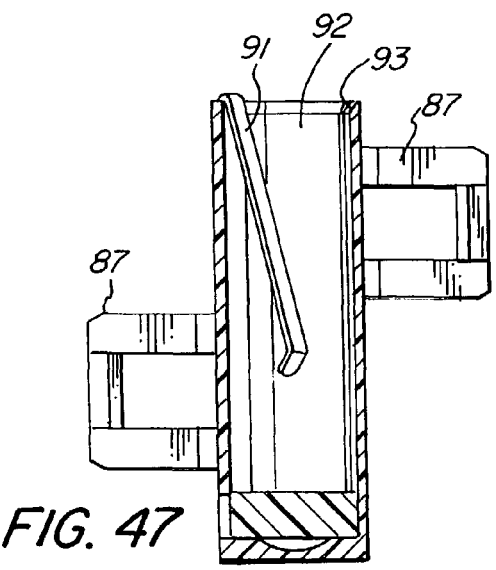
FIG. 47 is a sectional view taken on the line 47-47 of FIG. 43.
Figure 48:
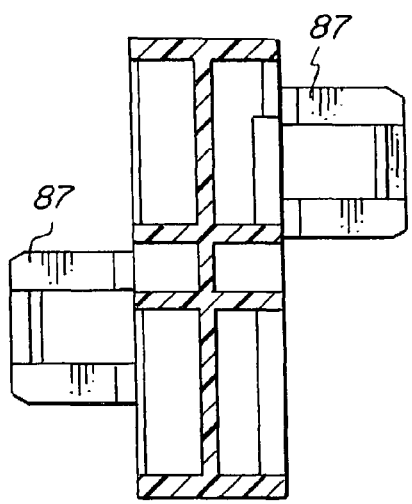
FIGS. 48 and 49 are sectional views taken on the lines 48-48 and 49-49 of FIG. 42.
Figure 45:
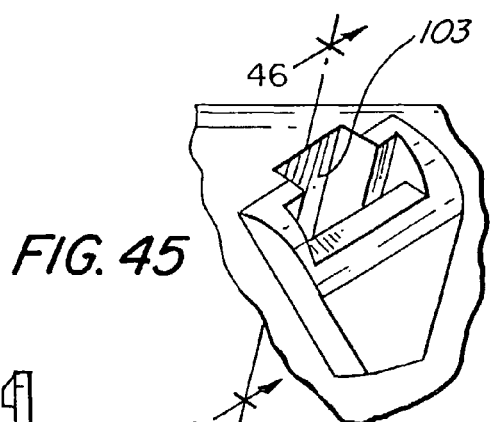
FIG. 45 is a fragmentary perspective view of a leaf spring slot in one of the sample tube receiving openings-of the sample tube bucket.
Figure 49:
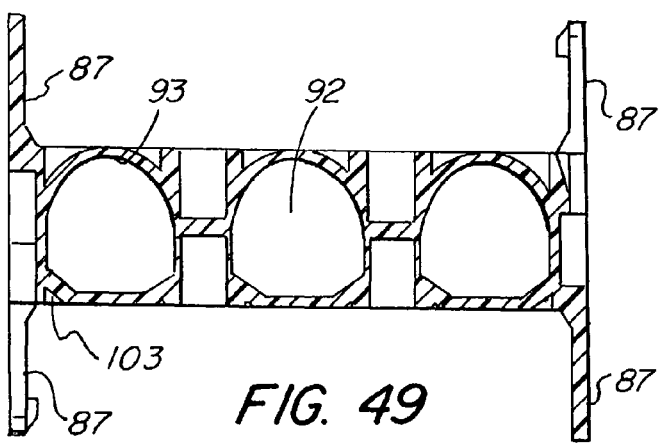
Figure 46:
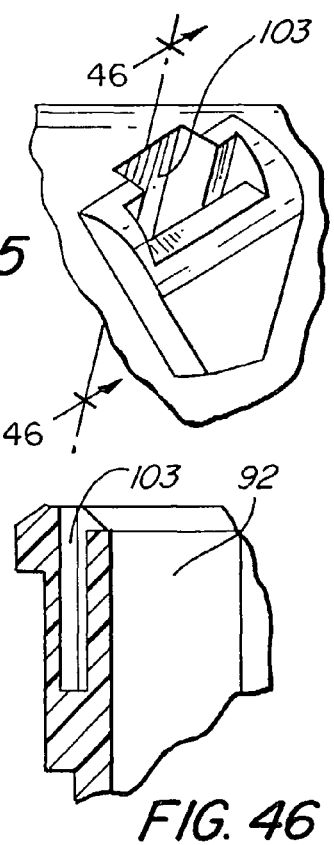
FIG. 46 is a sectional view taken on the lines 46-46 of FIG. 45.
Figure 54:
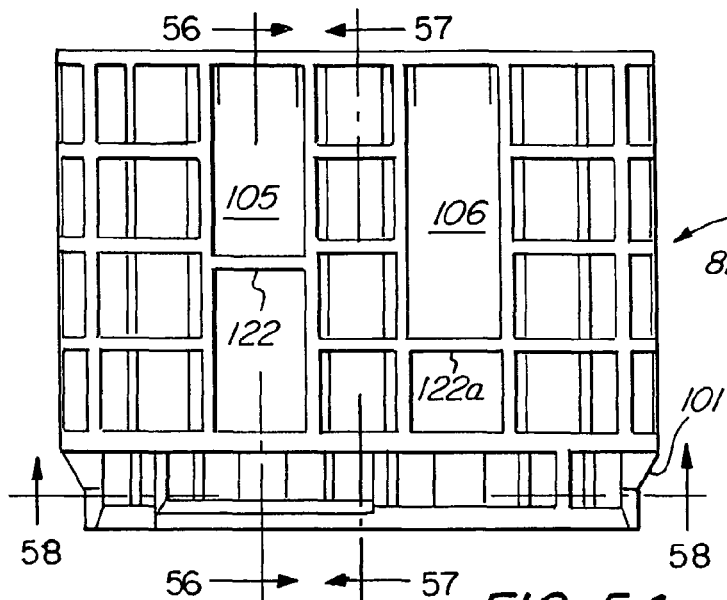
FIG. 54 is a front elevation view of the sample tube bucket end section as shown in FIG. 50.
Figure 55:
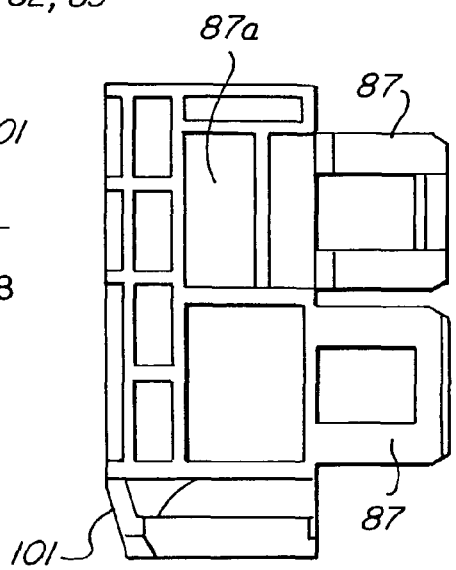
FIG. 55 is a side elevational view of one of the opposite sides of the sample tube bucket end section shown in FIG. 54.
Figure 56:
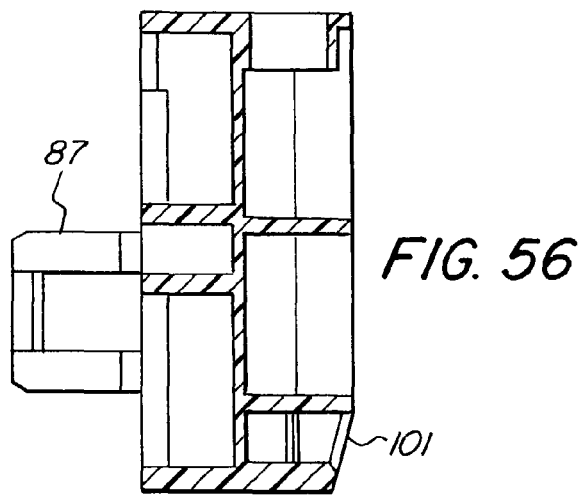
FIGS. 56-58 are sectional views taken on the lines 56-56, 57-57, and 58-58 of FIG. 54.
Figure 57:
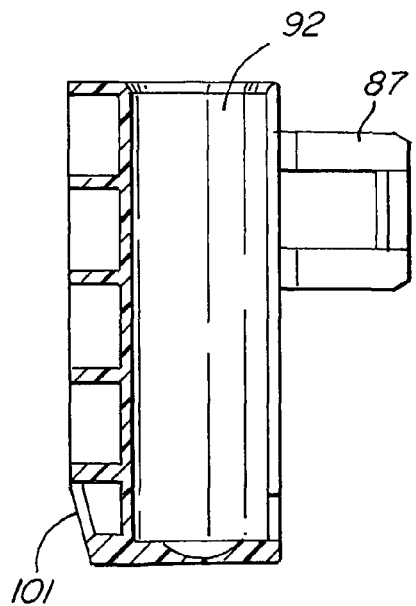
Figure 58:
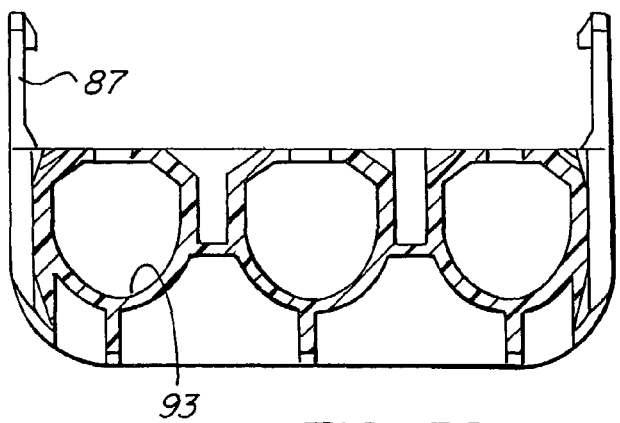

Leaf springs 91 (FIGS. 40, 43, 47 and 53), preferably two for each sample tube receiving opening 92 in the bucket 19, as shown in FIG. 43 are provided to bias a sample tube 78 against a rounded side 93 of the sample tube receiving opening 92. The leaf spring 91 (FIG. 43) is used because various different sample tube diameters may be used in the sample tube bucket 19. The leaf springs 91 press the sample tube 78 to the rounded side 93 of the sample tube receiving opening 92 on FIGS. 37 and 40. The leaf springs 91 thus urge the sample tubes 78 in the sample tube receiving opening 92 into a specific pick position that is accessible by the sample tube delivery robot 8.

A small offset 102 (FIG. 53) is provided on the leaf spring 91 to lock the leaf spring in a spring receiving recess 103 (FIGS. 43, 45 and 46) at the sample tube receiving opening 92. There are two spring receiving recesses 103 (FIG. 43) for each sample tube receiving opening 92 to accommodate the two leaf springs 91 that are provided in each sample tube receiving opening 92.

Rubber pads or sample tube cushions 90 (FIG. 40) are provided on the bottom of each sample tube receiving opening 92. Since the centrifuge 4 spins up to 4500 rpm a small blemish or burr on the bottom of the sample tube receiving opening 92 in the bucket 19 or on the bottom of the sample tube 78 can cause the sample tube to split. The rubber pad 90 is a buffer or cushion, between the sample tube 78 and the sample tube bucket 19 at the bottom of the sample tube receiving opening 92.

A lower end portion of the bucket end sections 82 and 83 (FIG. 50) includes two small rectangular openings 95 used together with slide carriage teeth 60 (FIGS. 32 and 35) to hold the sample tube bucket 19 on the slide carriages 24 and 36 when the sample tubes are withdrawn by the sample tube gripper robot 6.

Generally, there is a frictional force between the sample tubes 78 and the sample tube receiving openings 92 in the sample tube bucket 19. There is also a possibility that sample tubes 78 will become stuck in the sample tube bucket 19 for one or more different reasons such as bar code labels (not shown) on the sample tube 78 that partially peel away and adhere within the sample tube receiving opening 92 in the sample tube bucket 19. Thus it is necessary to hold the sample tube bucket 19 down while the sample tube gripper robot 6 or the sample tube delivery robot 8 picks the sample tube 78 from the sample tube bucket 19.

In order to accomplish hold down of the sample tube bucket 19 during robotic removal of sample tubes from the bucket 19 slide carriage teeth 60 (FIGS. 32 and 35) are provided on opposite sides of the slide carriages 24 and 36 of the unloading queue 13 and the loading queues 14, 15. The slide carriage teeth 60 engage a small rectangular opening 95 (FIG. 50) at the lower end portion of the bucket end sections 82, 83 to hold the buckets 19 down. The slide carriage teeth 60 are provided in all four bucket positions 20-23 and 31-34 of the respective slide carriages 24 and 36 (FIGS. 32 and 35).

The sample tube buckets 19 also include an angle portion 101 (FIGS. 54-57) at the bottom of the bucket, at the end sections 82 and 83, to enable the bucket to self guide when being moved downwardly into the centrifuge receptacle. Recesses 104 (FIG. 50) are provided in the bucket end sections 82 and 83 based on weight and stability considerations.

The bucket gripper robot 7 (FIG. 3) includes a bucket gripper head 110 (FIGS. 3, 29-31 and 59-60) having two similar depending thick posts 111 and 112 and two similar depending thin posts 113 and 114. A lower end portion 121 of the thick posts 111 and 112 can rotate to an eccentric position (FIGS. 29 and 30) which creates a small projecting edge 121a (FIGS. 30 and 60) on the lower end portion 121. A turning device inside the post 111 turns 180 degrees and moves the lower end 121 to an eccentric position, thus creating the edge 121a.

Figure 24:
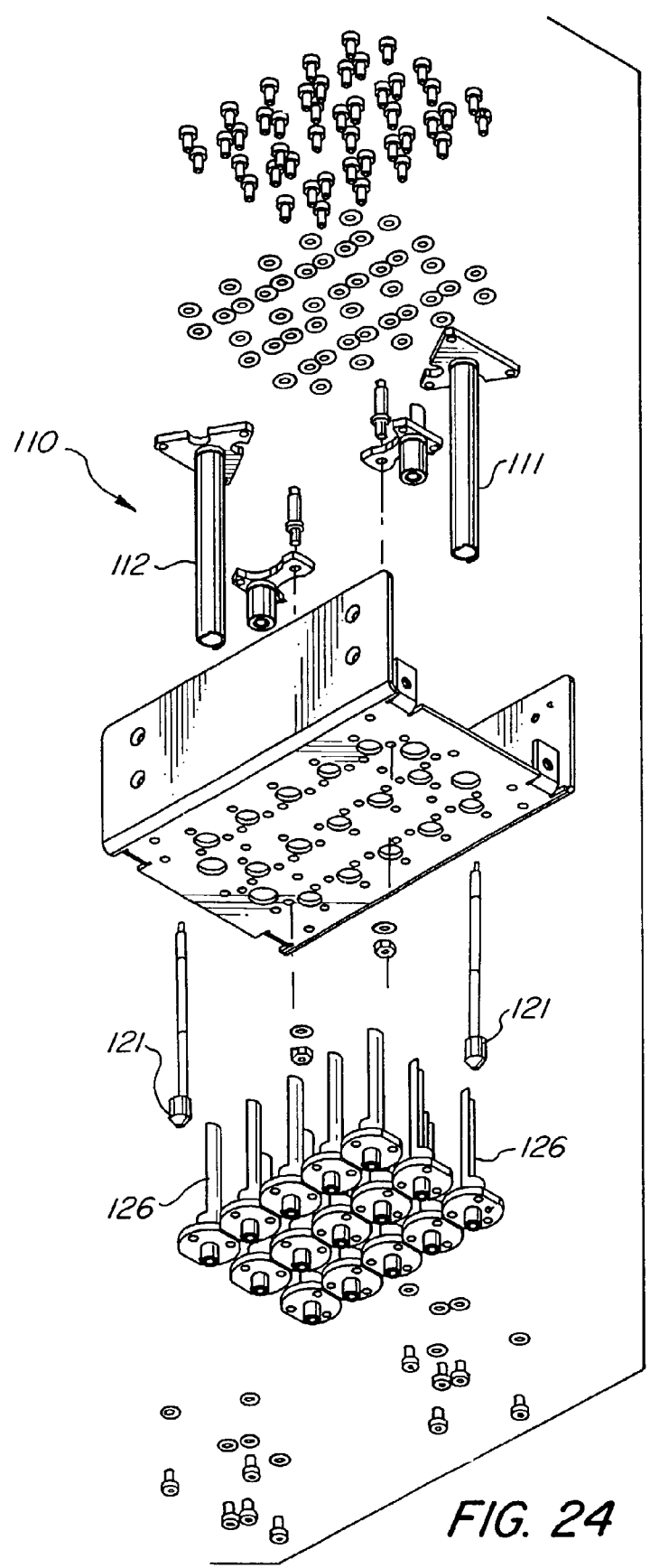
FIGS. 24, 25, 26, 27, 28, 29, 30 and 31 show the exploded and assembled components of the bucket gripper head for the bucket gripper robot.
Figure 25:
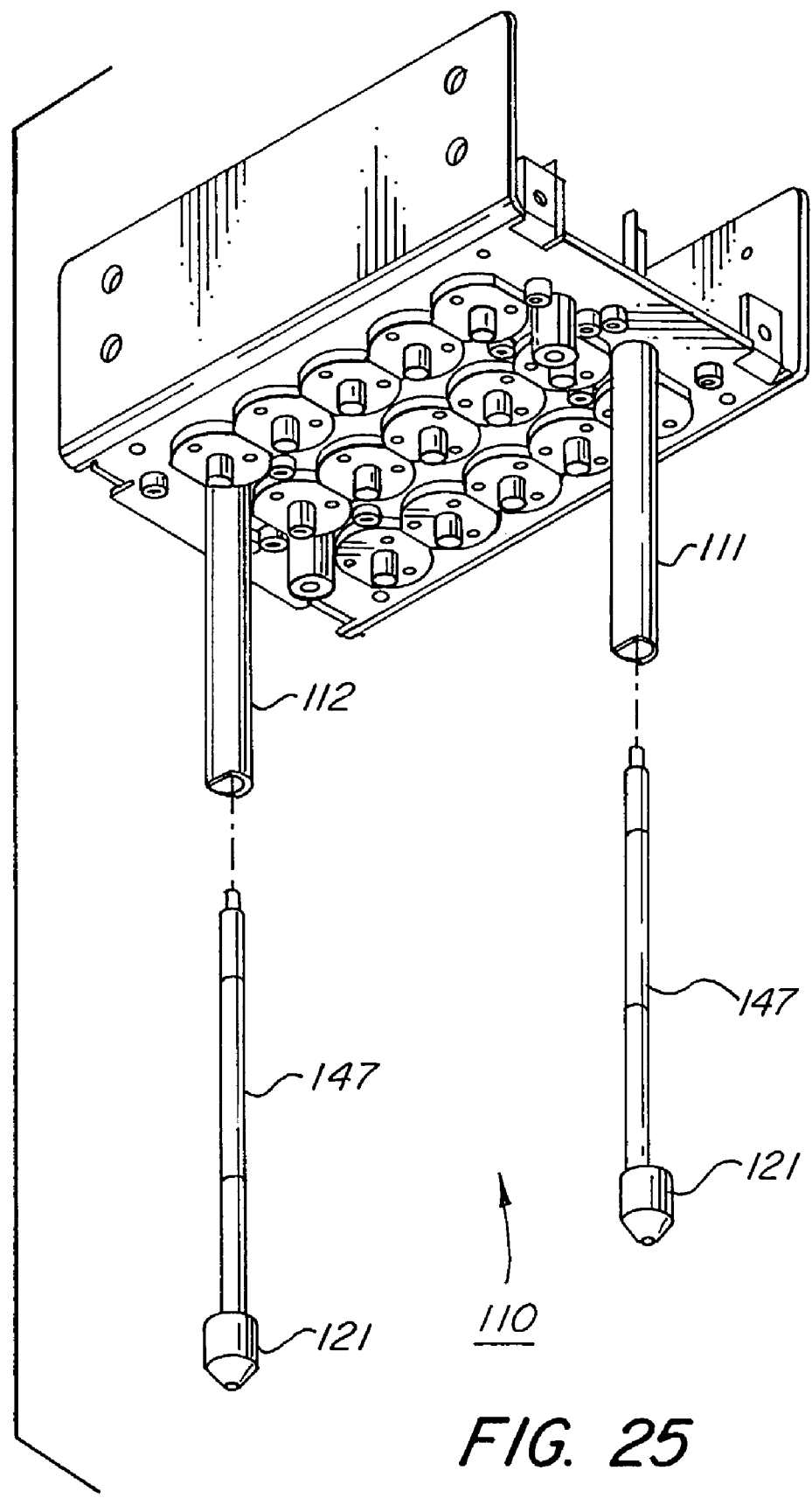
Figure 26:
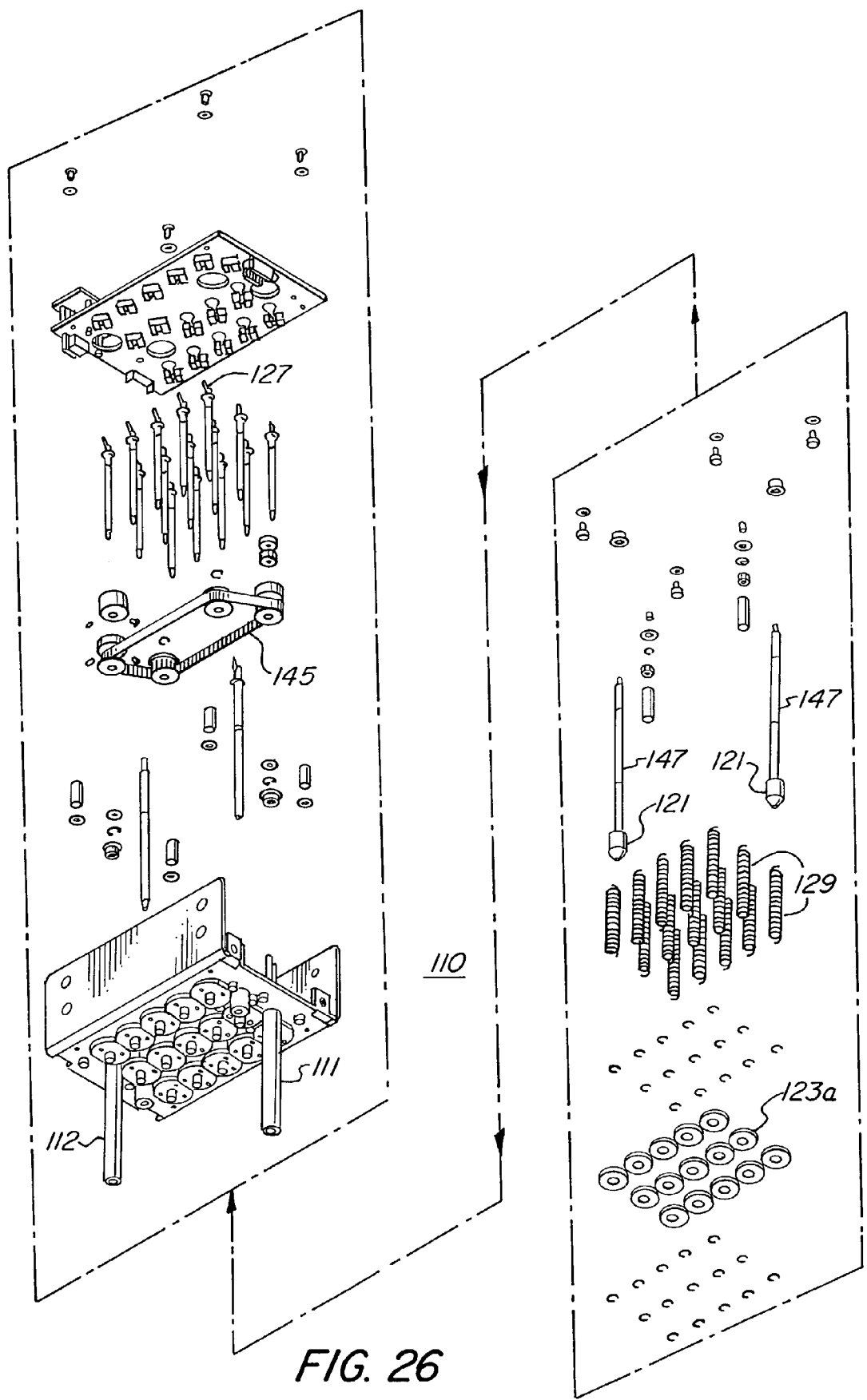
Figure 27:
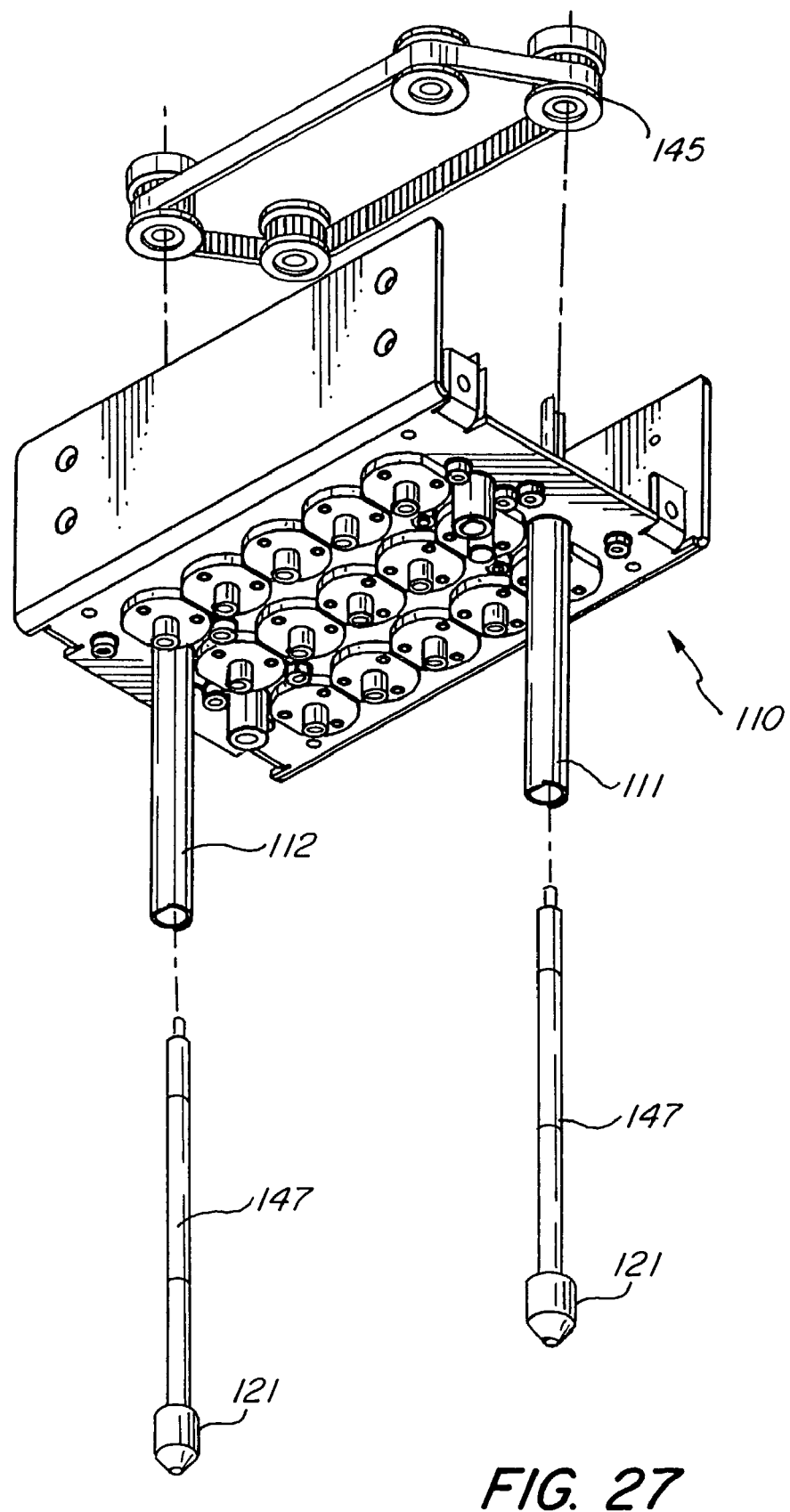

The lower end portion or eccentric portion 121 of the thick posts 111 and 112 is actuated by a drive 125 (FIGS. 28-31), which is housed by a cover 124 (FIG. 28), for a belt 145 (FIG. 26) inside the gripper head 110 that turns the eccentric posts 147, 147 (FIGS. 24-26) that extend from the end portions 121 inside the thick posts 111 and 112.

The bucket end sections 82, 83 include a shelf-like top portion 119 (FIGS. 40 and 50) having a post receiving opening 118 above a recess 105 and a similar post receiving opening 120 above a recess 106 that is deeper than the recess 105. The two thick posts 111, 112 are thus used for picking up a sample tube bucket 19 by entering the post receiving openings 120 in the bucket end sections 82, 83 (FIGS. 50-52) in a non-eccentric condition. The posts 111 and 112 are then placed in the eccentric position such that the eccentric created edge 121a fits in the recess 106 (FIGS. 50, 59 and 60) in the end sections 82 and 83 below the shelf portion 119.

The eccentric edge 121a of the posts 111, 112 engage the lower surface of the bucket shelf 119, which prevents removal of the eccentric portion 121 from the opening 120. Thus interference of the eccentric edge 121a with the shelf surface 119 enables the bucket gripper robot 7 to lift the sample tube bucket 19 using the thick posts 111 and 112 to engage the post receiving openings 118, 120 in opposite end sections 82 and 83 of the sample tube bucket 19.

Figure 39:
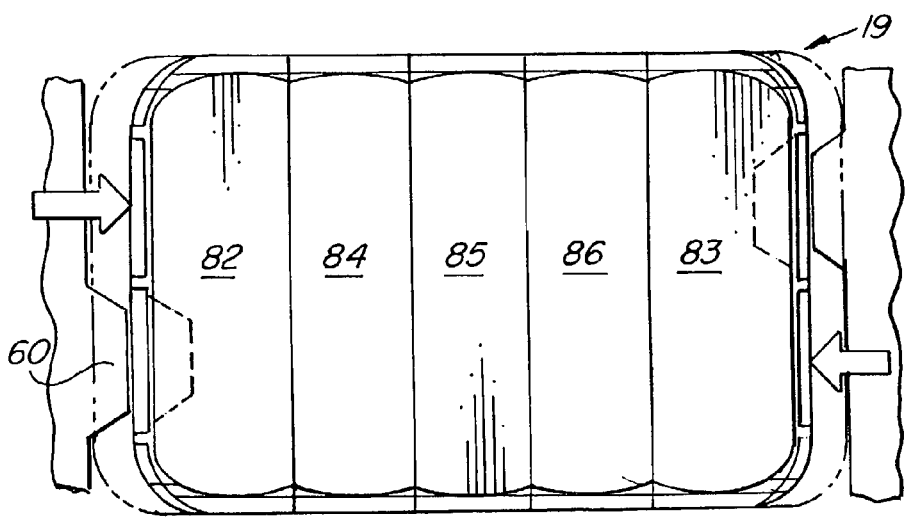
FIG. 39 is a simplified schematic bottom plan view of the bucket in a compressed condition for release from the hold down device.
Figure 40:
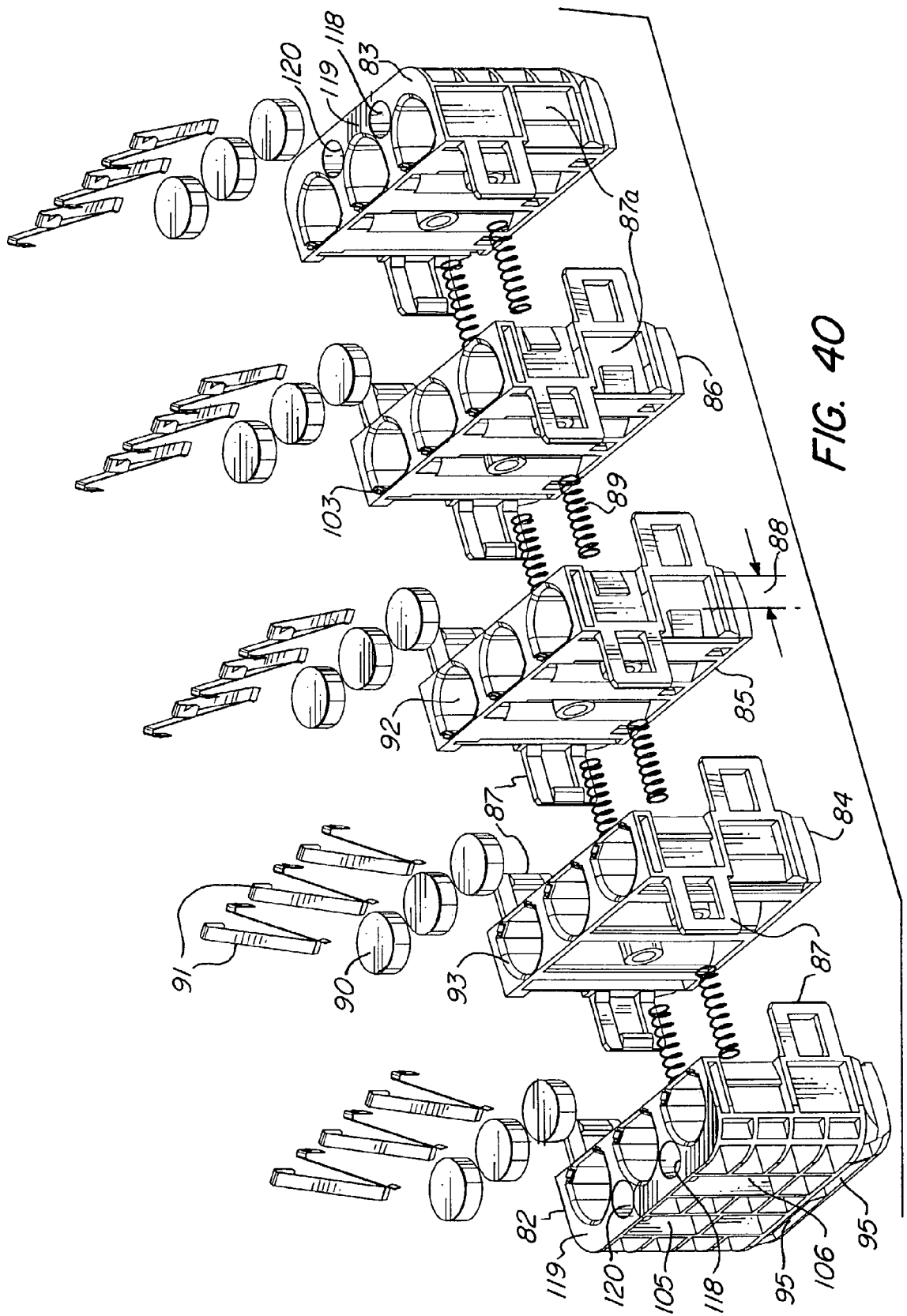
FIG. 40 is an exploded perspective view of the sample tube bucket elements.
Figure 41:
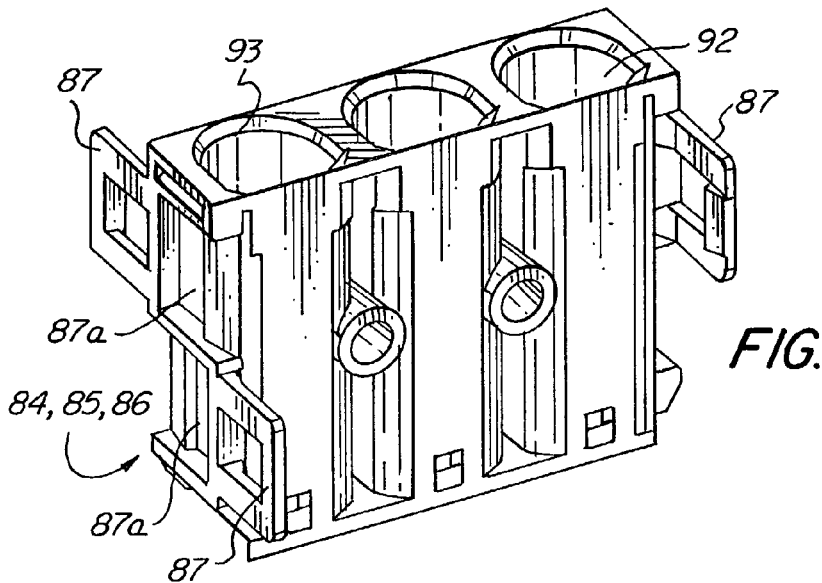
FIG. 41 is a perspective view of one of three similar middle sections of the sample tube bucket shown in FIGS. 37-40.
Figure 42:
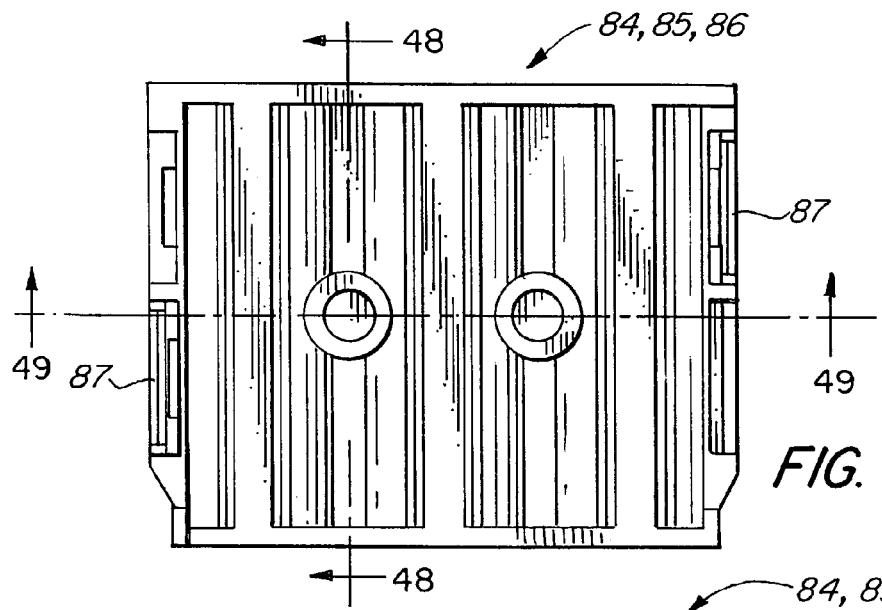
FIG. 42 is a front elevational view of the sample tube bucket.

During engagement of the bucket gripper robot 7 with a sample tube bucket 19, the bucket 19 is in a compressed condition (FIG. 39). The bucket 19 is also held in the compressed condition by the bucket gripper robot 7 when the bucket 19 is lifted and transported. The sample tube bucket 19 is also maintained in a compressed condition in the cross-pattern bucket receiving receptacles (not shown) of the centrifuge 4. The two thin posts 113 and 114 (FIGS. 29, 30, 31 and 59-60) pass into the respective post receiving openings 118 of the shelf 119 at the bucket end sections 82, 83 (FIG. 31) to engage a surface 122 at the bottom of the recess 105.

Figure 59:
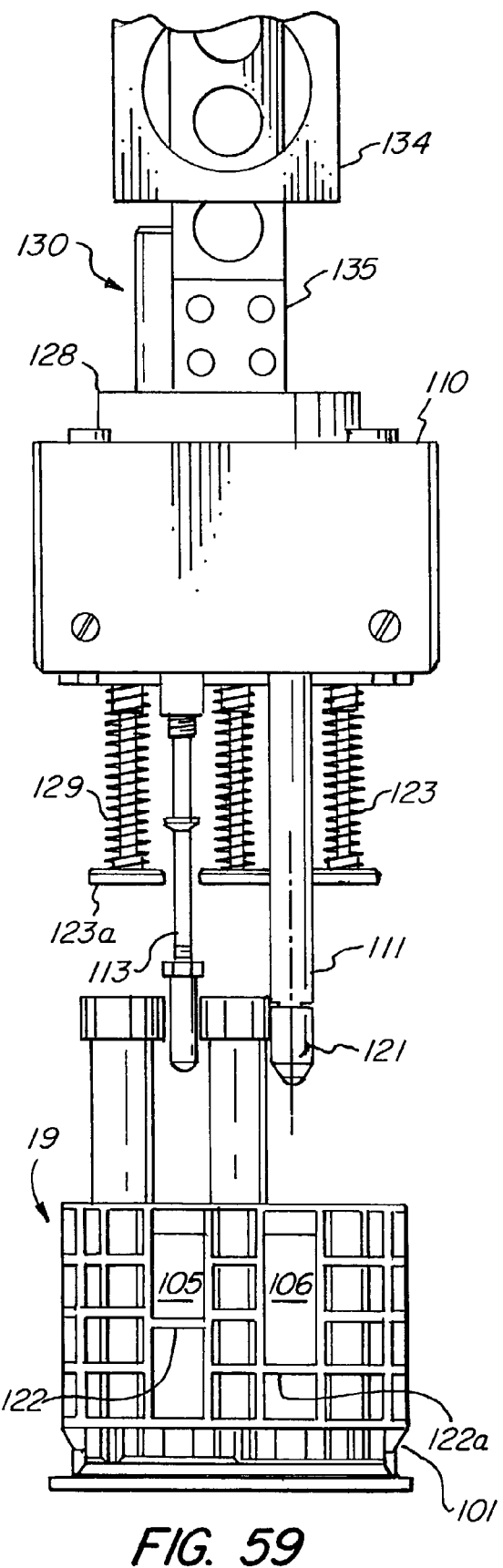
FIGS. 59 and 60 are fragmentary end elevation views of the input-output device and bucket gripper device for the bucket gripper robot before and after engagement with a sample tube bucket.
Figure 60:
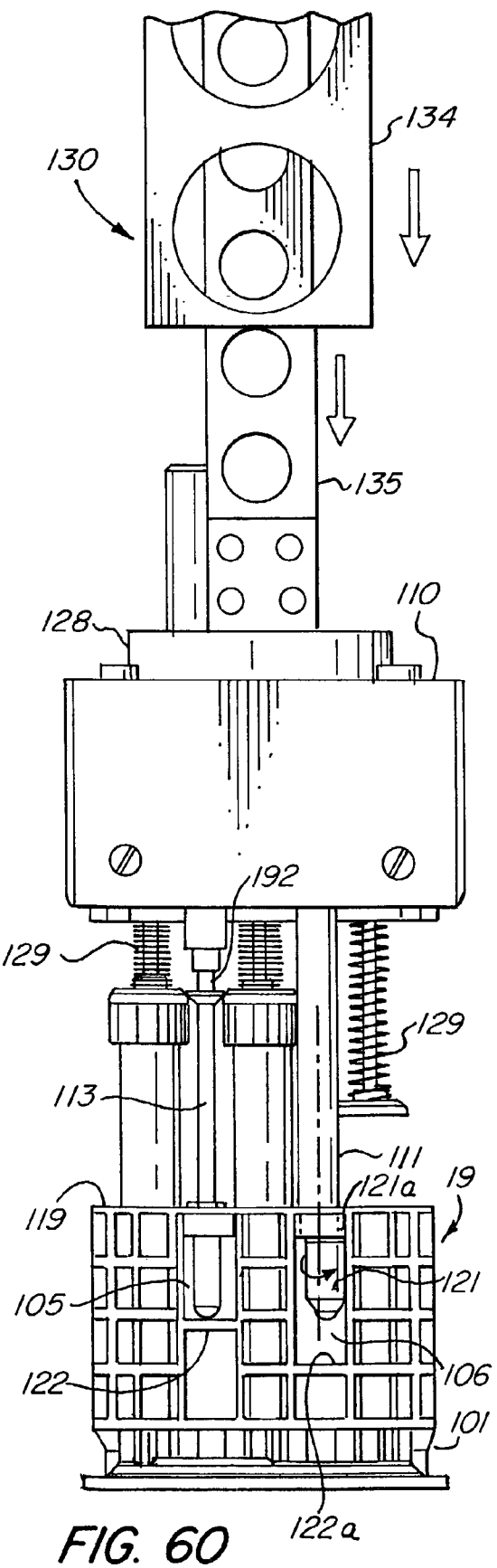

One of the thin posts 113, 114 (FIG. 31) is used purely for guidance and to prevent bucket tilt during bucket lifting and is shorter than the other thin post. The longer of the thin posts 113, 114, in addition to serving a guidance and tilt prevent function, is used to determine that a sample tube bucket 19 is present when the bucket gripper robot 7 descends to a bucket pick-up position. Thus the longer of the thin posts 113, 114 will compress in height when it engages the bucket surface 122 (FIG. 31) and such compression causes a signal to be generated. FIGS. 59 and 60 show an eccentric portion 121 of the thick post 111 in a gripping position in a sample tube bucket 19. FIGS. 59 and 60 also show at 192 the thin sensor post 113 compressed to indicate the presence of a sample tube bucket. FIG. 59 shows the normal protraction of the thin sensor post 113 when there is no sensing engagement with the sample tube bucket 19.

Thus when the thin sensor post 113, for example, engages the bucket surface 122, the post 113 will retract into the bucket gripper head 110 (FIGS. 59 and 60) and enable a sensor to detect the retractive movement via an optical flag, for example, and thereby provide an optical signal indicating the presence of a sample tube bucket 19. The bucket sensing optical signal also directs the eccentric portion 121 of the thick posts 111, 112 (FIGS. 59 and 60) to move into the eccentric position. The eccentric is driven by the motor 125 (FIG. 28) which moves the belt 145 (FIG. 26) to rotate the eccentric shafts 147 that are joined to the eccentric portions 121. Once the eccentric shafts 147 rotate the eccentric portions 121 to an eccentric position (FIG. 60) the bucket gripper robot 7 can move up with the sample tube bucket 19. It will be noted that a base surface 122a (FIGS. 50, 59 and 60) of the recess 106 in the sample tube bucket 19 clears the bottom of the eccentric portion 121 of the thick posts 111 and 112.

The bucket gripper head 110 (FIGS. 29 and 30) of the bucket gripper robot 7 also includes fifteen depending spring loaded retractable posts or plungers 123 that correspond to and align with the fifteen sample tube positions in a compressed sample tube bucket 19. An enlarged washer 123a is fixed to the lower end of each retractable plunger post 123 and a coil spring 129 (FIGS. 29 and 30) on the plunger 123, which bears against the washer 123a, urges the plunger 123 into a protracted position. The plunger post 123 is thus spring biased in a downwardly protracted position but has the capability to retract up into the bucket gripper head 110 of the bucket gripper robot 7.

Retractive movement of the plungers 123 is individually detected inside the bucket gripper head 110 by fifteen sensors that correspond to each of the fifteen plungers 123. The fifteen sensors detect the presence or absence of a sample tube for a particular sample tube position in the bucket. The plungers 123 can thus operate as detectors of broken sample tubes.

A guide 126 (FIG. 28) for the plungers 123 (FIGS. 29 and 30) guides retractive movement of the plunger 123 in the bucket gripper head 110. A mechanical flag 127 (FIGS. 26 and 28) on an upper end of the plunger post 123 moves parallel to the guide 126 and activates an optical sensor below the flag 127 when the plunger post 123 is retracted to indicate whether a sample tube is present.

When the four sample tube buckets 19 filled with up to sixty sample tubes are disposed in the centrifuge 4 there is a likelihood, especially with glass sample tubes, that one or more of the sample tubes will break during spinning because of high forces generated during the spinning operation. Before the bucket gripper head 110 releases a sample tube bucket 19 filled with sample tubes into the centrifuge 4 the operating software saves a record of the presence and location of sample tubes in the fifteen sample tube positions in the sample tube bucket 19. Such record is based on an identification of sample tube presence in the sample tube bucket 19 as determined by the optical sensors corresponding to the fifteen retractable plungers 123 of the bucket gripper head 110.

If there is a sample tube present in the sample tube bucket 19 the plunger 123 corresponding to the occupied sample tube position in the bucket 19 is moved up in a retracted position based on engagement of the plunger washer 123a with the capped end of the sample tube. If there is no sample tube present in one or more sample tube positions of the sample tube bucket 19, the plungers 123 corresponding to the sample tube positions in the bucket 19 remain protracted (a default position).

Therefore, the plunger sensors in the bucket gripper head 110 provide information before a centrifuge operation of whether or not there is a sample tube present in the sample tube bucket 19 for each sample tube position in the bucket 19. FIGS. 59 and 60 show plungers 123 in a retracted and non-retracted position relative to the bucket gripper head 110, indicating whether or not some or all sample tubes are present in the sample tube bucket 19. A record of sample tube occupancy in the sample tube bucket 19 is also obtained from the bucket gripper head 110 after the centrifuge operation is complete to determine whether or not there is a sample tube present in each sample tube position of the spun sample tube bucket 19.

Unit software will compare the sample tube position information after the centrifuge operation with the sample tube position information before the centrifuge operation and determine if there is a broken sample tube. Thus the unit software saves an information record of 4×15 sample tube positions for each sample tube bucket 19 before spinning and compares that information with position information obtained when the bucket gripper robot 7 removes the sample tube buckets 19 from the centrifuge 4 after the spin operation is completed.

When the sample tube buckets 19 are unloaded from the centrifuge 4 by the bucket gripper robot 7 and one of the plungers 123 is in the protracted default position, such protraction may indicate that a sample tube is broken. If that plunger 123 was in a retracted position before the spinning operation, indicating the presence of a sample tube, then it can be determined from a comparison of the tube occupancy record information of the sample tube bucket before and after centrifuge spinning that a particular sample tube in a particular position in the sample tube bucket 19 is broken. Thus the bucket gripper robot 7 has a broken sample tube detector feature in the bucket gripper head 110.

When a broken sample tube is discovered after a centrifuge spin operation the bucket gripper head 110 will release the sample tube bucket 19 so that the bucket 19 remains in the centrifuge 4. The bucket gripper robot 7 will then move up and out of the centrifuge 4 without the bucket 19. The centrifuge lid will close and further robot operation will cease. A signal will be sent to a monitoring station that a broken sample tube is detected. The centrifuge lid must then be opened and any debris inside must be removed.

Thus there are sixteen optical sensors inside the bucket gripper head 110. Fifteen sensors are used for detecting broken sample tubes and the sixteenth sensor is for detecting the presence of a sample tube bucket 19. An electronic intelligence unit communicates with the robot control cabinet 10 based on information detected by the bucket gripper robot 7.

It is necessary to move the sample tube buckets 19 a certain height up from the tabletop 5 and down into the centrifuge 4 and keep the movement mechanism within the height of the unit cabinet 2 (FIG. 1). Vertical movement of the bucket gripper robot 7 in the "z" direction cannot be accomplished with one single post because the length of a single post would be longer than the distance between the tabletop 4 and the top of the cabinet 2. Therefore a single post would extend above the unit 2, which is not acceptable. To solve this problem an input-output extender device 130 for raising and lowering the sample tube buckets 19 (FIGS. 3, 15, 16, 17 and 8-20) was developed.

Figure 28:
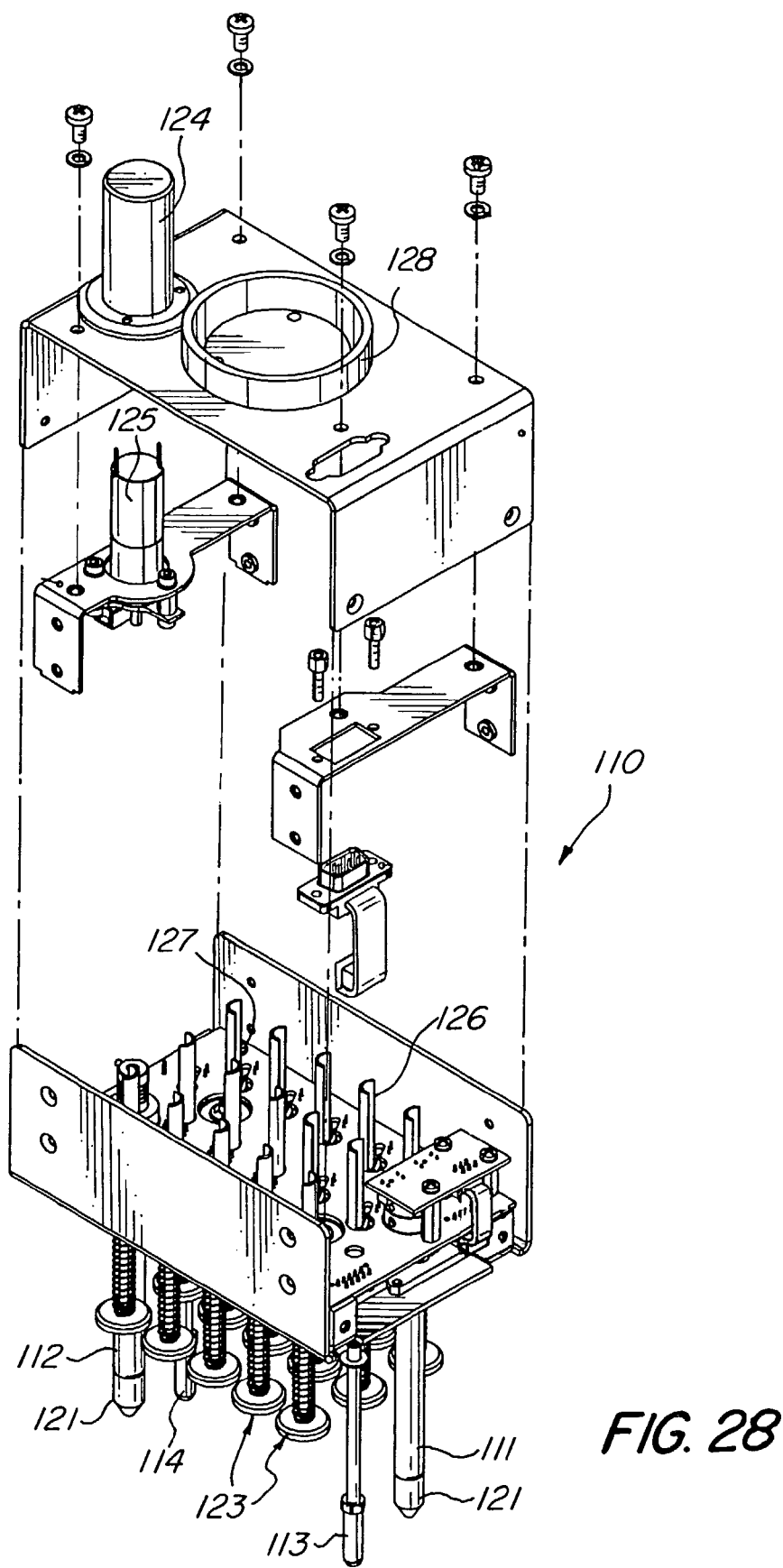
Figure 29:
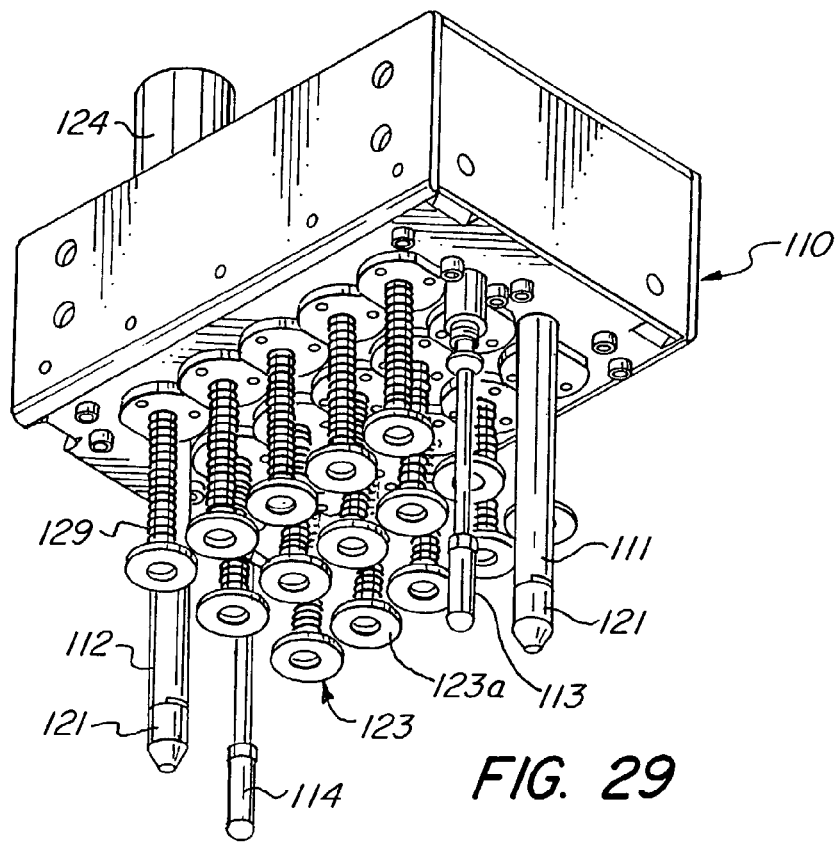
Figure 30:
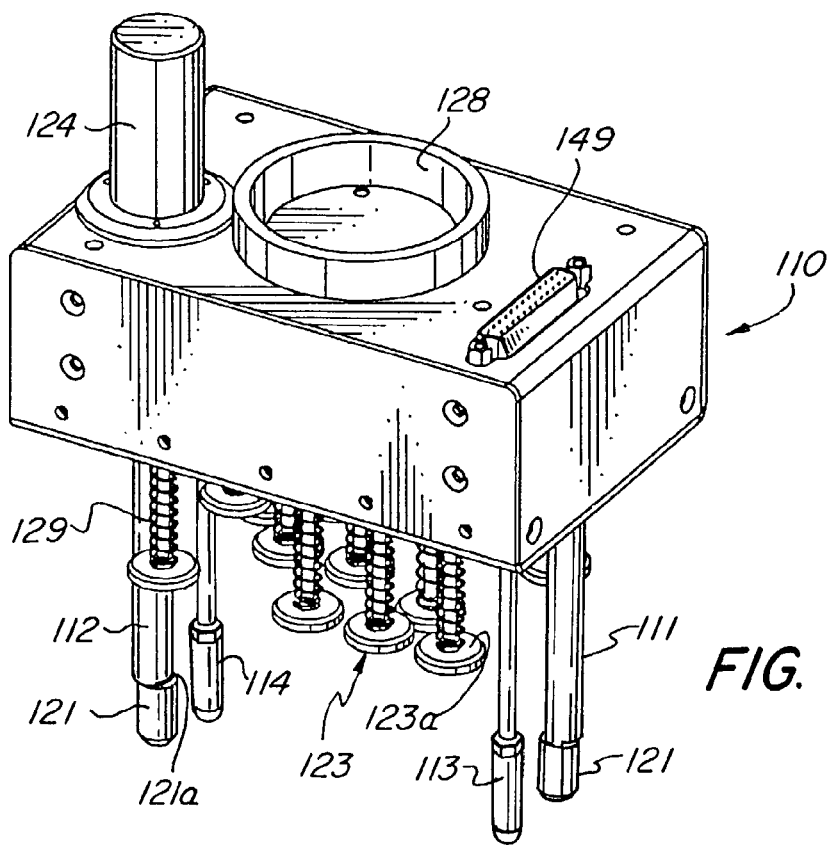
Figure 31:
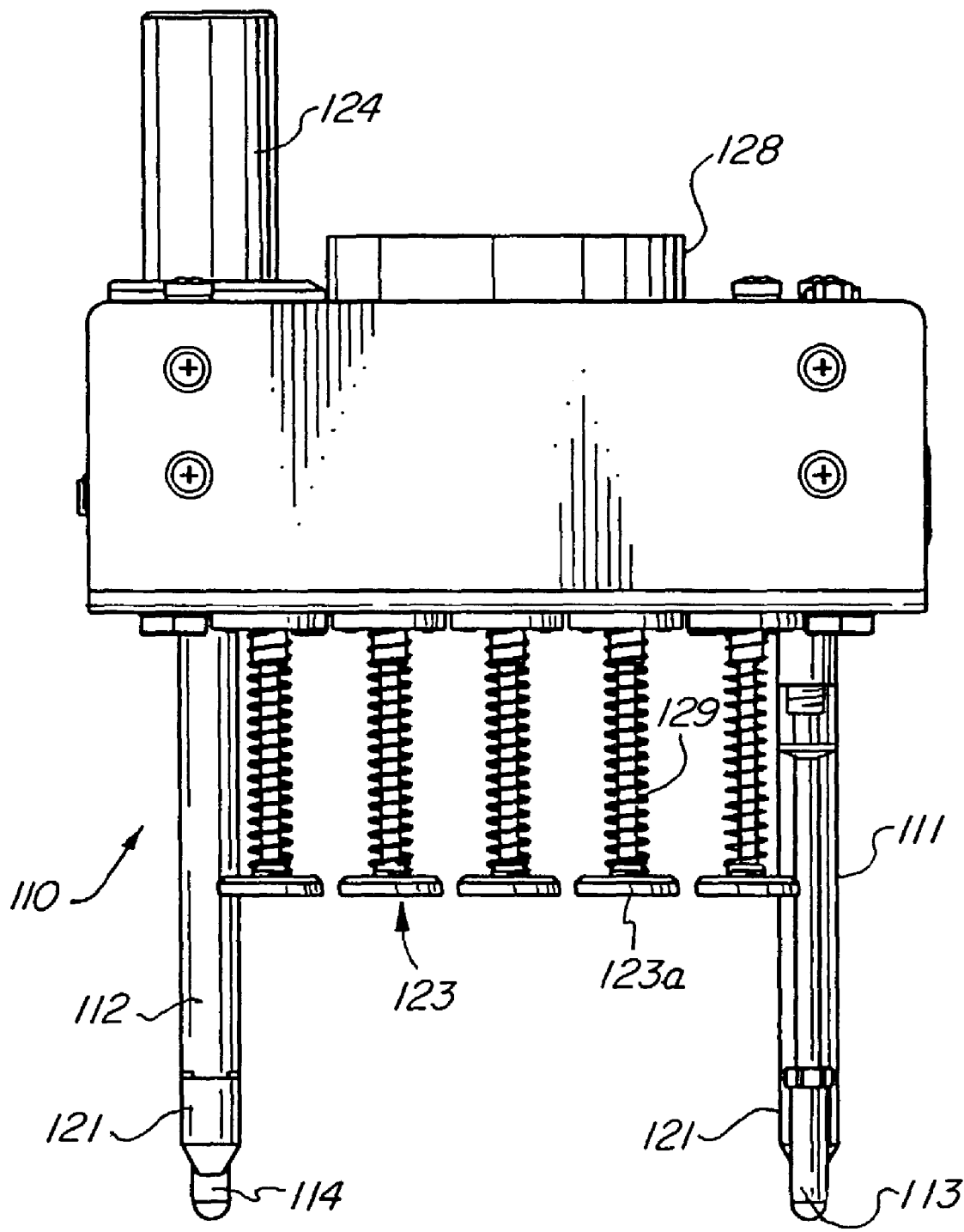

A mounting collar 128 (FIGS. 29 and 30) for the extender device 130 is provided on the bucket gripper head 110. A mounting hub 143 (FIGS. 16 and 21) at the end of an inner post 135 (FIG. 15) is mounted to the mounting collar 128 (FIGS. 28-30). FIGS. 17-20 show the bucket gripper extender device 130 in different extended positions. A flexible wiring harness 144 (FIG. 16) is joined at one end to a connector 149 (FIGS. 29 and 30) on the bucket gripper head 110 and secured to a bracket 145 (FIGS. 16 and 21) that moves with the inner post 134. An opposite end of the wiring harness 144 is joined to the support plate 142 (FIG. 16) at 146 for connection to a connector 157 (FIG. 7). The connector end 149 (FIGS. 29 and 30) of the harness 144 (FIG. 16) can thus move with the inner post 135 and the bucket gripper head 110 (FIG. 15) while maintaining an electrical connection with the bucket gripper head 110 at the connector 149 (FIGS. 29 and 30).

The extender device 130 includes two telescoping posts 134, 135 (FIGS. 15-21) that are movable on the support plate 142. A drive motor 131 (FIGS. 15-21) at the support plate 142, drives a toothed endless belt 132 (FIGS. 15 and 17-21) that moves the outer post 134.

Figure 15:
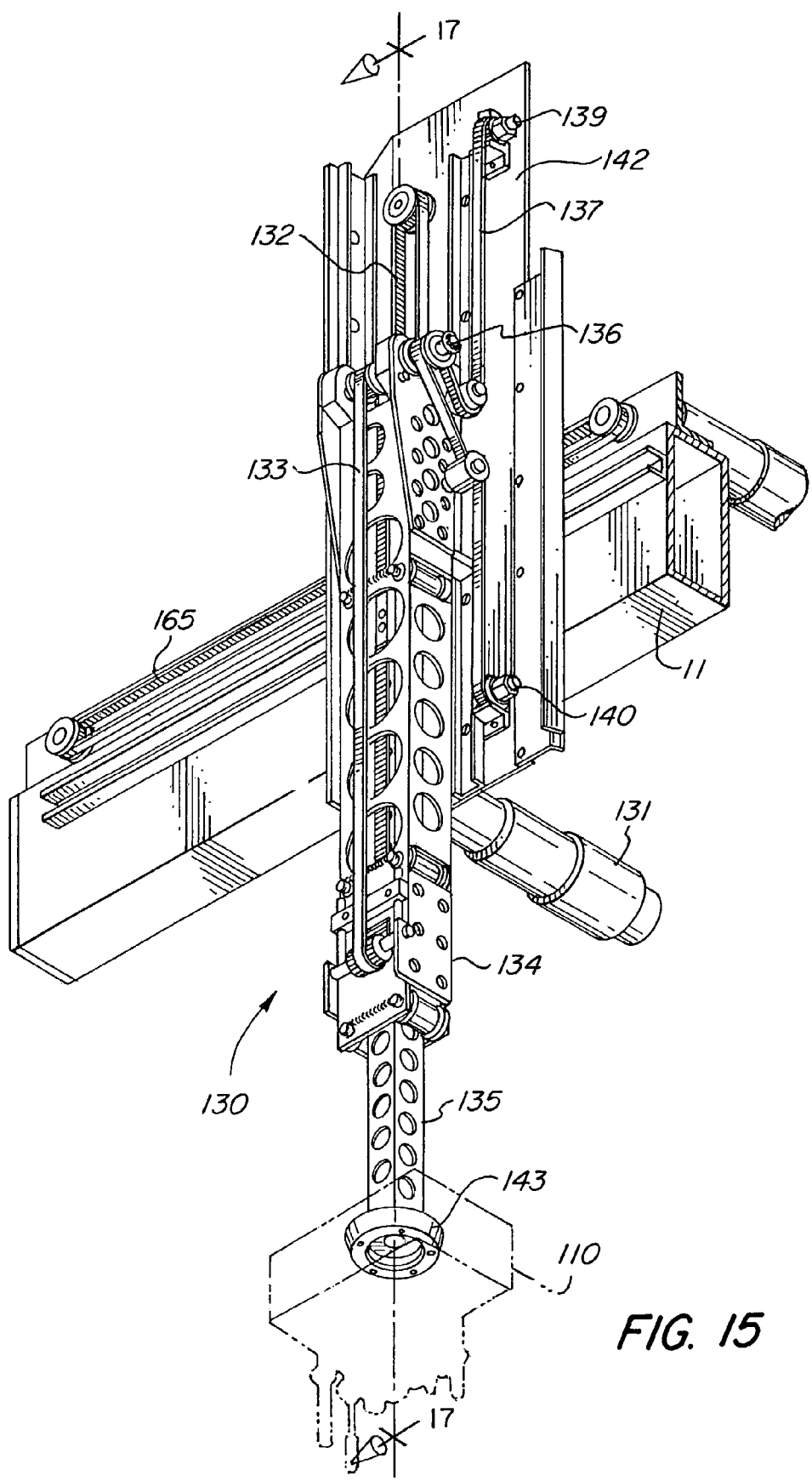
FIG. 15 is a perspective view of an input-output device of the bucket gripper robot, in a slightly extended position for raising and lowering the bucket gripper head (dotted) relative to the robot support beam.
Figure 16:
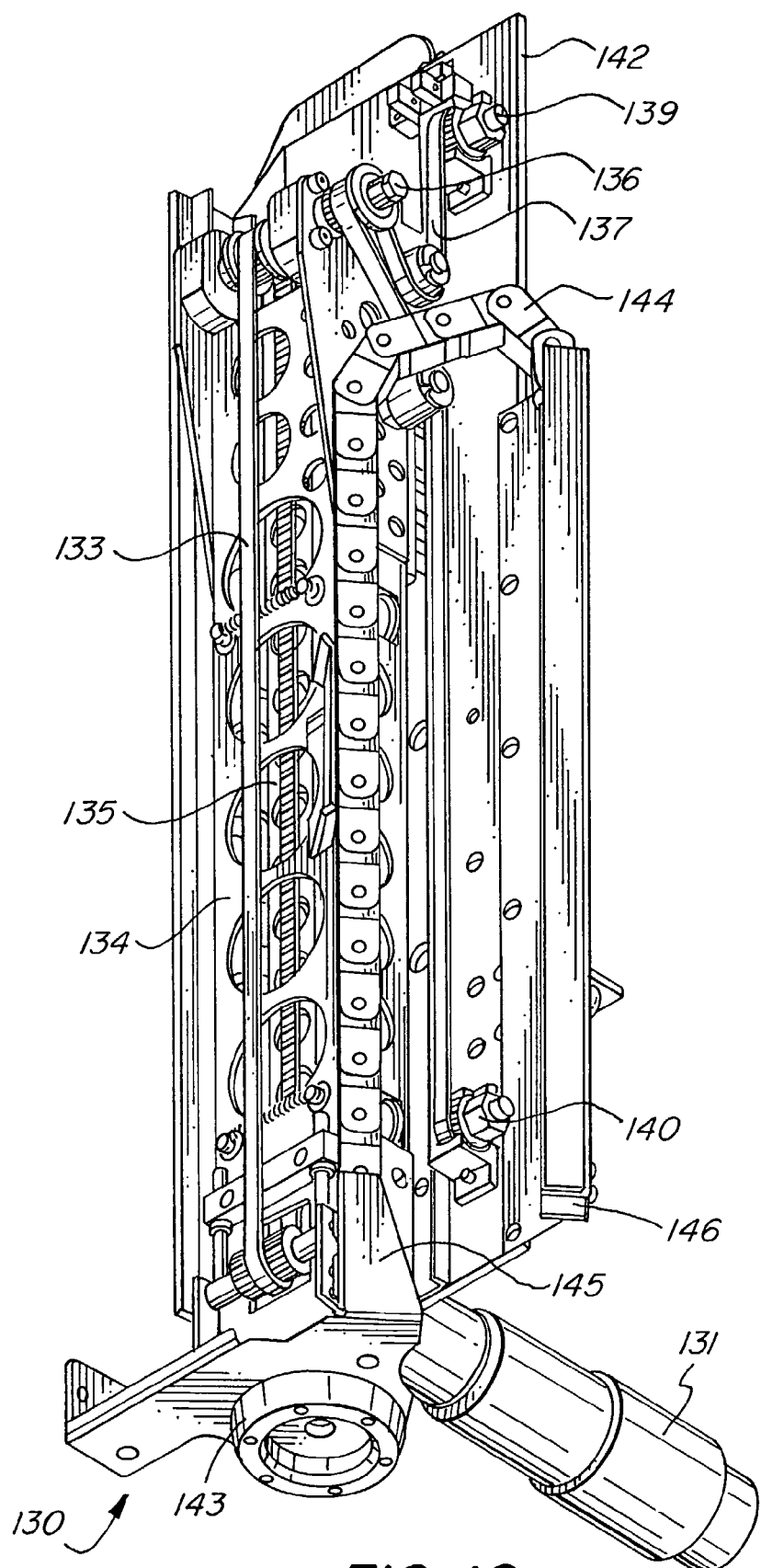
FIG. 16 is a view similar to FIG. 15 showing the input-output device fully retracted and including a flexible harness.
Figure 17:
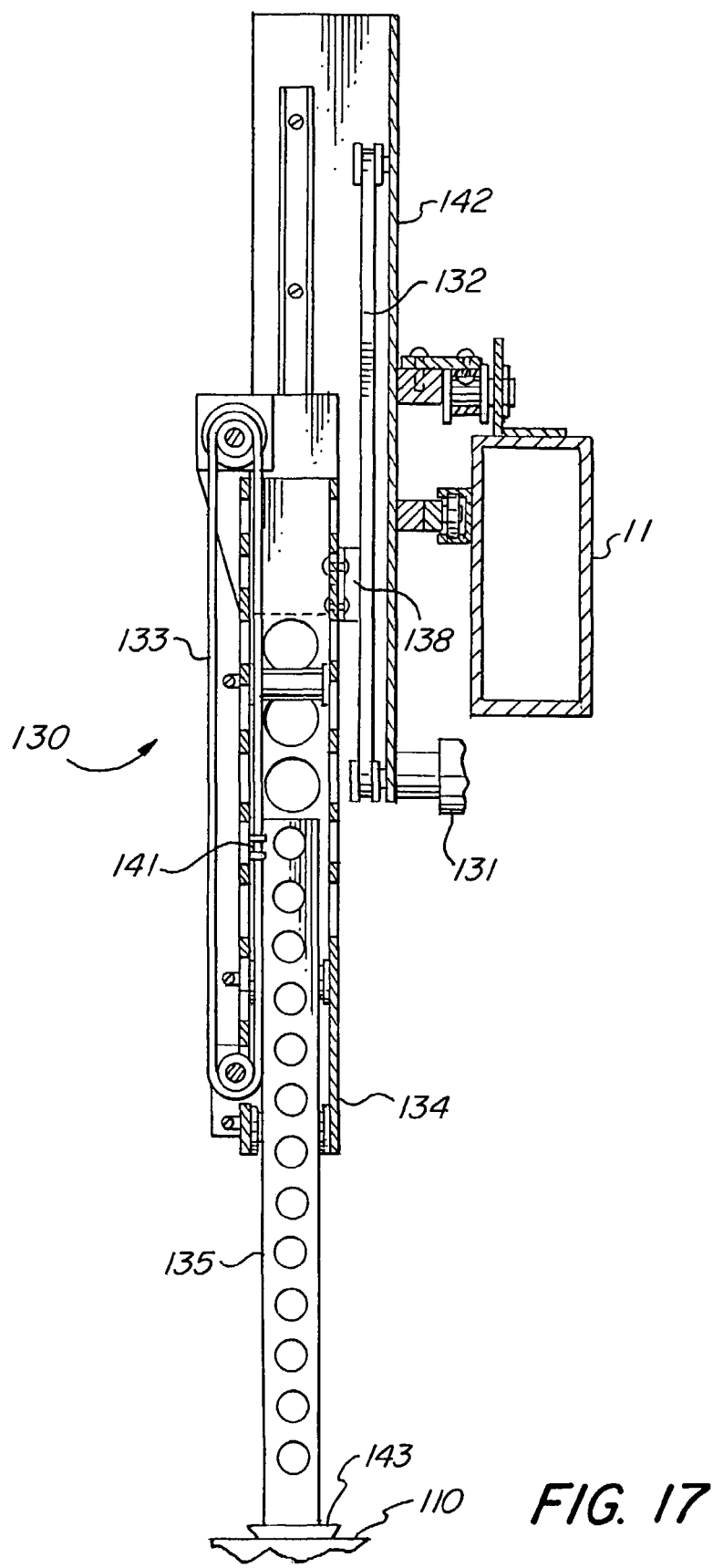
FIG. 17 is a simplified sectional view taken on the line 17-17 of FIG. 15.

Referring to FIGS. 13, 14, 15 and 21 the toothed belt 132 (FIG. 21) is secured by a bracket 138 (FIG. 21) to the outer post 134 to move the outer post 134 up and down. Vertical movement of the outer post 134 causes a spindle 136, mounted to an upper end of the outer post 134 (FIGS. 15 and 21), to rotate relative to a fixed toothed belt 137 (FIGS. 15 and 16). The fixed belt 137 has one end fixed at 139 to an upper end portion of the support plate 142 (FIGS. 15 and 16) and an opposite end fixed at 140 to a lower end portion of the support plate 142. Rotation of the spindle 136 causes movement of a toothed endless belt 133 mounted on the outer post 134 (FIGS. 15, 16 and 21) and attached to the inner post 135 by fasteners 141 (FIG. 17).

Figure 18:
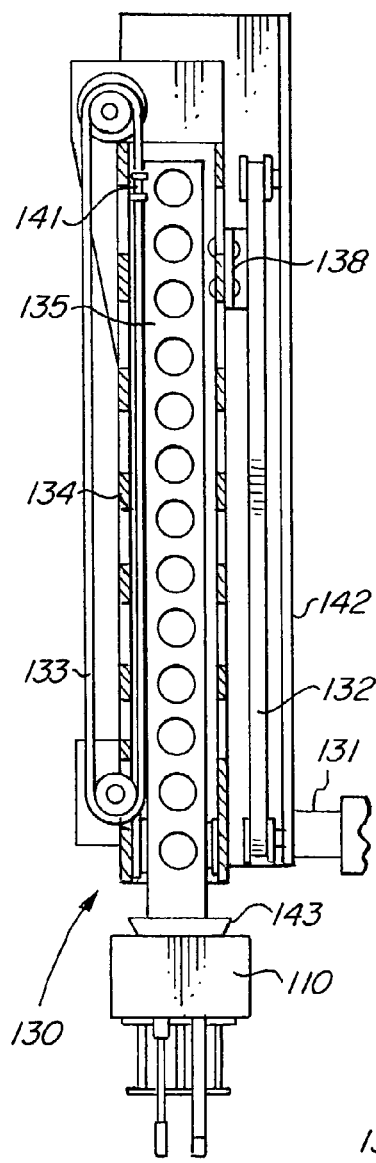
FIGS. 18-20 show three views of the input-output device of FIG. 17 in progressively extended positions.
Figure 19:
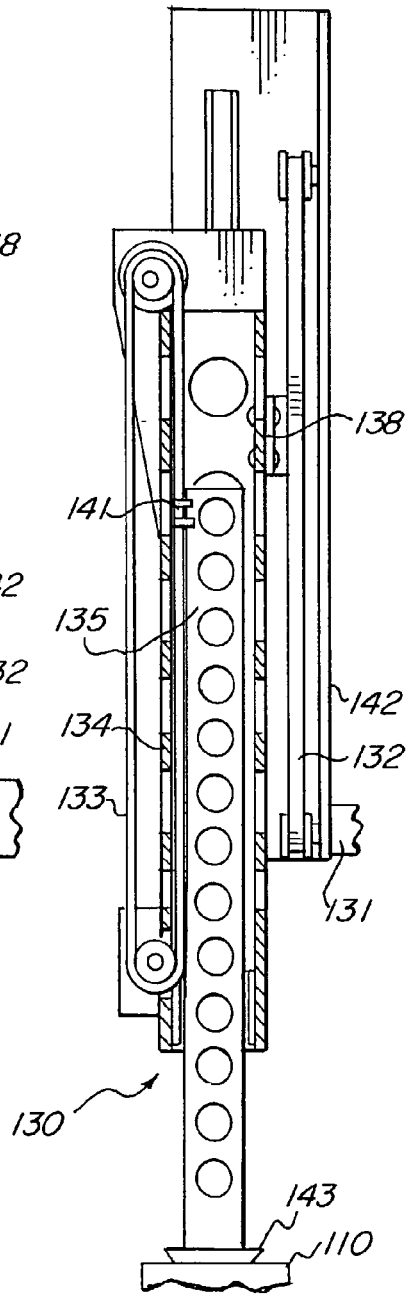
Figure 20:
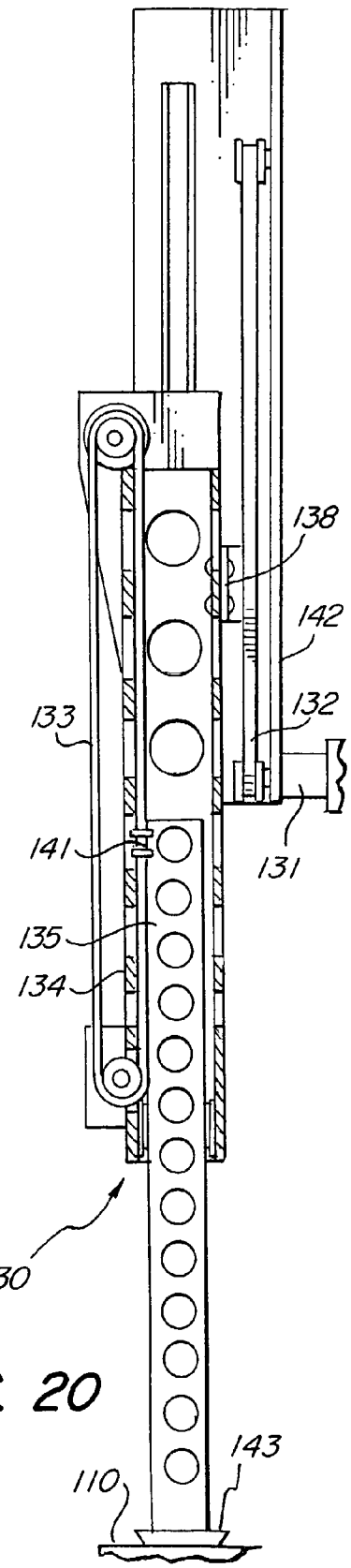
Figure 21:
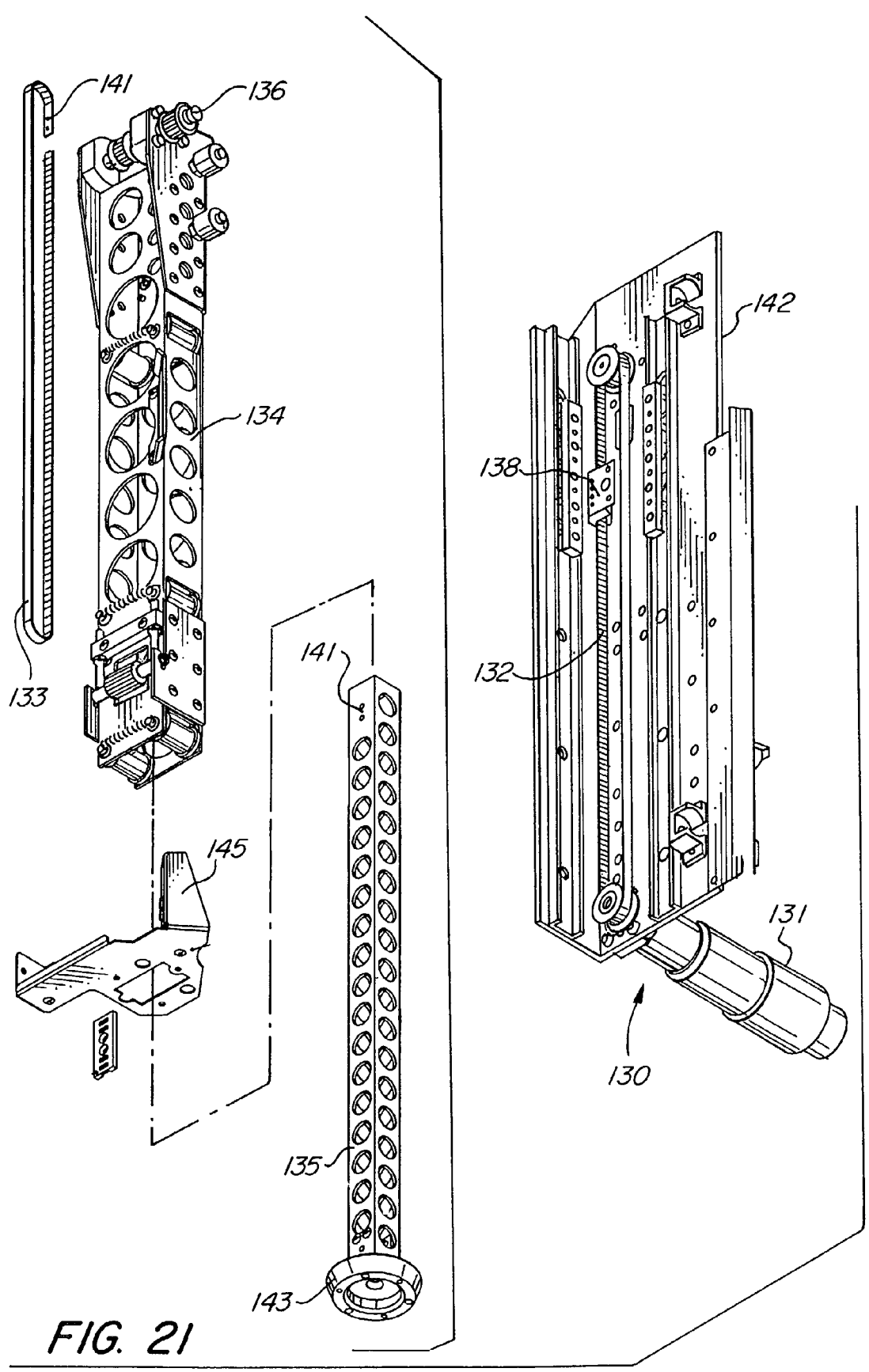
FIG. 21 is a partially exploded perspective view of the input-output device as shown in FIG. 15, with some parts omitted for purposes of clarity.
Figure 22:
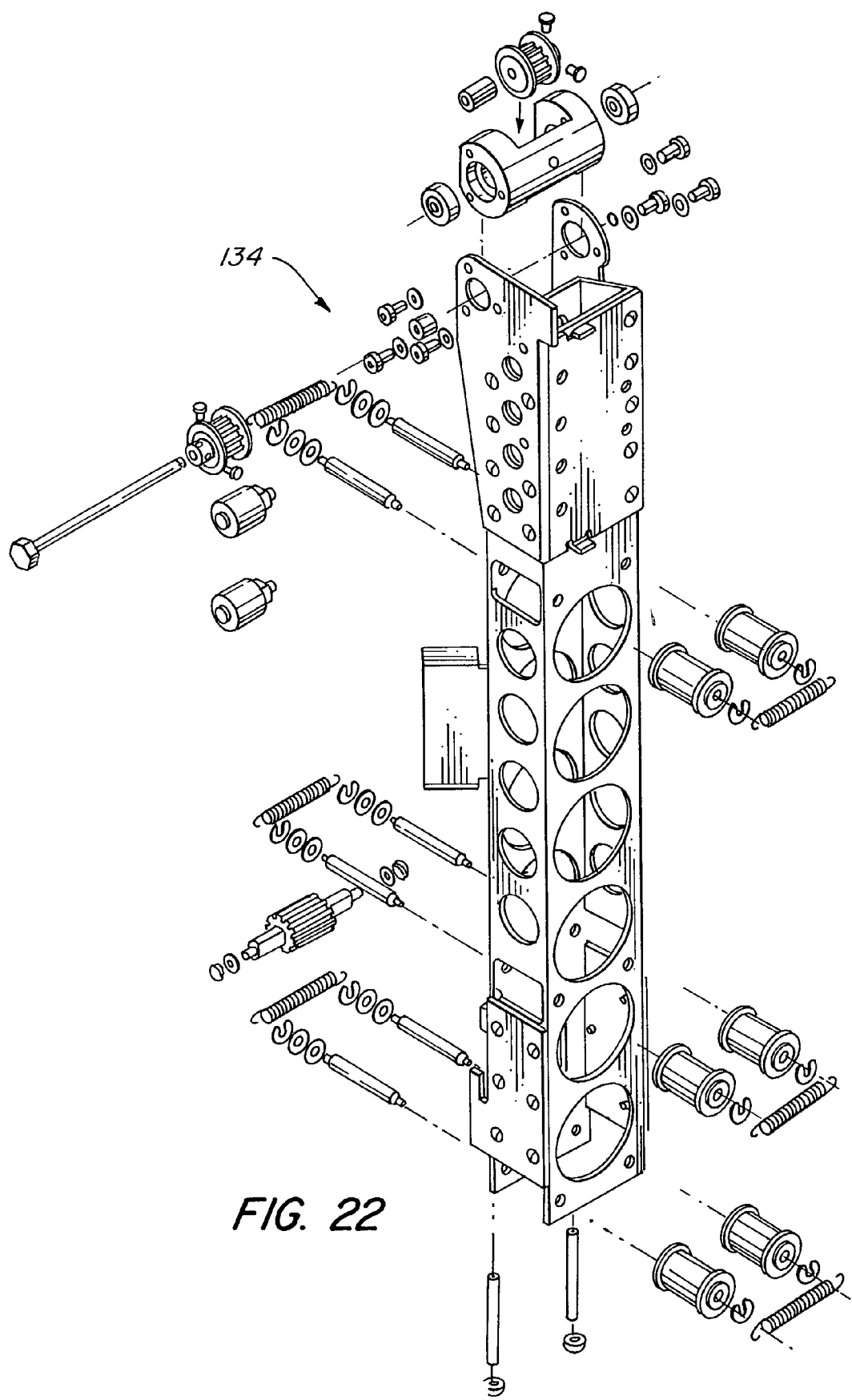
FIG. 22 is an exploded perspective view of the outer telescoping member of the input-output device shown in FIG. 21.
Figure 23:
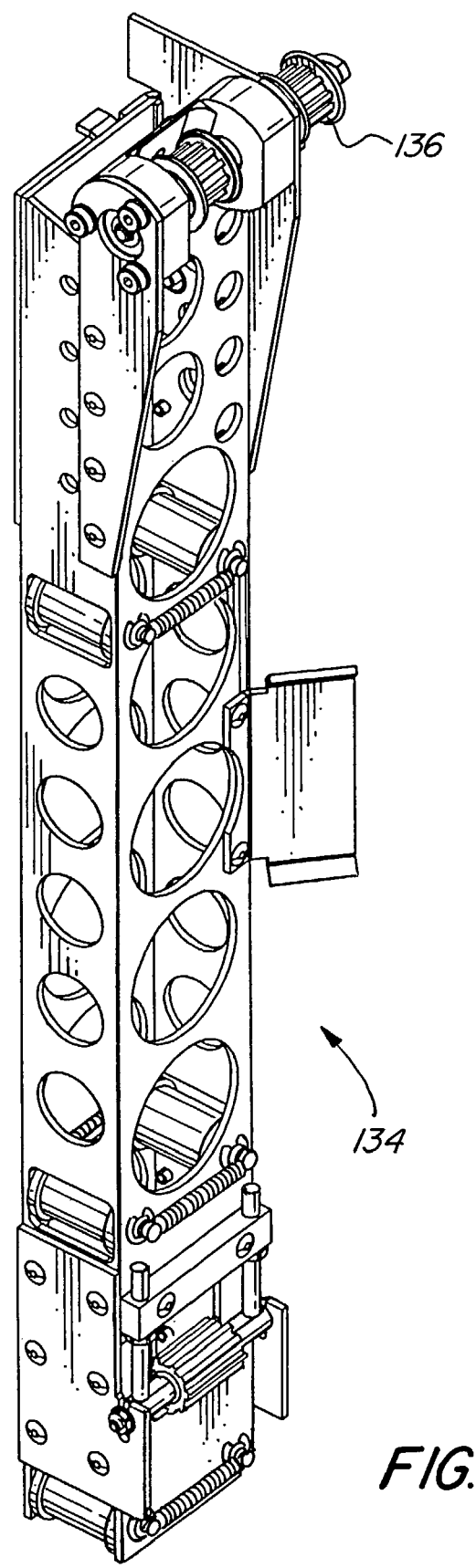
FIG. 23 is an unexploded perspective view of the outer telescoping member shown in FIG. 22.

Movement of the endless belt 133 thus raises or lowers the inner post 135 relative to the outer post 134 (FIGS. 18-20). It should be noted that the inner and outer posts 134 and 135 extend and retract simultaneously. Thus the inner and outer posts 134 and 135 move at the same rate, in the same direction, at the same time.

A various changes can be made in the above constructions and methods without departing from the scope of the invention, it is intended that all matter contained in the above description or shown in the accompanying drawings shall be interpreted as illustrative and not in a limiting sense.

What is claimed is:

1. A sample tube holder comprising,
    a) a housing having a predetermined number of sample tube openings for receiving sample tubes, said housing including a plurality of adjacent section members including a pair of end section members, and at least one middle section member, assembled together in side-by-side arrangement such that each of said section members is movable toward and away from an adjacent section member,
    b) biasing means provided between the end section members and the at least one middle section member to maintain the end section members and the at least one middle section member in a side-by-side spaced relationship, said biasing means having a normally expanded condition to define a normally expanded condition of the housing, said housing having a compressed condition when opposing forces applied to the end section members overcome and compress the biasing means a predetermined amount and reduce the side-by-side spaced relationship between each of the section members the predetermined amount, and
    c) connecting means on each of the section members, the connecting means adapted for engagement with each other and for engagement of each of the section members together in a compressible and expandable accordion-like arrangement when the biasing means is (1) urged from the normally expanded condition to the compressed condition or (2) allowed to expand from the compressed condition to the normally expanded condition, respectively, wherein the at least one middle section member and the end section members each have opposite outside wall portions, and the connecting means are provided on the opposite outside wall portions of the at least one middle section member and the end section members, and the connecting means include (1) at least one clasp portion extending from each of the opposite outside wall portions of each of the section members, and (2) at least one corresponding recess in each of the opposite outside wall portions of each of the section members, such that the clasp portions engage the recesses of respective adjacent section members.

2. The sample tube holder as claimed in claim 1 including three of said middle section members between said end section members, and each of the middle section members and the end section members have sample tube openings for receiving sample tubes.

3. The sample tube holder as claimed in claim 1 wherein each of the end section members of said housing includes at least one post receiving opening for receiving at least one post for holding said end section members in said compressed condition.

4. The sample tube holder as claimed in claim 1 wherein said housing includes a hold down recess for engagement by a hold down tool for holding the housing in a fixed position during removal of sample tubes from the sample tube openings of said housing.

\* \* \* \* \*